(12) United States Patent
Rosenbaum et al.

(10) Patent No.: US 7,052,705 B2
(45) Date of Patent: May 30, 2006

(54) ANTI-ANGIOGENIC PEPTIDES

(75) Inventors: Jan Susan Rosenbaum, Cincinnati, OH (US); David R. Jones, Milford, OH (US); George Brian Whitaker, West Chester, OH (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 487 days.

(21) Appl. No.: 10/263,162

(22) Filed: Oct. 2, 2002

(65) Prior Publication Data

US 2003/0186868 A1 Oct. 2, 2003

Related U.S. Application Data

(60) Provisional application No. 60/326,712, filed on Oct. 3, 2001.

(51) Int. Cl.
*A61K 38/12* (2006.01)
*A61K 38/16* (2006.01)
*A61K 39/00* (2006.01)

(52) U.S. Cl. .................................. 424/326; 530/185.1

(58) Field of Classification Search ............. 424/185.1; 530/326
See application file for complete search history.

(56) References Cited

U.S. PATENT DOCUMENTS 5,919,899 A * 7/1999 Persico et al. ............... 530/350

OTHER PUBLICATIONS

Sinha et al, Antimicrob Agents Chemother 47(2): 494-500, Feb. 2003, abstract only.*
Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Sinha et al, Antimicrob Agents Chemother 47(2): 494-500, Feb. 2003.*
Soker et al. (1997) J. Biological Chemistry 272:31582-31588.
Migdal et al. (1998) J. Biological Chemistry 273:22272-22278.
Whitaker et al. (2001) J. Biological Chemistry 276:25520-25531.

* cited by examiner

*Primary Examiner*—Christina Chan
*Assistant Examiner*—Phuong Huynh
(74) *Attorney, Agent, or Firm*—Valeta Gregg, Esq.

(57) ABSTRACT

Peptides that specifically interfere with the ability of $VEGF_{165}$ to interact with the NP-1 receptor or with a VEGFR-2/NP-1 co-receptor complex are disclosed. The inventive peptides are useful to control pathological angiogenesis, such as occurs in cancer and other diseases. The peptides are based on a combination of basic residues contained within Exon 6 of human placental growth factor (PlGF), coupled at the carboxyl terminus to either Exon 8 of $VEGF_{165}$ or Exon 7 of PlGF. The peptides behave as antagonists of $VEGF_{165}$ signaling through a mechanism that involves competition for $VEGF_{165}$ binding at either the VEGFR-2/NP-1 complex or NP-1, without affecting VEGF signaling through other pathways. This binding is sufficient to attenuate pathological angiogenesis such as occurs in tumor growth.

3 Claims, 13 Drawing Sheets

| Peptide sequence and amino acid identification | |
|---|---|
| AA # | 1 2 3 4 5 6 7 8 9 10 11 12 13 14 15 16 17 18 19 20 21 22 |
| P6: SEQ ID NO: 1 | RRPKGRGKRRREKQRP |
| P6P7: SEQ ID NO: 7 | RRPKGRGKRRREKQRPDAVPRR |
| P6V8: SEQ ID NO: 4 | RRPKGRGKRRREKQRPCDKPRR |
| P7: SEQ ID NO: 3 | RPDAVPRR |
| V8: SEQ ID NO: 2 | RPCDKPRR |

FIG. 6

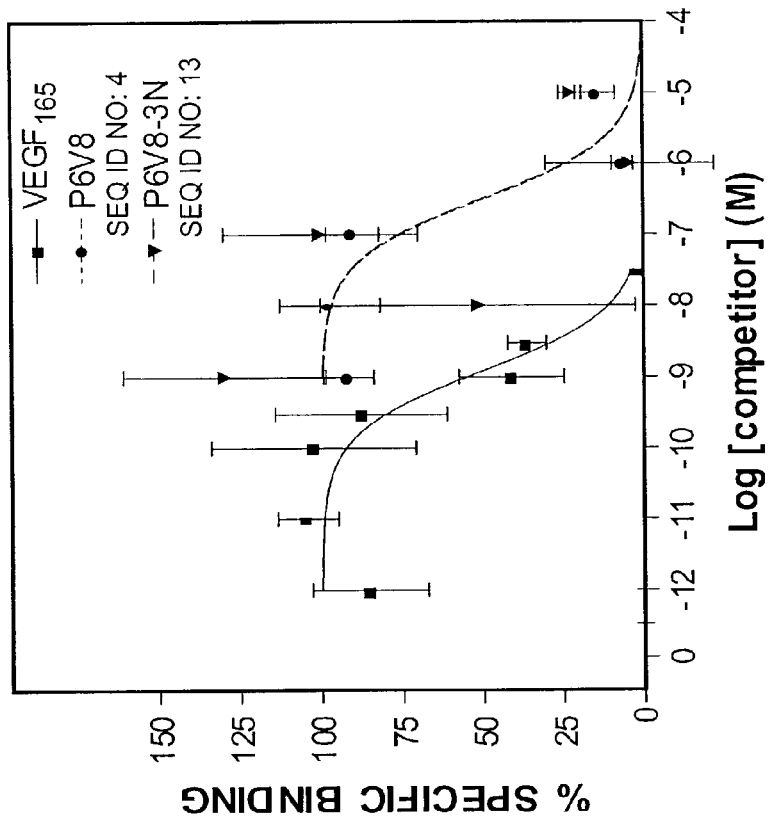
FIG. 9B
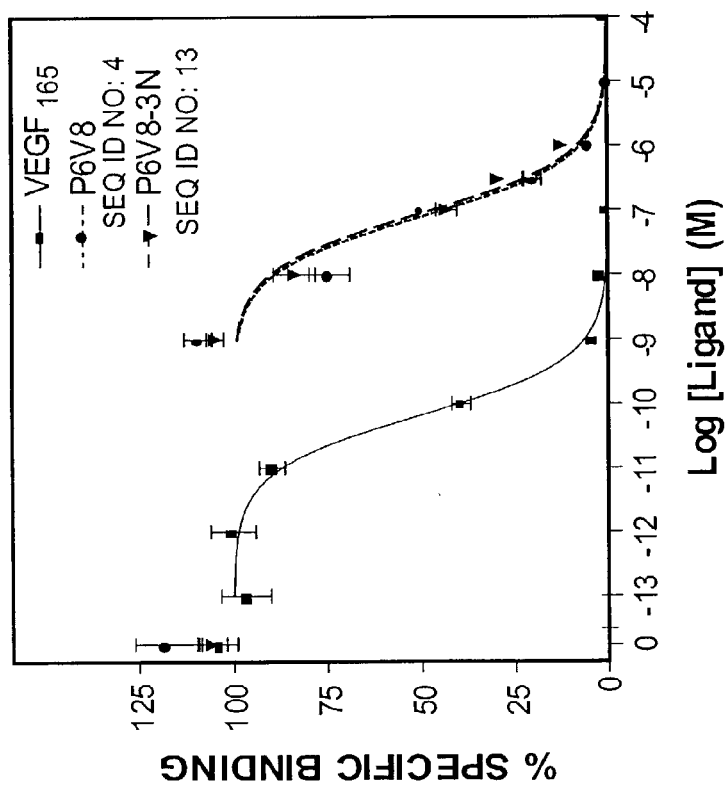
FIG. 9A
| CELLS | TRACER CONC. | $IC_{50}VEGF_{165}$ | $IC_{50}P6V8$ | $IC_{50}P6V8-3N$ |
|---|---|---|---|---|
| HUVEC | 162 pM | $6.69 \times 10^{-11}$ | $7.84 \times 10^{-8}$ | $8.88 \times 10^{-8}$ |
| COS-01 | 287 pM | $1.21 \times 10^{-9}$ | $3.07 \times 10^{-7}$ | $3.21 \times 10^{-7}$ |
FIG. 9C

ANTI-ANGIOGENIC PEPTIDES

This application claims priority to U.S. Provisional Application No. 60/326,712 filed Oct. 3, 2001.

Throughout this application, various publications are referenced. The disclosures of these publications in their entireties are hereby incorporated by reference into this application.

FIELD OF THE INVENTION

The invention is directed to novel peptide antagonists of the NP-1 receptor or the VEGFR-2/NP-1 co-receptor complex.

BACKGROUND OF THE INVENTION

Vascular endothelial growth factor (VEGF) is a central regulator of angiogenesis (formation of new blood vessels from pre-existing vessels) and vasculogenesis (development of embryonic vasculature through an influence on endothelial cell differentiation and organization). Diseases that are characterized by abnormal angiogenesis and vasculogenesis, such as cancer, show abnormal production of VEGF. Thus, control of VEGF function may be one means to control or treat these diseases.

It is known that VEGF exists in multiple protein isoforms such as $VEGF_{165}$, $VEGF_{121}$, $VEGF_{145}$, $VEGF_{183}$, $VEGF_{189}$, $VEGF_{206}$. The isoforms arise from alternate splicing of the VEGF gene, and exhibit different heparin proteoglycan and extracellular matrix binding properties. $VEGF_{165}$ is the predominant secreted isoform and has limited heparin-binding activity; $VEGF_{121}$ is freely soluble and is devoid of heparin-binding activity.

It is also known that VEGF binds to receptor systems to exert its physiological and pharmacological effects. These receptors include the three different VEGF receptor kinases, termed vascular endothelial growth factor receptor-1 (VEGFR-1)/fms-like tyrosine kinase, vascular endothelial growth factor receptor-2 (VEGFR-2)/fetal liver kinase (flk-1)/KDR, vascular endothelial growth factor receptor-3 (VEGFR-3)/fms-like tyrosine kinase 4, as well as the non-kinase receptors Neuropilin-1 (NP-1) and Neuropilin-2 (NP-2). NP-1 and NP-2 receptors are known to bind $VEGF_{165}$ and Placental Growth Factor-2 (PlGF-2), but do not bind either $VEGF_{121}$ or the non-heparin binding Placental Growth Factor-1 (PlGF-1). NP-1 and NP-2 also bind various semaphorin ligands to mediate repulsive guidance activity in certain neuronal populations.

The ability of $VEGF_{165}$ to bind to VEGFR-2 in the presence of NP-1 occurs through a VEGFR-2 co-receptor complex with NP-1 (VEGFR-2/NP-1). This is likely responsible for the increased potency of $VEGF_{165}$ versus $VEGF_{121}$ in endothelial cells co-expressing VEGFR-2 and NP-1, since the binding affinity of $VEGF_{165}$ and $VEGF_{121}$ is identical at VEGFR-2, and since $VEGF_{165}$ has access to the complex, while $VEGF_{121}$ has limited binding to the complex.

While the role of VEGFR-1 is unclear, the role of VEGFR-2 is well established as required for both vasculogenesis and angiogenesis. Hence, compounds that are capable of interacting with VEGFR-2 as receptor agonists have the potential to act as angiogenic agents, and would be useful for the treatment of diseases such as cardiac ischemia and peripheral vascular disease in which new blood vessel formation needs to be stimulated. Compounds that are capable of interacting with VEGFR-2 as receptor antagonists have the potential to act as anti-angiogenic agents, and would be useful for the treatment of diseases in which dysregulated angiogenesis is a characteristic pathology. Identification of such compounds, and methods of using these compounds, are thus desirable.

SUMMARY OF THE INVENTION

The inventive compounds are peptides that bind to VEGFR-2 in complex with NP-1 (VEGFR-2/NP-1), and also bind to the NP-1 receptor alone. Linear peptides have the general amino acid sequence $X_{(0-3)}BaBaXBBBXBX-BPX_{(0-7)}XXXPBB$ where B represents a basic amino acid, a represents an aliphatic amino acid, P is proline, X is a non-critical amino acid, and X* is any amino acid with a basic amino acid preferred. Cyclic peptides may have the general amino acid sequence $CBaBaX*BCBXBXBPX_{(0-7)}XXXPBB$ where B represents a basic amino acid, a represents an aliphatic amino acid, P is proline, C is cysteine, X is a non-critical amino acid, and X* is any amino acid with a basic amino acid preferred. Other cyclic sequences are also disclosed. Cyclic structures are formed by disulfide bonds connecting two cysteine residues. In either linear or cyclic forms, the amino acids may be naturally occurring, synthetic, or modified.

The inventive peptides function as antagonists of VEGFR-2 receptor activation by selective $VEGF_{165}$-mediated, versus $VEGF_{121}$-mediated, VEGFR-2 receptor activation. The inventive peptides specifically interfere with the binding of $VEGF_{165}$ to NP-1, and in so doing, interfere with signaling specifically through the VEGFR-2/NP-1 co-receptor complex. This specificity for binding to the VEGFR-2/NP-1 complex, as opposed to binding to VEGFR-2 alone, provides an advantage of specific inhibition; it targets sites where the combination of VEGFR-2 and NP-1 is up-regulated, or where $VEGF_{165}$ activity is increased such as in pathological activity (e.g., tumor growth and metastases, rheumatoid arthritis, endometriosis, psoriasis, proliferative retinopathy, and atherosclerosis), while not affecting sites where VEGFR-2 expression overwhelms that of NP-1, or where $VEGF_{165}$ or $VEGF_{121}$ signaling occurs solely through VEGFR-2, such as in normal tissues where angiogenesis is not occurring or during physiological angiogenesis (e.g., the female reproductive cycle, longitudinal bone growth, endochondral bone formation, and wound healing). Such specificity is useful to avoid side effects that may result from antagonism of VEGFR-2 where it is not desired, such as in quiescent endothelium where VEGF may provide a maintenance role, and also avoids the disadvantage of general inhibition of VEGF signaling, which may impair normal physiological angiogenic processes.

In various embodiments, the invention is directed to a peptide capable of binding to NP-1 or a VEGFR-2/NP-1 complex. The peptide has the general amino acid sequence previously described, or a specific disclosed sequence.

The invention is also directed to a peptide antagonist of $VEGF_{165}$ mediated VEGF-2 receptor activation, where the inventive peptide has the general amino acid sequence as described above for a linear or a cyclic form, or a specific disclosed sequence.

The invention is also directed to a method for identifying NP-1 or a VEGFR-2/NP-1 complex in a biological system. In the method, a linear or cyclic peptide has the general amino acid sequence as described above, or a specific disclosed sequence, and is capable of binding to NP-1 or a VEGFR-2/NP-1 complex. The peptide is added to the system, and binding of the peptide to NP-1 or the VEGFR-2/

NP-1 complex is identified, e.g., by labeling the peptide with a detectable label. The peptide may be added to an in vivo system or an in vitro system.

The invention is also directed to a pharmaceutical composition containing a linear or cyclic peptide having the general structure previously described or a specific disclosed sequence, and in an effective amount for modulating a function of NP-1 or a VEGFR-2/NP-1 complex, and a pharmaceutically acceptable excipient.

The invention is also directed to a method for modulating angiogenesis in an animal by administering an effective amount of a linear or cyclic peptide having the general structure previously described or a specific disclosed sequence. The peptide binds to NP-1 or a VEGFR-2/NP-1 complex and modulates angiogenesis.

The invention is also directed to a complex formed by the interaction of NP-1 and a linear or cyclic peptide having the general structure previously described or a specific disclosed sequence.

The invention is also directed to a complex formed by the interaction of a VEGFR-2/NP-1 complex and a linear or cyclic peptide having the general structure previously described or a specific disclosed sequence.

The invention is also directed to a method to antagonize a VEGFR-2 mediated function in cells expressing VEGFR-2/NP-1. A peptide having the general structure previously described or a specific disclosed sequence, and capable of binding to the VEGFR-2/NP-1 is provided, and antagonizes a VEGFR-2 mediated function such as angiogenesis.

The invention will be further appreciated in light of the following drawings and detailed description.

BRIEF DESCRIPTION OF THE DRAWINGS

FIG. 6 is the amino acid sequence of the peptides of origin and the corresponding sequence of two inventive peptides in the region of origin.

FIGS. 9A–B are graphs of results showing competition by various peptides for binding of radiolabeled $VEGF_{165}$ in HUVEC (FIG. 9A) and COS-1 cells (FIG. 9B), and FIG. 9C shows the $IC_{50}$ results.

DETAILED DESCRIPTION

Figure 1B:
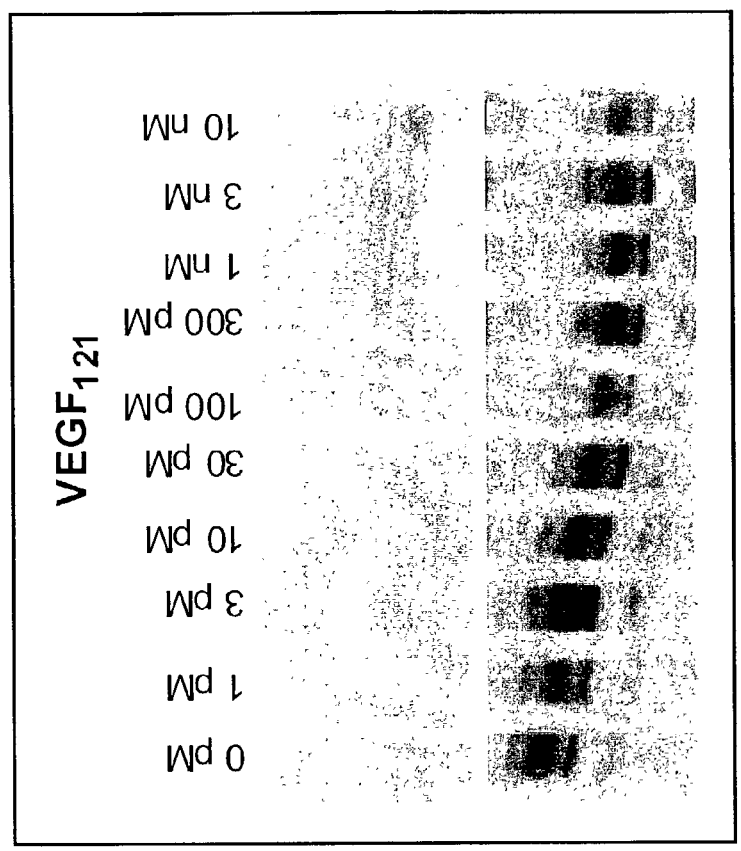
FIGS. 1A and 1B show potencies of $VEGF_{165}$ (FIG. 1A) and $VEGF_{121}$ (FIG. 1B) in activation of the VEGFR-2 receptor.

The inventive peptides, which bind to vascular endothelial growth factor receptor-2 (VEGFR-2) in complex with the Neuropilin-1 (NP-1) receptor (VEGFR-2/NP-1) and to the NP-1 receptor alone, can modulate conditions or diseases involving vascularization. These include, for example, neoplastic diseases (tumor growth and metastasis (cancer)), arthritis including rheumatoid arthritis, gynecologic diseases (e.g., endometriosis, dysfunctional uterine bleeding, ovarian hyperstimulation syndrome, preeclampsia during pregnancy, carcinomas of the ovary, endometrium, and cervix), cardiovascular disease (e.g., atherosclerosis, therapeutic angiogenesis in ischemic vascular disease), wound healing, vascular permeability, Crohn's disease, chronic cystitis, diseases of ocular neovascularization (e.g., age-related macular degeneration, diabetic retinopathy, retinopathy of prematurity, proliferative retinopathy, endogenous angiogenesis inhibitors in the eye), dermatologic diseases (e.g., infantile hemangiomas, verruca vulgaris, psoriasis, basal cell and squamous cell carcinomas, cutaneous melanoma, Kaposi's sarcoma, neurofibromatosis, recessive dystrophic epidermolysis bullosa), benign prostatic hypertrophy, etc.

The inventive peptides are derived from a combination of amino acids from Exon 6 of placental growth factor (PlGF), coupled at the carboxyl terminus to either Exon 8 of vascular endothelial growth factor isoform 165 ($VEGF_{165}$), referred to as P6V8, or Exon 7 of PlGF, referred to as P6P7. The first 16 amino acids of the 22 amino acid PlGF Exon 6 are RRP KGR GKR RRE KQR P, referred to as SEQ ID NO:1. The sequence of Exon 8 of $VEGF_{165}$ is RPCDKPRR, referred to as SEQ ID NO:2. The sequence of Exon 7 of PlGF is RPDAVPRR, referred to as SEQ ID NO:3.

The sequence of P6V8 is RRP KGR GKR RRE KQR P CDKPRR, referred to as SEQ ID NO:4. In this sequence, the minimum amino acid sequence from V8 is CDKPRR (SEQ ID NO; 54); however, C may be changed to S so that the sequence from V8 may also be SDKPRR (SEQ ID NO: 55), in which case the sequence is RRP KGR GKR RRE KQR P SDKPRR, referred to as SEQ ID NO:5. The addition of VEGF165 Exon 8 enhances both binding affinity and antagonistic activity relative to PlGF Exon 6 peptide alone. Similarly, the carboxy-terminal six amino acids from Exon 7 of PlGF can be coupled at the C-terminus of the Exon 6 peptide. In this sequence, the minimum amino acids from P7 are DAVPRR, yielding the sequence RRP KGR GKR RRE KQR P DAV PRR, referred to as SEQ ID NO:7.

Cyclic versions of the inventive peptides are also disclosed. The sequence of P6P7C is RRP KGR GKR RRE KQR P TDCHLCG DAVPRR, referred to as SEQ ID NO:6, a cyclic peptide in which a disulfide bond connects two cysteines at residues 19 and 22, shown as

RPRKRGGKRRREKQRPTDCHLCGDAVPRR.

Two cyclic peptides from P6V8 are as follows: KGR GKR RRC KQR P SDC PRR, referred to as SEQ ID NO:8 in which a disulfide bond connects two cysteines at residues 9 and 16, shown as

KGRGKRRRCKQRPSDCPRR, and KGR GKR RRE CQR P SCKPRR, referred to as SEQ ID NO:9 in which a disulfide bond connects two cysteines at residues 10 and 15, shown as

KGRGKRRRECQRPSCKPRR

The following generic sequences were generated for the inventive peptides. For a linear peptide, the sequence may be represented as $X_{(0-3)}BaBaXBBBXBXBPX_{(0-7)}XXXPBB$ SEQ ID NO:10 and for a cyclic peptide, the sequence may be represented as

$CBaBaX*BCBXBXBPX_{(0-7)}XXXPBB$

SEQ ID NO:11. In SEQ ID NOS:10 and 11, B represents a basic amino acid, a represents an aliphatic amino acid, P is proline, C is cysteine, X is a non-critical amino acid, that is, it can be substituted either with residues in the same structural family or by any amino acid, and X* is any amino acid with a basic amino acid preferred. Other cyclic sequences are also disclosed.

Variants are possible, as described. The amino acids may be naturally occurring, or may be modified. For example, the aliphatic amino acids may be norleucine, norvaline, Abu, Aib, tLeu, Cha, homoCha, homoleucine, and the basic amino acids may be Dab, Dao, Dap, Orn. The basic amino acid represented as B is either naturally occurring or is not naturally occurring, for example, K, R, H, Dab, Dao, Dap, and Orn; and the aliphatic amino acid represented as a is either naturally occurring or is not naturally occurring, for example, G, A, L, I, M, V, Nle, Nva, Abu, Aib, tLeu, Cha, homoCha, homoLeu.

The inventive peptides are highly basic in nature, having multiple lysine (K), arginine (R), and/or histidine (H) amino acids. These peptides did not act as a detergent and lyse red blood cells when tested for their lytic activity in a sheep red blood cell lysis assay at a final concentration of 100 μM. None of the peptides tested were determined to be lytic (data not shown).

The peptides may be produced by recombinant technology or by synthetic means, as is known to one of skill in this art. They may be administered systemically or locally using enteral or parenteral means known to one of skill in the art, for example, intravascular, intrathecal, epidural, intramuscular, transdermal, intraperitoneal, subcutaneous, sublingual, rectal, nasal, pulmonary, and oral means.

In use, the inventive peptides may be used for therapy and/or prophylaxis of angiogenesis or vasculogenesis as antagonists of VEGFR-2/NP-1, or NP-1. They may also be used as research tools to validate the role of the VEGFR-2/NP-1 receptor complex in both pathological and physiological angiogenesis. They may further be used to provide the basis for design of peptidomimetics that will specifically target the VEGFR-2/NP-1 complex in pathological angiogenesis.

We have previously demonstrated that the presence of NP-1 in a co-receptor complex with VEGFR-2 is sufficient to separate the potency of $VEGF_{165}$ from $VEGF_{121}$ for stimulation of VEGFR-2, even though these two VEGF isoforms exhibit similar binding affinity at VEGFR-2 (J. Biol. Chem. 2001; 276(27):25520–31, which is expressly incorporated by reference herein in its entirety). The inventive peptides provide the basis for design of peptidomimetics that specifically target the VEGFR-2/NP-1 complex in settings of pathological angiogenesis, where it can be demonstrated that co-expression of these receptors correlates with that of the $VEGF_{165}$ isoform, and is concomitant with increased vascular density.

There are other examples of peptides that behave as antagonists of VEGF signaling by interfering with the binding of $VEGF_{165}$ to VEGFR-2. These agents are usually derived from sequences in the VEGFR-2 receptor itself or bind directly to VEGF at the receptor binding site. Screening for peptides that bind to a neutralizing VEGF antibody has also identified a small peptide antagonist. This peptide antagonist was later determined to compete for binding of $VEGF_{165}$ to VEGFR-2, most probably because the peptide mimicked the receptor-binding site at a critical surface of the $VEGF_{165}$ ligand.

The only other peptide agent described to bind directly to VEGFR-2 is a basic peptide derived from HIV-Tat protein, and this peptide behaves either as a VEGFR-2 agonist or a non-specific antagonist of endothelial cell function, depending upon the assay system used, not as a specific antagonist of $VEGF_{165}$ signaling through VEGFR-2. Hence, the inventive peptides are unique chemical entities which behave as antagonists of $VEGF_{165}$ signaling through a mechanism that involves competition with $VEGF_{165}$ for binding at NP-1 and/or the VEGFR-2/NP-1 complex.

In one embodiment, the peptides are based on a combination of basic residues contained within Exon 6 of PIGF and Exon 8 of $VEGF_{165}$. Since the binding of $VEGF_{165}$ and PIGF-2 to NP-1 is a heparin-dependent process, and since the peptide sequences are derived from a portion of the heparin-binding region of PIGF-2, it is possible the inventive peptides interfere with the binding of $VEGF_{165}$ to heparin, and thereby affect binding to NP-1 and/or the VEGFR-2/NP-1 receptor complex.

Assessment of peptide binding at the different components of the VEGFR-2/NP-1 receptor complex using an affinity labeling/IP assay showed that the peptides competed for $VEGF_{165}$ binding at both the VEGFR-2 band and the NP-1 band (FIG. 10 and data not shown), whereas the peptides did not bind VEGFR-2 with high affinity when VEGFR-2 was overexpressed in the absence of NP-1 (Tables 3–10). One potential explanation is that the competition for binding measured at the VEGFR-2 band in the affinity labeling/IP experimental design represents binding to VEGFR-2 which is present in a complex with NP-1. Other explanations are possible, however, and the invention is not limited in any way to a particular explanation.

Figures 8A, 8B:
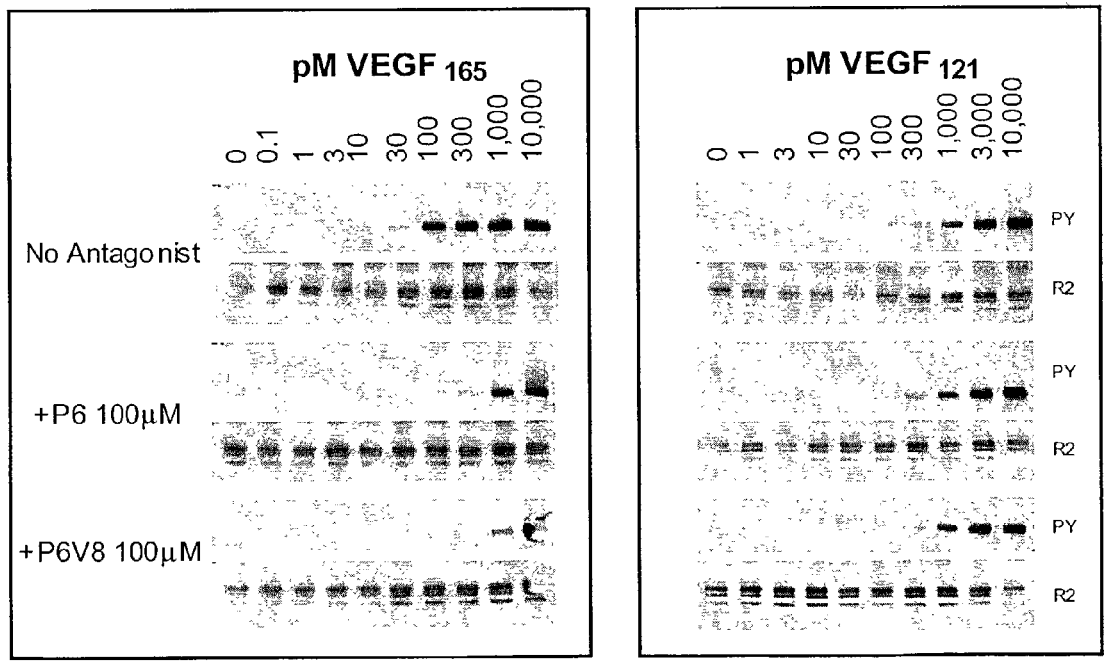
FIGS. 8A–B show antagonistic potency of various peptides on $VEGF_{165}$ (FIG. 8A) and $VEGF_{121}$ (FIG. 8B).
Figure 12:
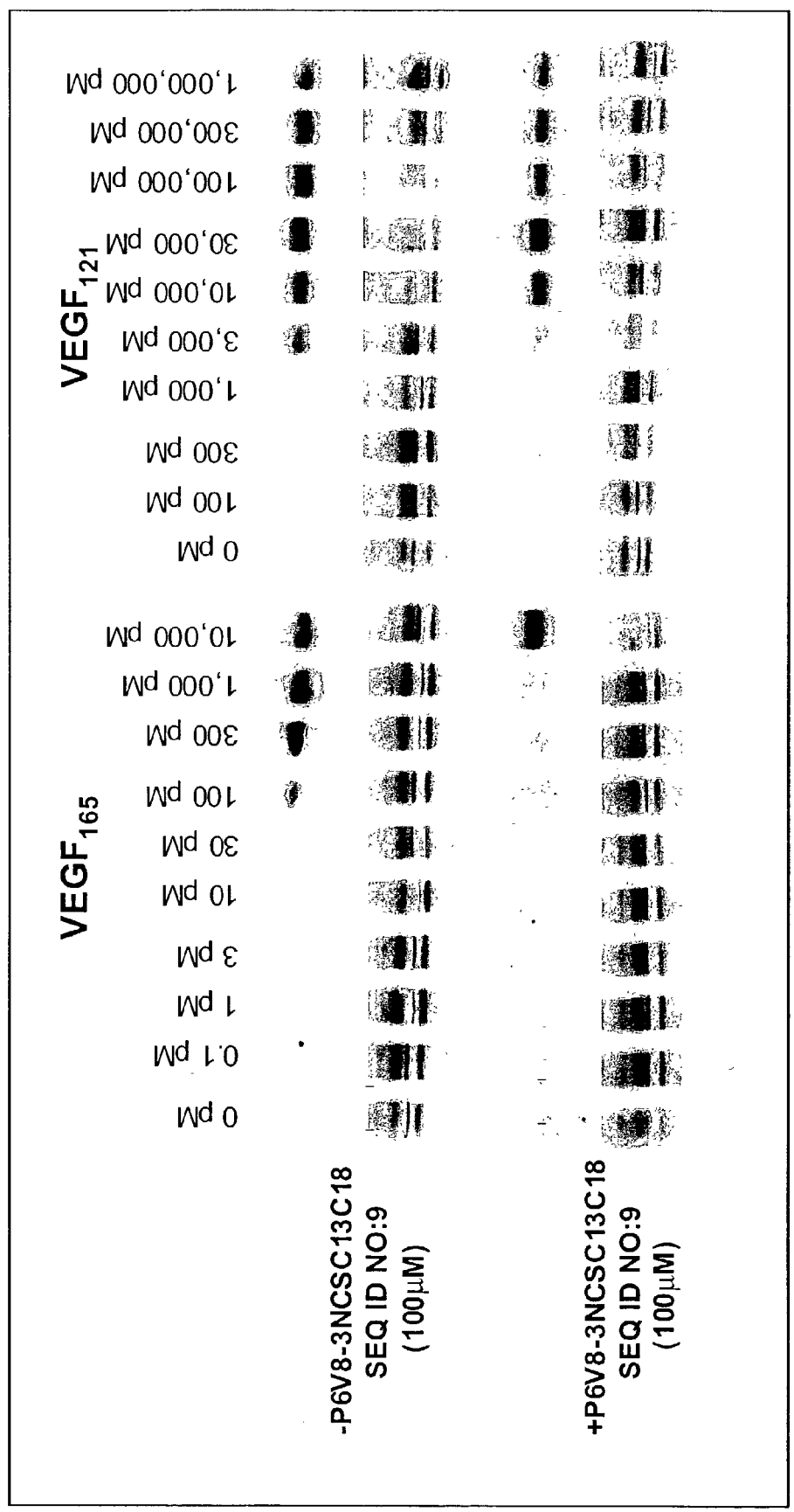
FIG. 12 shows the effect of a peptide that lacks substantial binding to VEGFR-2 on antagonism of the activation of VEGFR-2 in response to $VEGF_{165}$ versus $VEGF_{121}$.

Similarly, as reported in Soker et al., *J. Biol. Chem.* 1997; 272(50):31582–8, a GST-Exon 7–8 fusion protein derived from $VEGF_{165}$ also competes for binding at VEGFR-2 in cells co-expressing VEGFR-2 with NP-1, and does not compete for binding at the whole cell level in cells overexpressing only VEGFR-2; the authors of that report speculate that binding to VEGFR-2 in the affinity labeling experiment is affected indirectly as a result of competition for binding at NP-1. The reported GST-Exon 7–8 protein antagonizes signaling of both $VEGF_{165}$ and $VEGF_{121}$, whereas the inventive peptides only antagonize the ability of $VEGF_{165}$ to signal through VEGFR-2 (FIG. 8, FIG. 12, and Table 11). It is possible that the GST-Exon 7-8 protein is misfolded, since the results of the deletion analysis on the activity of this fusion protein are inconsistent with the known structure of this portion of the $VEGF_{165}$ molecule. Hence, it cannot be ruled out that the ability of the GST-Exon 7–8 protein to antagonize signaling through VEGFR-2 is not due to a direct interaction at VEGFR-2, whereas the inventive peptides antagonize function directly at the VEGFR-2/NP-1 complex.

While it could be postulated that antagonism of only a subset of VEGF receptors would be insufficient to attenuate signaling in settings of pathological angiogenesis, it is interesting that tumors engineered to produce only the $VEGF_{121}$ isoform are insufficiently vascularized, and do not grow to the extent observed with tumors expressing only the $VEGF_{165}$ isoform. Hence, interference of signaling through the VEGFR-2/NP-1 complex may indeed be sufficient to attenuate tumor growth, and one would anticipate that a "complex-selective" antagonist would not inhibit signaling through VEGFR-2 in cells which are not overexpressing NP-1 in concert with VEGFR-2. There is a concurrent up-regulation of VEGFR-2 and NP-1 with the $VEGF_{165}$ isoform in human patients with diabetic retinopathy or rheumatoid arthritis, with the co-expression of VEGFR-2 and NP-1 correlating with increased vascular density.

An added advantage of peptides that specifically target the VEGFR-2/NP-1 complex is the expectation of a lack of interference with the semaphorin signaling pathway. The secreted semaphorins use NP-1 as a co-receptor in a complex with either Plexins or L1-CAM, and $VEGF_{165}$ and Sema 3A appear to compete for binding at the same or a closely related site in the B-domain region of NP-1. As will be described, data with the NP-1-selective peptide AS-4 suggest that the site of action of these peptides is not NP-1 but is indeed the VEGFR-2/NP-1 complex (Table 9 and FIG. 14). However, we are aware of no peptide that is selective for the VEGFR-2/NP-1 complex, while also exhibiting higher affinity at the complex than any of the non-selective peptides, that has been identified. Thus, there is no definitive pinpointing of the VEGFR-2/NP-1 complex as the site of action for these antagonistic ligands.

In contrast to these other peptide reagents, and while not being bound by any specific theory, it is believed that the inventive peptides act by interfering with binding to NP-1 or to the VEGFR-2/NP-1 complex by direct binding to either NP-1 or the complex, rather than by direct binding to the $VEGF_{165}$ ligand. This is because the sequences of these peptides are derived from a portion of the sequence of the Exon 6 region of PlGF, which is the exon required for binding to both heparin and NP-1. Furthermore, unlike other agents that bind directly to $VEGF_{165}$ at the Exon 7 region responsible for binding to NP-1, these peptides do not interfere with binding to VEGFR-1 in isolation. Thus, the ability of these peptides to interfere with binding to NP-1 or to the VEGFR-2/NP-1 complex is likely not due to an obscuring of the receptor binding site on the $VEGF_{165}$ ligand, rather, it is likely that the peptides compete for $VEGF_{165}$ binding directly at the NP-1 or VEGFR-2/NP-1 receptor(s). This interference may be sufficient to attenuate vessel growth, and would also provide an additional advantage in that it would not interfere with the semaphorin signaling pathway, which uses NP-1 as a co-receptor in a complex with other compounds.

The invention will be further appreciated in view of the following experimental methods and results.

The following abbreviations are used throughout the specification.

| | |
|---|---|
| Ac: | acetyl [—C(O)CH$_3$] |
| Atc: | (D,L)-2-aminotetraline-2-carboxylic acid |
| Aun: | aminoundecanoic acid |
| Bc: | butanoyl [—C(O)(CH$_2$)$_2$CH$_3$] |
| Boc: | tert-butyloxycarbonyl |
| DCM: | dichloromethane |
| DEA: | diethylamine |
| DMF: | N,N-dimethylformamide |
| DMAP: | 4-dimethylaminopyridine |
| DME: | 1,2-dimethoxyethane |
| DIEA: | diisopropylethylamine |
| DPPA: | diphenylphosphoryl azide |
| EtOAc: | ethyl acetate |
| Et$_2$O: | diethyl ether |
| EDT: | ethanedithiol |
| EDCI: | 1-ethyl-3-(3'-dimethylaminopropyl)carbodiimide hydrochloride |
| Fmoc: | 9-Fluorenylmethoxycarbonyl |
| HOBt: | N-hydroxybenzotriazole, monohydrate |
| HOAt: | 1-hydroxy-7-azabenzotriazole |
| i-PrOH: | 2-propanol |
| MeOH: | methanol |
| NMM: | N-methylmorpholine |
| OtBu: | tert-butoxy [—O—C(CH$_3$)$_3$] |
| Pbf: | 2,2,4,6,7-pentamethyl-dihydrobenzofurane-5-sulfony- |
| Pmc: | 2,2,5,7,8-pentamethyl-6-chromansulfonyl- |
| p-TSA: | p-toluenesulfonate |
| PyBOP: | benzotriazole-1yl-oxy-tris-pyrrolidinophosphonium hexafluorophosphate |
| PyBroP: | bromo-tris-pyrrolidino-phosphonium hexafluorophosphate |
| tBu: | tert-butyt [—C(CH$_3$)$_3$] |
| TEA: | triethylamine |
| TFA: | trifluoroacetic acid |
| THF: | tetrahydrofuran |
| Reagent K: | 82.5% TEA/5% phenol/5% water/5% thioanisote/2.5% EDT |
| NH$_4$HCO$_3$: | ammonium bicarbonate |

Methods

Iodination of $VEGF_{165}$

Five micrograms of carrier-free human recombinant $VEGF_{165}$ (R&D Systems Inc.) is suspended in 90 μl of DPBS (Gibco) in a reaction tube (1.7 ml pre-lubricated tube, VWR). To the reaction tube, 1 mCi of $NaI^{125}$ (Amersham) is added, followed by the addition of 40 μl of chloramine T (1 μg/μl in 0.5 M sodium phosphate buffer pH 7.5, Sigma). After a one minute incubation, 50 μl of sodium metabisulfite (2 μg/μl in sodium phosphate buffer pH 7.5, Fisher Scientific) is added to the reaction tube. The reaction product is then diluted with 500 μl of column elution buffer (0.5% BSA, Sigma; 0.01% Tween 20, Sigma; DPBS, Gibco) and the reaction tube contents are transferred to a PD-10 column (Pharmacia) that had been pre-equilibrated with 6×5 mls of column elution buffer. An additional 500 µl is placed on the column prior to moving the column to the next fraction collection tube. A total of ten fractions are collected in PPG-coated 12×75 mm polystyrene test tubes (Aldrich). The fractions with the highest counts are then collected and pooled for use. The specific activity is determined by correcting for column recovery, determined empirically for each batch of columns purchased.

Transient Expression of Receptors in COS-1 Cells

To perform hNeuropilin-1 (hNP-1) and hVEGFR-2 complex formation and peptide blocking experiments, the hVEGFR-2 and hNP-1 cDNAs are cloned into the pJFE14 mammalian expression plasmid (Regeneron Pharmaceuticals) containing the SRα promoter. COS-1 cells are transiently transfected with pJFE14 (Regeneron Pharmaceuticals), hVEGFR-2 (Regeneron Pharmaceuticals), or hNP-1 (Procter & Gamble Pharmaceuticals) expression plasmids using the Lipofectamine-2000 system (Gibco-BRL). Briefly, the COS-1 cells are cultured in growth medium (DMEM, Gibco-BRL), 10% FBS (Hyclone Laboratories), 1% L-glutamine (Gibco-BRL), 1% antimycotics (Gibco-BRL), 1% non-essential amino acids (Gibco-BRL) to be 60–80% confluent on the day of transfection, with a total of 7.0 µg of plasmid/T-175 flask being transfected into the COS-1 cells by using the Lipofectamine-2000 liposomal technology in Optimem I (Gibco-BRL) according to the manufacturer's instructions. When co-expressing VEGFR-2 and NP-1, 5 µg of VEGFR-2 cDNA and 2 µg of NP-1 cDNA are used. When the receptors are expressed in isolation, for VEGFR-2, 5 µg of VEGFR-2 cDNA and 2 µg of mock vector cDNA are used.

After generation of the liposome/DNA solution, the cells are rinsed one time with 5 ml Optimem I, then replaced with another 5 ml of Optimem I containing the liposome/DNA solution. The cells are incubated for two to four hours at 37° C., 5% $CO_2$, then 5 ml of COS-1 cell growth medium is applied and the transfection is allowed to proceed overnight. The following day, cells are trypsinized (0.2% trypsin, 1 mM EDTA, Gibco-BRL), and cells containing common transfectants are pooled. Cells are then plated, using growth medium, at a density of $3 \times 10^6$ cells/100 mm dish for affinity-labeling experiments, and cultured overnight at 37° C., 5% $CO_2$. The cells are then used for corresponding VEGFR-2/NP-1 complex formation and peptide blocking studies.

Stable Expression of Receptors in Balb/C 3T3 A31 Cells

Plasmid Construction hVEGFR-2/GFP constructs are created using the Nolan Lab (Dept. of Molecular Pharmacology, Stanford University Phoenix cell retrovirus vectors from the pBMN-Z family of vectors. Additional bi-cistronic constructs were generated to contain green fluorescent protein (GFP) or GFP+hVEGFR-2 containing an EMCV IRES upstream of the GFP marker and downstream of the hVEGFR-2 gene (Regeneron Pharmaceuticals).

The hNeuropilin-1 gene is generated by PCR using oligonucleotides (Forward: 5'TATATCTAGAATGG AGAGGGGGCTGCCGCTCCTCT (SEQ ID NO:56), Reverse: 5'AGCGCTCTGCAGACCAGTTG GTGCTAT (SEQ ID NO:57) and Forward: 5'CCAGGAAUCTCATGC-CTCCGAATAAGTAC (SEQ ID NO:57), Reverse: 5'TGGTCTGCAGAGCGCTCCCGCCTGAACTAC) (SEQ ID NO:58) via RT-PCR from 1.0 Fg human heart polyA+ RNA (Clontech), and the PCR products are assembled into the pJFE14 vector. The hNP-1 gene is excised from the shuttle vector and cloned into the neomycin containing vector, pBMN-Z-I-Neo (Nolan Lab), upstream of the EMCV IRES.

Stable Expression of Receptors in Balb/C 3T3 A31 Cells

Balb/C 3T3 A31 VEGFR-2, NP-1, and VEGFR-2/NP1 stable cells are created using the Nolan Lab Phoenix Retroviral system, previously described.

Creation of hVEGFR-2 and Mock GFP Stable Cells

To generate hVEGFR-2 and Mock GFP stable cells, ecotrophic retrovirus is generated in the QMXE human epithelial packaging cells (Nolan Lab, Dept. of Molecular Pharmacology, Stanford University. QMXE human epithelial packaging cells were plated to be 70–80% confluent on the day of transfection in a T-75 flask containing QMXE growth medium (DMEM, Gibco-BRL, 10% EBS, 1% L-glutamine, Gibco-BRL), 1% antimycotics (Gibco-BRL), 1% non-essential amino acids (Gibco-BRL). QMXE cells are transfected with 4.0 Fg of the pLTRhFLK1full IRES GFP (hVEGFR-2) plasmid (Regeneron Pharmaceuticals) or the pLTRMCS IRES GEP (Mock) plasmid (Regeneron Pharmaceuticals) using the Lipofectamine-2000 system (Gibco-BRL). The liposomes containing plasmid DNA are created in Optimem I medium according to manufacturer's instructions. After the liposomes containing plasmid DNA are generated, the growth medium from the QMXE cells is removed and the cells are washed one time with 5 ml of Optimem I medium. The medium is then replaced with 5 ml of Optimem I containing the liposome-plasmid DNA mixture and incubated for five hours at 37EC, 5% CO2. After incubation, 5 ml of QMXE growth medium is added to the existing transfection medium and is incubated overnight at 37EC, 5% CO2. The transfection medium is replaced with 10 ml fresh QMXE medium and incubated at 33EC, 5% CO2 overnight to generate the desired virus. The supernatant containing virus is removed from the QMXE cells and filtered (0.4 FM filter) to remove cell debris.

Balb/C 3T3 A31 cells (ATCC, Cat#CCL-163) are plated at a density of 500,000 cells/100 mm dish one day prior to infection with virus in Balb/C growth medium (DMEM, 10% donor calf serum (Gibco-BRL), 1% L-glutamine, 1% antimycotics, 1% non-essential amino acids) and cultured at 37° C., 5% $CO_2$. On the day of infection, the growth medium is replaced with 5 ml of previously generated viral supernatants containing 6 µg/ml of polybrene (Cell and Molecular Technology Inc.). The infection is allowed to proceed for six hours at 37° C., 5% $CO_2$, after which 5 ml of Balb/C growth medium is added to the cells, and infection is allowed to continue overnight at 37° C., 5% $CO_2$. The following day the infection medium is replaced with fresh Balb/C growth medium and cells are allowed to expand.

FACS Sorting of Stable hVEGFR-2 Cells

Pools of infected Balb/C 3T3 A31 cells expressing hVEGFR-2 or GFP alone (Mock) are selected two times by FACS sorting using the hVEGFR-2 specific monoclonal antibody J5F4A2 (Procter & Gamble Pharmaceuticals as described in *J. Biol. Chem.* 276(27):25520–25531 (2001), which is expressly incorporated by reference herein in its entirety, for the VEGFR-2 cells, or by GFP emission for the Mock cells. Clonal populations of VEGFR-2 are generated by subjecting the FACS sorted VEGFR-2 cell pool to limiting dilution. A clonal hVEGFR-2 cell line termed D7R2 is selected for experimental studies based on its high levels of hVEGFR-2 expression by Western blot analysis. The pool of the Mock GFP expressing cells, hereinafter referred to as pGBMGH, is not subjected to limiting dilutions and thus is not a clonal population.

Creation of hNeuropilin-1 and hVEGFR-2/hNeuropilin-1 Stable Cells

Using the hNP-1 retroviral vector containing the neomycin resistance marker, hNP-1 and hVEGFR-2/hNP-1 stable cell lines are generated as follows:

Virus containing the hNP-1 gene is generated according to the procedure outlined previously using the QMXE cells. Balb/C 3T3 A31 cells or D7R2 (hVEGFR-2 containing cells) are infected with the NP-1 virus using these same procedures.

Clonal cell lines are obtained by subjecting the NP-1 infected cells to neomycin selection using Balb/C growth medium containing 1.5–2.0 mg/ml G418 (Gibco-BRL) for two weeks. Single colonies are obtained and clones are subjected to Western blot analysis to confirm stable expression of NP-1. The NP-1 clone containing the highest expression of hNP-1 (termed NP1–2) was selected for the subsequent studies. Likewise, the VEGFR-2/NP-1 clone (termed D7R2/NP1#4), exhibiting comparable expression of VEGFR-2 as the D7R2 line while expressing the highest level of NP-1, was selected for the subsequent studies.

Radioimmunoprecipitation

Cells are plated the day before experimentation at 3 million cells per 100 mm dish (VWR) in 10 ml of growth medium specific for each cell type. On the day of experimentation, the cells are pre-equilibrated at 4° C. for two hours in binding buffer (0.2% BSA, Sigma, 25 mM Hepes, Gibco, MEM, Gibco). The medium is then changed and test compounds (VEGF, peptides, etc.) and tracer (300–700 pM radiolabeled $VEGF_{165}$) are added in binding buffer containing a protease inhibitor cocktail (all from Sigma, with final concentrations given: leupeptin 10 μg/ml; antipain, 10 μg/ml; aprotinin 50 μg/ml; benzamine 100 μ/ml, soy bean trypsin inhibitor 100 μg/ml; bestatin 10 μg/ml; pepstatin 10 μg/ml; 0.3 mM PMSF), and 1 μg/ml heparin). The binding reaction is allowed to reach equilibrium for four hours at 4° C. with gentle agitation. Unbound ligand is removed by quickly washing three times with 5 ml ice cold BSA-free binding buffer (MEM, Gibco, 25 mM Hepes, Gibco). After the three quick washes, four ml of BSA-free binding buffer is placed on the cells and 40 μl of a crosslinker solution (15 mM DSG, Pierce, in DMSO, Sigma) is added for 15 minutes at 4° C. with agitation (DSG final concentration 150 μM). The crosslinker is removed with a single, ice cold, large volume wash (15 ml DPBS, Gibco). The cells are then lysed using RIP buffer (20 mM Tris HCl, pH 7.4; 100 mM NaCl; 1 mM EDTA; 10 mM NaI; 0.5% IGEPAL CA-630; 0.5% Na-deoxycholate; 1% BSA; all from Sigma). The lysate is then transferred to 1.5 ml conical tubes and centrifuged at 13,000×g to pellet the cellular debris. The supernatant is transferred to a fresh 1.5 ml conical tube, to which is added 10 μg antibody (R2.2, NP1ECD4, or C-19, as will be subsequently described), 10 μl of 10% SDS (RIP buffer is termed RIPS buffer with the addition of 0.1% SDS) (Gibco) and 100 μl of a 50:50 RIPS pre-equilibrated protein G bead slurry (Pharmacia). The precipitation tube is then incubated overnight at 4° C. on a nurator. The following morning the beads are washed three times in TNEN buffer (20 mM Tris-HCl pH 7.4; 100 mM NaCl; and 0.5% IGEPAL CA-630, all from Sigma), and heated for two minutes at 100° C. in 25 μl of 1×sample loading dye (5'-3'). The samples are then centrifuged to separate the beads from the sample buffer, and 20 μl of the sample buffer is loaded onto 6% SDS-PAGE gels (Novex). The gels are run at 35 mA for approximately 70 minutes, and then equilibrated in a drying buffer (10% acetic acid; 10% methanol, 80% $H_2O$) for 15 minutes and dried on a gel drier. The dried gels are then exposed to a phosphor screen overnight and developed using a Storm system (Molecular Dynamics).

Anti-Phosphotyrosine Assay

Human umbilical vein endothelial cells (HUVEC) are plated (1×10$^6$ cells/flask) in T75 flasks (VWR) one week prior to stimulation. On the day of stimulation, the cells are rinsed twice with 10 ml of DMEM (Gibco) and serum-starved in the same medium for 60 to 120 minutes at 37° C. The cells are stimulated by adding increasing concentrations of human recombinant $VEGF_{165}$ purchased from R&D Systems (R&D Systems Inc. Cat# 293-VE-005 CF) in 1.5 ml of binding buffer (DMEM, Gibco; 25 mM Hepes, Gibco; 0.2% BSA, Sigma) containing 1 μg/ml heparin (Sigma) for five minutes at 37° C. in 5% $CO_2$. Following stimulation, the cells are aspirated and lysed in 1.25 ml RIPA buffer (20 mM Tris-HCl pH 7.6; 150 mM NaCl; 50 mM NaF; 1 mM sodium orthovanadate; 5 mM benzamidine; 0.5% IGEPAL CA-630, all from Sigma) in the presence of the protease inhibitor cocktail (previously described). The lysate is then transferred to 1.5 ml conical tubes, and then forced through a 23-gauge needle (Becton Dickinson) to complete solubilization of the sample. The cellular debris is cleared by centrifugation of the sample at 13,000×g for five minutes at 4° C., and the supernatant is transferred to a fresh 1.5 ml conical tube, to which is added 10 μg of the R2.2 antibody, 10 μl of 10% SDS (Gibco), and 100 μl of a 50:50 RIPA pre-equilibrated bead slurry (Pharmacia). The precipitation tube is then incubated overnight at 4° C. on a nurator. The following morning the beads are washed three times in the RIPA buffer, and heated for two minutes at 100° C. in 25 μl of 1× sample loading dye (5'-3'). The samples are then centrifuged to separate the beads from the sample buffer, and 20 μl of the sample buffer is loaded onto 6% SDS-PAGE gels (Novex). The gels are run at 35 mA for approximately 70 minutes, and transferred to PVDF membranes (OWL) using standard transfer techniques as known to one skilled in the art. Following transfer, the membranes are blocked in sterile filtered (0.22 μm) blocking buffer (TBS; 0.1% Tween 20; 5% BSA, all from Sigma) for 30 minutes at room temperature. The blocking buffer is removed and saved for the following day. The membranes are rinsed three times for five minutes in TBS-T 0.1% (TBS; 0.1% Tween 20; both from Sigma), and stored in the same buffer overnight at 4° C. without agitation. The membranes are then reblocked for an additional two hours in the saved blocking buffer from the previous day, and probed with 4G10 (UBI) at 0.5 μg/ml in sterile filtered primary probe buffer (TBS, 0.1% Tween 20, 2.5% BSA, all from Sigma) for two hours at room temperature with agitation. Following the primary probe, the membranes are washed six times for five minutes in TBS-T 0.1% (previously described) at room temperature with agitation. The membranes are then probed using a secondary HRP labeled anti-mouse antibody (Pierce) at 1:40,000 in 0.1% TBS-T for one hour at room temperature with agitation. The membranes are then sequentially washed using three washes for ten minutes in 0.1% TBS-T, two washes for ten minutes in 0.3% TBS-T (TBS, Sigma), 0.3% Tween 20, Sigma), and three washes for five minutes in TBS. The membranes are then developed using the ECL system (Amersham) as per the manufacturer's recommendations, and detected using the FluorS Max system (BioRad). After the images are recorded, the membranes are rehydrated with three quick rinses in TBS, and stripped in 200 mM glycine (Sigma), pH 2.8 overnight at room temperature with agitation. The following morning the membranes are reblocked, reprobed, and redeveloped as above with the substitution of the primary antibody (R2.2 antibody at 1:5,000) and its corresponding secondary antibody (HRP labeled anti-rabbit IgG at 1:40,000, Pierce).

Western Blot Analysis

Confluent cells are removed from T-175 flasks in 1 ml of detachment buffer (10 mM Tris-HCl, pH 7.4; 1 mM EDTA; 0.25 M sucrose) by gently scraping the cells loose. The cells are pelleted by centrifugation for five minutes at 13,000×g. The cell pellet is then resuspended in 80–100 µl of RIPA buffer containing protease inhibitor cocktail (previously described). The lysate is then transferred to 1.5 ml conical tubes and forced through a 23-gauge needle (Becton Dickinson) to complete solubilization of the sample. The cellular debris is cleared by centrifugation of the sample at 13,000×g for five minutes, and the supernatant is transferred to a fresh 1.5 ml conical tube. A protein determination is performed on the lysate (BCA assay kit, Pierce, as per manufacturer's specifications). Twenty µg of total cell protein is diluted into sample loading dye (5'-3') and loaded into a single lane of a 6% SDS-PAGE gel (Novex). The gels are run at 35 mA for approximately 70 minutes, and transferred to PVDF membranes (OWL) using standard transfer techniques as known to one skilled in the art. Following transfer, the membranes are blocked in sterile filtered (0.22 µm) blocking buffer (TBS; 0.1% Tween 20; 5% BSA, all from Sigma) for 30 minutes at room temperature. The blocking buffer is removed and saved for the following day. The membranes are rinsed three times for five minutes in 0.1% TBS-T (TBS, 0.1%; Tween 20, both from Sigma), and stored in the same buffer overnight at 4° C. without agitation. The membranes are then reblocked for an additional two hours in the blocking buffer saved from the previous day, and probed with the R2.2 antibody at 1:5,000 in sterile filtered primary probe buffer (0.1% TBS; Tween 20, 2.5% BSA, all from Sigma) for two hours at room temperature with agitation. Following the reaction with the primary probe, the membranes are washed six times for five minutes in 0.1% TBS-T (described above) at room temperature with agitation. The membranes are then probed using a secondary HRP labeled anti-rabbit antibody (Pierce) at 1:40,000 in 0.1% TBS-T for one hour at room temperature with agitation. The membranes are then sequentially washed using three washes for ten minutes in TBS-T 0.1%, two washes for ten minutes in TBS-T 0.3% (TBS), 0.3% Tween 20, and three washes for five minutes in TBS. The membranes are then developed using the ECL system (Amersham) as per the manufacturer's recommendations, and detected using the FluorS Max system (BioRad). When probing for Neuropilin-1, the Npn-1 #30 antibody (as will be described) is used as above, except that 0.1% TBS-T and Tween 20 with 0.5% Blotto is used both as blocking agent and primary probe buffer.

Whole Cell Binding Assay

Cells are plated the day before experimentation at 200,000 cells per well in twelve well tissue culture plates (VWR) in 1 ml of growth medium specific for each cell type. On the day of experimentation, the cells were pre-equilibrated at 4° C. for 30 to 60 minutes in binding buffer (0.2% BSA, Sigma; 25 mM Hepes, Gibco; MEM, Gibco). The medium is then changed and both the test compounds (VEGF, peptides, etc.) and tracer (100–400 pM radiolabeled VEGF$_{165}$) are added in binding buffer containing protease inhibitor cocktail (previously described) and 1 µg/ml heparin (Sigma). The binding reaction is allowed to reach equilibrium for four hours at 4° C. with gentle agitation.

Unbound ligand is then removed by quickly washing three times with 5 ml ice cold BSA-free binding buffer (MEM, Gibco, 25 mM Hepes, Gibco). Cells are lysed by the addition of 250 µl of RIPS Buffer (previously described), and the lysed cells are transferred to 12×75 mm test tubes and counted using a gamma counter. Generation of competition curves and IC$_{50}$ values are performed using the Prism software package (Graphpad Software Inc., San Diego, Calif.). For the saturation analysis, the experiment is performed as described above except that increasing concentrations of $^{125}$I-VEGF$_{165}$ are used (0.5 pM to 2580 pM), in the absence or presence of 30 nM unlabeled VEGF$_{165}$ for non-specific binding. B$_{max}$ and K$_d$ values are obtained using the Prism software package, where the optimal fit of the data is to a one binding site model for all receptors or receptor combinations tested (data not shown). All whole cell binding and saturation figures displayed represent the average of triplicate determinations.

Receptor-Specific Antibody Generation

Polyclonal Antibody Production

The Neuropilin-1 rabbit polyclonal antibody (NP1ECD4) is raised against the purified peptide sequence (Ac-D L D K K N P F I K I D F T G S T C-amide [AA: 814–8301 {SEQ ID NO: 60}], present in the extracellular region and unique to the extracellular domain of Neuropilin-1, by QCB (a division of Biosource International, Hopkinton, Mass.), as described in J. Biol. Chem. 276(27):25520–25531 (2001). As indicated, the peptide is acetylated on the amino terminus and amidated on the carboxy terminus to reduce the antigenicity of the free termini and, for antibody production, the peptide is conjugated to KLH by an added COOH terminal cysteine. Based on the sequence listed above, the NP1ECD4 antibody recognizes only the full-length protein. After harvesting from the rabbits, the serum is affinity purified by QCB (Hopkinton, Mass.) using standard affinity purification techniques, and supplied in a standard buffer (PBS without Ca2+, Mg2+, pH 7.4). This antibody does not cross-react with VEGFR-2 (data not shown), and is predicted to not cross-react with Neuropilin-2. Furthermore, this antibody recognizes Neuropilin-1 in both rodent and human species (data not shown).

The VEGFR-2 rabbit polyclonal antibody (R2.2) is raised against the purified peptide sequence Ac-S K R K S R P V S V K T F E D I P L E E P C-amide (AA: 1225–1246 [SEQ ID NO: 61]), unique to the carboxyl terminal domain of VEGFR-2, by QCB), as described in J. Biol. Chem. 276 (27):25520–25531 (2001). Again, to reduce the antigeriicity of the free termini, the peptide is acetylated on the amino terminus and amidated on the carboxy terminus. For antibody production the peptide is conjugated to KLH by the COOH terminal cysteine. After harvesting the serum from the rabbits, the serum is affinity purified by QCB using standard affinity purification techniques, and supplied in a standard buffer (PBS without Ca2+, Mg2+, pH 7.4). The VEGFR-2 antibody does not cross-react with VEGFR-1 or NP-1 (data not shown), and is predicted to not cross-react with Neuropilin-2. Furthermore, this antibody recognizes VEGFR-2 in human, mouse, rat, and bovine species (data not shown).

The Npn-1 #30 antibody is the kind gift of Dr. David Ginty, Johns Hopkins University. This antibody is generated against amino acids 583 to 856 of rat Neuropilin-1. These residues correspond to the MAM domain and the extracellular juxtamembrane region. This antibody is used exclusively for all Western blotting and some of the immunoprecipitations.

The C-19 antibody for Neuropilin-1 is purchased from Santa Cruz Biotechnology, Inc. (Santa Cruz, Calif.). This antibody is a goat anti-human NP-1, mapping to the carboxy terminus. The epitope used differs from the mouse sequence by only two amino acids. This antibody is sometimes substituted for the Npn-1 #30 antibody for immunoprecipitations only (see figure legends for specific antibodies used).

Monoclonal Antibody Production and Characterization

For generation of the immunogen for the J5F4A2 monoclonal antibody, the entire coding region of the VEGFR-2 extracellular domain (AA: 1–760) is expressed and purified from Sf9 cells as an Fc fusion protein (Regeneron Pharmaceuticals). Eight liters of baculovirus supernatants are harvested from the bioreactor, brought to 5 mM EDTA, pH 7.5 and filtered. The filtered supernatant is pumped over a 25 ml protein A (fast flow) column (Pharmacia) at a rate of 28 ml/min. The column is washed with buffer containing 0.5 M NaCl in TBS at a rate of 28 ml/min. The column is eluted with 25 mM citrate, 150 mM NaCl, pH 3.0, at 5 ml/min. Fractions containing eluted protein as determined by UV absorption are pooled and dialyzed against TBS, 10% glycerol, pH 7.5. No size exclusion chromatography is performed on the protein. A small percentage of aggregates were observed following non-reducing SDS PAGE. The N-terminal sequence of the purified protein was determined to be a single sequence (ASVGL). This protein was designated FLK-1(Ig 1–7):Fc. A similar procedure was followed for expression and purification of a variant of the VEGFR-2 extracellular domain containing only the first three Ig domains, designated FLK-1 (Ig 1–3):Fc.

The initial immunization for FLK-1 is performed by coating nitrocellulose membranes with recombinant human FLK-1(Ig 1–7):Fc protein at 10 µg/ml in 50 mM carbonate buffer, pH 9.4, overnight. The next day membranes are minced into small pieces and implanted subcutaneously into the backs of Balb/c mice with complete Freunds adjuvant. After the initial implantation, booster injections are administered at three-week intervals (total of four) without adjuvant. Four days prior to the creation of the fusion, a final boost injection is given intravenously. On the day of fusion, mouse spleen cells are fused to THT mouse myeloma cells using PEG 4000 pH 7.4. Cells are plated at 50,000 cells/well in 16–18 96 well plates with Dulbecco's medium containing high glucose, HAT (hypoxanthine/aminopterin/thymidine), 10% hybridoma cloning supplement and 1×OPI (oxalate/pyruvate/insulin). Colonies are screened by ELISA on plates coated with FLK-1(Ig 1–3):Fc, FLK-1(Ig 1–7):Fc, and Fc at 100 ng/well in carbonate buffer, pH 9.4. Cell clones reacting to one distinct protein are isotyped, expanded, cloned by limiting dilution, and frozen. Unique clones are tested by Western blot using hybridoma tissue culture supernatants and/or purified antibody. The VEGFR-2 monoclonal antibody (J5F4A2) showed the optimal reactivity to FLK-1 (Ig 1–7):Fc. Antibodies are purified from tissue culture supernatant using a Protein G column.

In the case of the J5F4A2 antibody, the antibody reacted with both FLK-1 proteins on Western blot analysis, indicating that the epitope resides in Ig domains 1–3. The antibody did not recognize the FLT-1:FLK-1 trap (which contains only Ig domain 3 of VEGFR-2) on Western blot analysis, indicating that the epitope is contained in Ig domains 1–2. The antibody is able to immunoprecipitate ligand-bound receptor, indicating that it did not recognize the ligand binding site. It did not recognize VEGFR-1.

Synthesis of the Compounds

Fmoc-amino acid derivatives are purchased from Novabiochem (San Diego Calif.). All other solvents and chemicals are of analytical grade.

Peptides are assembled by a stepwise solid-phase procedure on a preloaded-WANG resin (usually, substitution=0.574) using a Symphony synthesizer. Side-chain protecting groups of Fmoc-amino acids are Arg(pbf), Cys (trityl), Asp(tBu), Glu(tBu), His(trityl), Lys(Boc), Asn (trityl), Gln(trityl), Ser(tBu), Thr(tBu), Trp(Boc), Tyr(tBu).

Fmoc-amino acid (4 equivalents) is double coupled to peptide resin by HBTU (4 equivalents), HOBT (4 equivalents) and DIEA (8 equivalents) for two hours. The Fmoc protecting group is removed by 20% piperidine in DMF for five minutes and twenty minutes separately. The final peptide resins are cleaved and deprotected by Reagent K for four hours and the crude peptide is precipitated and washed by Et$_2$O five times. The crude peptide is analyzed by analytical HPLC (HP 1050) with a Vydax column (4.6 mm×250 mm) followed by purification by preparative HPLC to yield the purified peptide. The purified peptide is analyzed by HPLC (HP 1050) Vydax column (4.6 mm×250 mm). The mass spectral analysis is performed by Electrospray method (Perkin-Elmer API III).

Some peptides are cyclized via disulfide linkage. For example, the deprotected peptide CKGRGKRCREKQRPSDKPRR, referred to as SEQ ID NO:12 where a disulfide bond connects cysteines at residues 1 and 8 (P6V8-3NCS1-7CC), as shown

is dissolved in 40 ml of 0.5% NH$_4$HCO$_3$ pH 8. After 24 hours, no free sulfhydryl could be detected by the Ellman reagent, and the solution is acidified with acetic acid. The product is then lyophilized and purified by preparative HPLC as above. Conversely, peptides which are not cyclized via disulfide linkage demonstrated free sulfhydryl groups that could still be detected by the Ellman reagent.

Results

Functional Difference Between VEGF$_{165}$ and VEGF$_{121}$

Despite the fact that VEGF$_{165}$ and VEGF$_{121}$ have the same affinity for the isolated purified VEGFR-2 receptor protein, these two ligands have differential potencies in activation of the VEGFR-2 receptor in vitro. This difference in potency is characterized by an EC$_{50}$ for VEGF$_{165}$ of $7.69 \times 10^{-11}$ M (log EC$_{50}$=−10.11±0.113, N=14), and for VEGF$_{121}$ of $2.45 \times 10^{-9}$ M (log EC$_{50}$=−8.61±0.091, N=14), with a representative experiment illustrated in FIG. 1 using endogenous HUVEC cells.

Figure 1A:
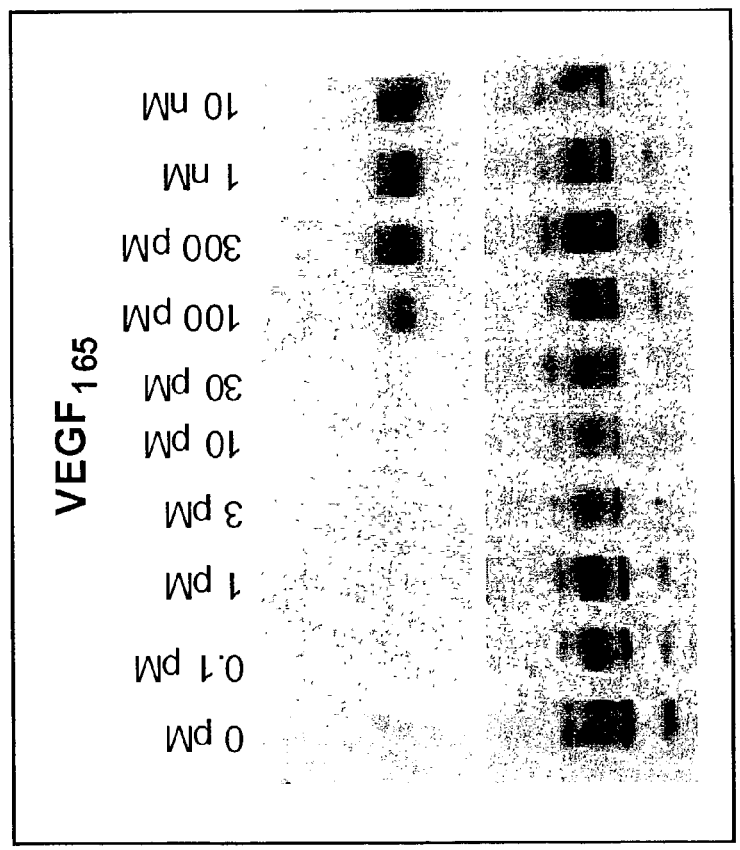

HUVEC cells are stimulated with ligand for five minutes at 37° C., lysed and immunoprecipitated with an antibody specific to VEGFR-2 (R2.2). Following SDS-PAGE separation and transfer, the blots are probed using an antiphosphotyrosine antibody (4G10, UBI) and developed using standard ECL techniques (FIGS. 1A and 1B, upper panels). These same blots were then stripped and reprobed using an antibody specific for VEGFR-2 (R2.2, FIGS. 1A and 1B, lower panels). The films were scanned and quantitated using Image Quant (Molecular Dynamics). The non-linear regression analysis (Prism, San Diego, Calif.) of the PY/R2 signal ratio yields an EC$_{50}$ of 34.9 pM and 2.09 nM for VEGF$_{165}$ and VEGF$_{121}$, respectively. The reported similarity in affinity between VEGF$_{165}$ and VEGF$_{121}$ is not an artifact of producing the protein as a receptor body (receptor extracellular domains as an isolated protein fused to an Fc, as known to one skilled in the art), because when the full-length receptor is expressed in cells, similar results are observed (FIG. 2).

Figure 2:
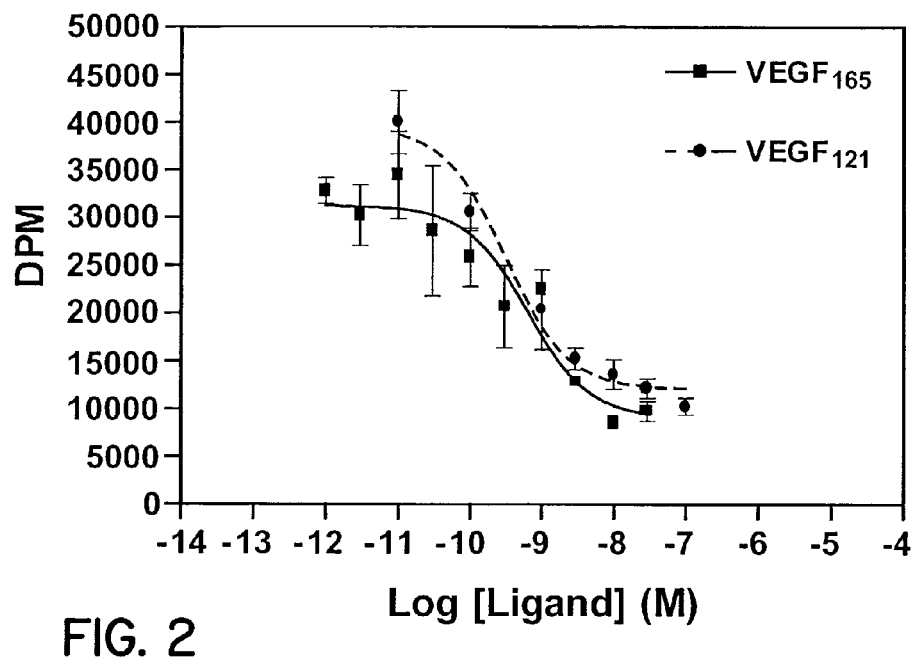
FIG. 2 is a graph of results showing the ability of $VEGF_{165}$ and $VEGF_{121}$ to compete with radiolabeled $VEGF_{165}$ binding in cells overexpressing VEGFR-2.

In FIG. 2, VEGFR-2 has been overexpressed in COS-1 cells and the ability of these two ligands to compete for $^{125}$I-VEGF$_{165}$ binding has been measured. COS-1 cells overexpressing VEGFR-2 in isolation were incubated in the presence 287 pM $^{125}$VEGF$_{165}$ and increasing concentrations of cold VEGF$_{165}$ or VEGF$_{121}$ to equilibrium (four hours) at 4° C. The cells were then rinsed three times with ice cold binding buffer to remove unbound ligand, lysed, and transferred to 12×75 mm test tubes for counting on a gamma counter. The IC$_{50}$ values were calculated by fitting the data to a four parameter logistic equation (Prism software). This experiment has been repeated twice in the COS-1:R2 cells with similar results.

In the COS-1 cells overexpressing the full-length VEGFR-2, the IC$_{50}$ values for VEGF$_{165}$ (IC$_{50}$=6.34×10$^{10}$ M) and VEGF$_{121}$ (IC$_{50}$=3.12×10$^{-10}$) binding are nearly identical, indicating that these two ligands have an identical affinity for VEGFR-2. In the absence of a difference in affinity, the difference in potency between VEGF$_{165}$ and VEGF$_{121}$ indicates that another factor must be influencing the ability of these ligands to activate VEGFR-2.

Identification of Neuropilin-1 as a VEGF Receptor

An initial explanation for the difference in potency between VEGF$_{165}$ and VEGF$_{121}$, is that VEGF$_{165}$ (with its Exon 7 heparin binding domain) could take advantage of the potential ability of heparin-sulfates to stabilize the interaction between VEGF and its signaling receptors, as had been demonstrated for the FGF receptor system. However, additional reports in the literature pointed to the existence of a 120 kDa binding protein that specifically bound VEGF$_{165}$ but not VEGF$_{121}$. The identity of this isoform-specific binding protein is later demonstrated to be identical to Neuropilin-1.

Affinity of Cells Expressing VEGFR-2, Neuropilin-1, or Co-Expressing Both VEGFR-2 and Neuropilin-1

It has been previously suggested that the increased potency of VEGF$_{165}$ versus VEGF$_{121}$ is due to the affinity of VEGF$_{165}$ being increased when VEGFR-2 is co-expressed with NP-1, whereas the affinity of VEGF$_{121}$ is not. This possibility was evaluated by determining equilibrium binding K$_d$ values in cells expressing VEGFR-2 alone, NP-1 alone, and cells co-expressing both receptors, using standard saturation analysis techniques as known to one skilled in the art. Table 1 summarizes the results.

TABLE 1

Saturation Analysis results from multiple cell lines

| Cell Line | Type | Receptors | Log K$_d$ ± SEM | K$_d$ | N |
|---|---|---|---|---|---|
| COS-1 | Transient | VEGFR-2 | −9.38 ± 0.19 | 4.18 × 10$^{−10}$ | 6 |
|  |  | VEGFR-2/NP-1 | −8.84 ± 0.00 | 1.43 × 10$^{−09}$ | 1 |
|  |  | NP-1 | −8.68 ± 0.17 | 2.09 × 10$^{−09}$ | 3 |
|  |  | Mock | −8.95 ± 0.31 | 1.11 × 10$^{−09}$ | 4 |
| Balb/c* | Stable | VEGFR-2 | −9.53 ± 0.08 | 2.91 × 10$^{−09}$ | 5 |
|  |  | VEGFR-2/NP-1 | −9.48 ± 0.33 | 3.31 × 10$^{−10}$ | 3 |
|  |  | NP-1 | −9.38 ± 0.13 | 4.17 × 10$^{−10}$ | 5 |
|  |  | Mock | −9.65 ± 0.13 | 2.22 × 10$^{−10}$ | 4 |
| HUVEC | Endothelial | VEGFR-2/NP-1 | −9.77 ± 0.12 | 1.69 × 10$^{−10}$ | 2 |

*Balb/c cells contain readily detectable levels of endogenous NP-1 as measured in Western blot analysis with the Npn-1 #30 polyclonal antibody. The cell lines are as follows: for VEGFR-2, D7R2; for VEGFR-2/NP-1, D7R/2NP-1 #4; for NP-1, NP1-2, and for mock, pGBMGH.

In the COS-1 cells the affinity is similar when either VEGFR-2 or NP-1 is expressed alone (VEGFR-2 K$^d$=4.18× 10$^{−10}$ M; NP-1 K$_d$=2.09×10$^{−09}$ M). In cells co-expressing VEGFR-2 and NP-1, there is no substantial increase in affinity, suggesting that a subpopulation of high affinity sites is not found. However, in a transient system, only a small minority of cells may actually co-express both receptors, making detection of this small population of high affinity sites even more difficult.

To circumvent this limitation, stable cell lines were created in the Balb/C 3T3 A31 cell background. The mock transfected Balb/C cells contain detectable amounts of NP-1 as evidenced by Western blot analysis (data not shown), and the binding affinity in the mock transfected cells is nearly identical to that seen when NP-1 is overexpressed on this background. When VEGFR-2 is overexpressed on this background, the formation of a higher affinity site is not observed, nor is an increase in binding affinity observed when Balb/C cells were engineered to overexpress NP-1 in concert with VEGFR-2 (see Table 1). Analysis of the K$_d$ values in the Balb/C cells using the Wilcoxon signed rank sums test did not reveal a statistically significant difference in the binding affinity between VEGFR-2, NP-1, or the combination of VEGFR-2 and NP-1 in any of the lines displayed in Table 1 (P=0.327–0.655, depending on the pair-wise comparison).

A second possible explanation for the increased potency of VEGF$_{165}$ was the formation of a complex between VEGFR-2 and another receptor component that results in increased activity of the receptor, without an increase in binding affinity. When the receptor complement present in HUVEC was examined by both Northern and Western analysis, it was determined that HUVEC used for this study contained high levels of VEGFR-2 and the newly identified VEGF receptor Neuropilin-1 (NP-1), and relatively low to undetectable expression levels of VEGFR-1 (data not shown). Based on this information, the difference in potency could be explained by the formation of a complex between VEGFR-2 and Neuropilin-1 (NP-1), and the formation of this complex was responsible for the increased potency of VEGF$_{165}$ over VEGF$_{121}$.

Complex Formation

The potential for the VEGFR-2/NP-1 complex to form was determined using a reciprocal radioimmunoprecipitation design. In this design, cells expressing each of the receptors in isolation, or co-expressing both receptors, were affinity labeled with $^{125}$I-VEGF$_{165}$, cross-linked, and immunoprecipitated with antibodies specific for one member of the suspected receptor complex. With complex formation, the receptor-specific antibody more effectively precipitates the receptor against which it was generated, and additionally precipitates a band of the appropriate size corresponding to the alternate receptor in the complex.

Figures 3A, 3B:
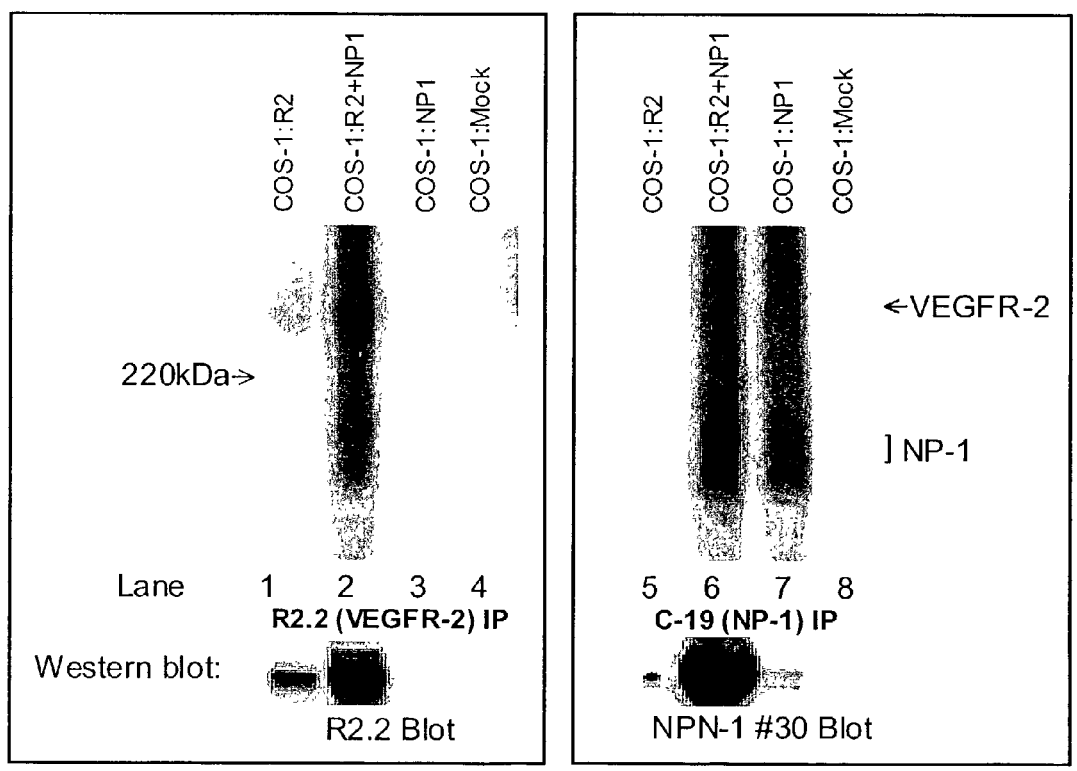
FIGS. 3A–B show formation of the VEGFR-2/NP-1 complex by SDS-PAGE (FIGS. 3A and 3B top) and Western blots (FIGS. 3A and 3B bottom) detected by antibody specific for VEGFR-2 (FIG. 3A) and antibody specific for NP-1 (FIG. 3B).

As shown in FIG. 3, the complex can form in the COS-1 overexpression system. Cells overexpressing the indicated receptors transiently (COS-1) were affinity labeled using 704 pM $^{125}$I-VEGF$_{165}$ at 4° C. for four hours. The cells were then lysed, immunoprecipitated using the receptor-specific antibody listed (for VEGFR-2, R2.2 as shown in FIG. 3A; for NP-1, C-19 as shown in FIG. 3B), separated by SDS-PAGE, and developed using the Storm system (Molecular Dynamics). As shown in FIG. 3A, the NP-1 doublet is co-precipitated with affinity labeled VEGFR-2. As shown in FIG. 3B, VEGFR-2 is co-precipitated when an NP-1 specific antibody is used. This experiment has been repeated three times with similar results. The Western blots are shown in the lower panels of FIGS. 3A–B and demonstrate the relative receptor expression level achieved. The antibodies used for blotting are R2.2 for VEGFR-2, and the Npn-1 #30 antibody for NP-1.

With reference to FIG. 3A, in cells expressing only VEGFR-2 (lane 1), a single band of approximately 240 kDa was observed. This band represents $^{125}$I-VEGF$_{165}$ crosslinked to VEGFR-2. When VEGFR-2 and NP-1 are co-expressed in COS-1 cells, not only affinity labeled VEGFR-2 is immunoprecipitated using the VEGFR-2 specific antibody, but also an additional doublet of bands that appear at the predicted size (~140 kDa) for Neuropilin-1 cross-linked to $^{125}$I-VEGF$_{165}$ (lane 2) are immunoprecipitated. In cells overexpressing only NP-1 (lane 3), the VEGFR-2 receptor was not present for the complex to form, and therefore the NP-1 doublet was not substantially detected. The data in lane 3 also indicate that the VEGFR-2 antibody does not crossreact with NP-1, and the weak doublet detected in lane 3 may indicate formation of a complex between endogenous VEGFR-2 and the exogenous NP-1. Interestingly, a weak doublet that corresponds to the size of the NP-1 bands was also detected with the VEGFR-2 receptor-specific antibody in cells overexpressing VEGFR-2, which may indicate formation of a complex between endogenous NP-1 (see bottom panel of FIG. 3B) in the presence of the exogenous VEGFR-2. The inability to detect these affinity labeled bands in the COS-1 cells expressing Mock vector (lane 4) provided further indication that these bands were not non-specific.

With reference to FIG. 3B, the identity of the lower doublet is confirmed as being NP-1 by the immunoprecipitation with the NP-1 specific antibody. The inability to detect any labeled bands in VEGFR-2 cells alone (lane 5) demonstrated that when NP-1 was not overexpressed, the complex with endogenous NP-1 and overexpressed VEGFR-2 was not detected, as no affinity labeled VEGFR-2 receptor was detected in cells immunoprecipitated by the NP-1 specific receptor antibody. Lane 5 also demonstrated that the NP-1 receptor-specific antibody did not crossreact with the VEGFR-2 receptor. When both receptors were co-expressed (lane 6) a band corresponding to the size of affinity labeled VEGFR-2, in addition to the affinity labeled NP-1 doublet, was seen. COS-1 cells expressing NP-1 alone that are immunoprecipitated with the NP-1 antibody confirm the identity of the doublet as being due to $^{125}$I-VEGF$_{165}$ binding to NP-1 (lane 7). The inability to detect the doublet in COS-1 cells expressing mock vector (lane 8) again demonstrate the specificity of the immunoprecipitated bands.

More intense labeling of either the VEGFR-2 or NP-1 bands was observed upon co-expression of the receptors (for R2, lane 2 vs. lane 1; for NP-1, lane 6 vs. lane 7). This is because co-expression resulted in increased expression of VEGFR-2 and NP-1 protein, versus that obtained when either receptor was expressed alone (bottom panel, FIG. 3), and was not due to increased binding affinity at the receptor complex (Table 1).

Figure 4:
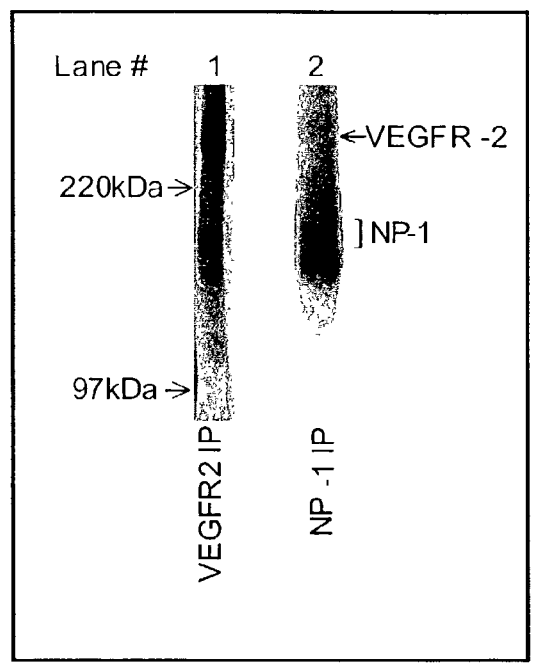
FIG. 4 shows formation of the VEGFR-2/NP-1 complex in human umbilical vein endothelial cells (HUVEC).

With reference to FIG. 4, the ability of the complex to form in endogenous cells was demonstrated. Similar results were found when the reciprocal immunoprecipitations, described above, were performed in HUVEC. Using the VEGFR-2 specific antibody, affinity labeled VEGFR-2 was immunoprecipitated along with a triplet of bands, of which two bands correspond in size to the doublet that was immunoprecipitated by the NP-1 antibody (lanes 1,2). The third band (left panel, lowest band) of the triplet observed in HUVEC might represent an endogenous soluble form of NP-1, as soluble NP-1 is competent to bind $^{125}$I-VEGF$_{165}$ and may also form a complex with VEGFR-2. This band was not observed in the COS-1 system because the NP-1 cDNA used for these experiments would only produce the full-length receptor. In the NP-1 immunoprecipitations of the endogenous HUVEC, a doublet of the correct size was once again observed (lane 2). The triplet was not observed because the NP-1 antibody used for these experiments would not be predicted to immunoprecipitate the soluble form of NP-1.

Complex Blocking Agents

Figure 5A:
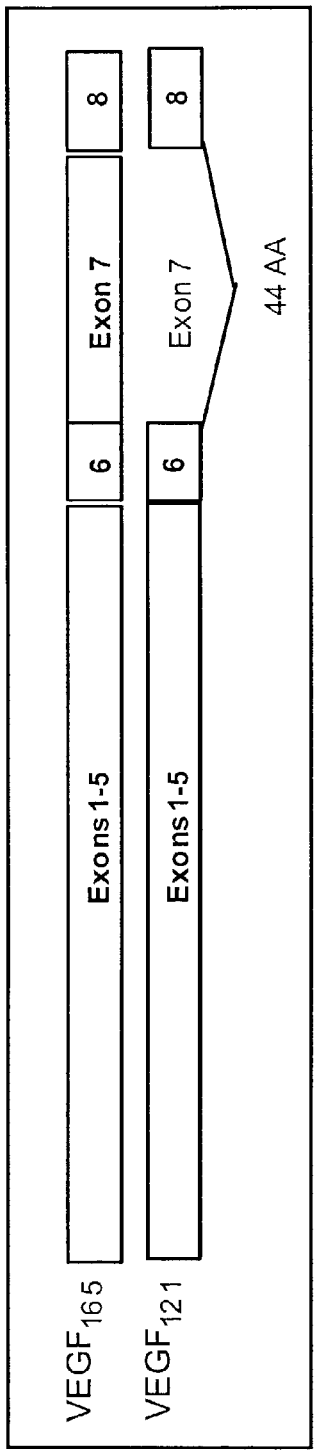
FIG. 5A illustrates the structural comparison between $VEGF_{165}$ and $VEGF_{121}$.
Figure 5B:
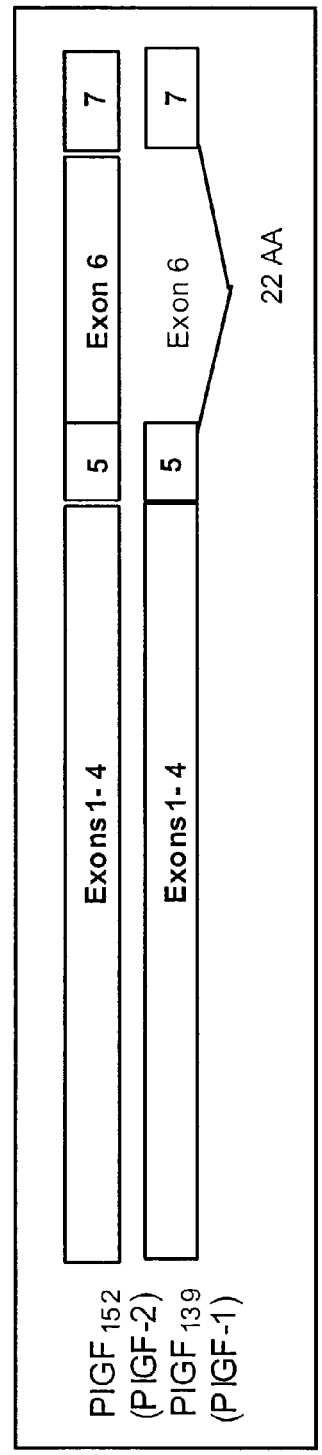
FIG. 5B illustrates the structural comparison between human $PIGF_{152}$ and $PIGF_{139}$.

VEGF$_{165}$ and VEGF$_{121}$ are differential splice variants of the same gene. As shown in FIG. 5, VEGF$_{165}$ is identical to VEGF$_{121}$ with the exception that it contains a 44 amino acid sequence (Exon 7) that is absent in VEGF$_{121}$. The Exon 7 region of VEGF$_{165}$ is highly basic, is a putative heparin binding domain, and contains seven cysteine residues. As shown in FIG. 5B, the PIGF family has two highly related ligands that are strikingly similar in exon structure to VEGF$_{165}$ and VEGF$_{121}$; PIGF$_{152}$ and PIGF$_{139}$. These two ligands also exist as splice variants of the same gene and differ only by a single exon, Exon 6. The Exon 6 region of PIGF$_{152}$ is similar to the Exon 7 region of VEGF$_{165}$ in that it is also a heparin-binding domain and is rich in basic amino acid residues.

The effects of peptides generated from the Exon 6 and Exon 7 portions of PIGF$_{152}$ on the binding of $^{125}$I-VEGF$_{165}$ and $^{125}$I-PIGF$_{152}$ in HUVEC were studied (Midgal et al., *J. Biol. Chem.* 1998; 273(35):22272–8). A peptide, consisting of the first 16 amino acid residues from Exon 6 (pp6) of PIGF$_{152}$, was sufficient to block the binding of $^{125}$I-VEGF$_{165}$ to a 120 kDa band whose characteristics were consistent with that of NP-1. Furthermore, this peptide blocked $^{125}$I-VEGF$_{165}$ binding to VEGFR-2. Additionally, a peptide consisting of the eight amino acids from Exon 7 of PIGF$_{152}$ appeared to bind to both receptors, but with lower effectiveness at similar doses. However, the ability of PIGF$_{152}$ to bind to NP-1 did not appear to provide a functional advantage over PIGF$_{139}$.

In another study (Soker et al., *J. Biol. Chem.* 1997; 272(50): 31582–8), the authors attempted to block the effects of NP-1 on VEGFR-2 signaling by creating a GST fusion protein containing the Exon 7 (44 AA) and Exon 8 (8 AA) regions of VEGF$_{165}$. This reagent, while effective in cells expressing VEGFR-2 and NP-1, was demonstrated to affect the response of both VEGF$_{165}$ and VEGF$_{121}$. Because the response of both VEGF$_{165}$ and VEGF$_{121}$ was affected, and VEGF$_{121}$ does not bind directly to NP-1, the site of action for the GST-Exon 7-Exon 8 protein could be directly at VEGFR-2. Furthermore, the deletion analysis presented was inconsistent with the structure of the Exon 7 and Exon 8 region of VEGF$_{165}$, suggesting that this protein may not mimic the actual NP-1 binding region of VEGF$_{165}$.

Based on this information, we synthesized a peptide that combined the Exon 6 region of PIGF and the Exon 8 region of VEGF (P6V8) SEQ ID NO:4 (Synpep, Inc., Dublin, Calif.). The peptide consisted of the first 16 residues of human PIGF$_{152}$ Exon 6 fused with entire Exon 8 region of VEGF$_{165}$ (P6V8 as shown in SEQ ID NO:4 and FIG. 6).

Figure 7:
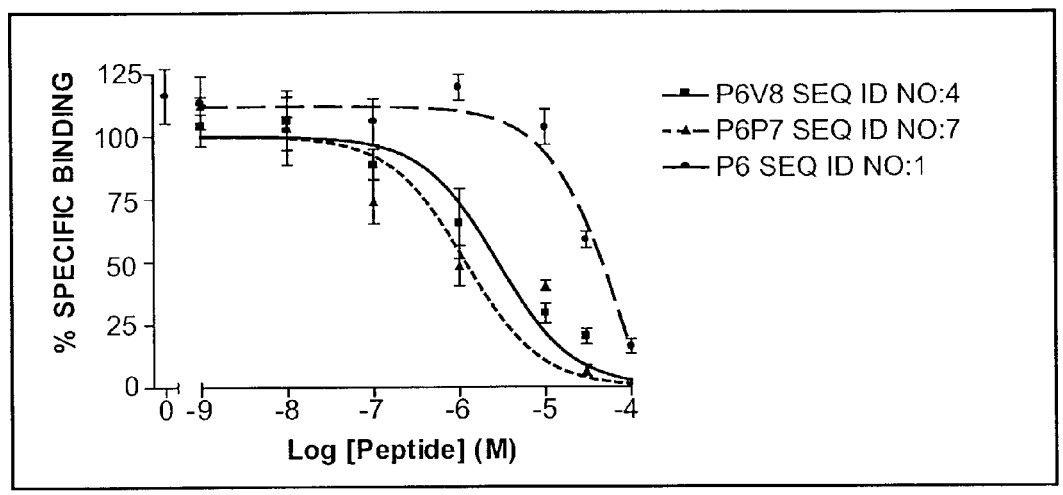
FIG. 7 is a graph of results comparing the binding affinity of various peptides to VEGFR-2/NP-1.

As shown in FIG. 7, while the P6 peptide as shown in SEQ ID NO:1 (IC$_{50}$=1.22×10$^{-5}$ M) does compete for $^{125}$I-VEGF$_{165}$ binding in cells overexpressing VEGFR-2 and NP-1, the P6V8 peptide as shown in SEQ ID NO:4 (IC$_{50}$=2.79×10$^{-6}$) and the P6P7 peptide as shown in SEQ ID NO:7 (IC$_{50}$=1.17×10$^{-6}$ M) compete for binding with a higher affinity. The higher affinity of P6V8 as shown in SEQ ID NO:4 compared to P6 as shown in SEQ ID NO:1 is also apparent in cells overexpressing NP-1 alone (Table 2).

P6V8 as shown in SEQ ID NO:4, and P6P7 as shown in SEQ ID NO:7, compete for $^{125}$I-VEGF$_{165}$ (201 pM) binding with similar affinity (IC$_{50}$=2.79×10$^{-6}$ M and 1.17×10$^{-6}$ M, respectively. The P6 peptide as shown in SEQ ID NO: 1 exhibits lower affinity (IC$_{50}$=1.22×10$^{-5}$M).

FIG. 8 demonstrates the effectiveness of the P6V8 peptide as shown in SEQ ID NO:4 versus the P6 peptide as shown in SEQ ID NO:1 at reducing the potency of VEGF$_{165}$ while having a minimal effect on the potency of VEGF$_{121}$. The experimental design is identical to that used to generate the data shown in FIG. 1, with the exception that the stimulations are done in the presence or absence of 100 μM of the indicated peptide. This experiment has been repeated once with similar results.

The EC$_{50}$ of VEGF$_{165}$ (283 pM) is shifted to the right by the addition of either P6 as shown in SEQ ID NO:1 (1.06 nM) or P6V8 as shown in SEQ ID NO:4 (7.25 nM) at a final concentration of 100 μM. Furthermore, the shift in the VEGF$_{165}$ EC$_{50}$ was more dramatic with P6V8 SEQ ID NO:4 versus P6 SEQ ID NO:1, consistent with the increased binding affinity of the P6V8 SEQ ID NO:4 peptide in cells expressing NP-1 alone, or in combination with VEGFR-2 (FIG. 7 and Table 2). In contrast to the effect on VEGF$_{165}$, the effect on VEGF$_{121}$ was minimal (EC$_{50}$=1.84 nM alone; 2.38 nM in the presence of P6; 4.04 nM in the presence of P6V8 SEQ ID NO:4).

These data indicate that the presence of the VEGF$_{165}$ Exon 8 sequence enhances the binding affinity and potency of the antagonist peptide, and stand in contrast to what was observed with the GST-Exon 7–8 fusion protein (Sokar et al., J. Biol. Chem. 1997: 272(50):31582–8) since the inventive antagonist affects the VEGF$_{165}$ response without affecting the response of VEGF$_{121}$. The lack of effect on the VEGF$_{121}$ response supports the hypothesis that the P6V8 SEQ ID NO:4 peptide does not have a direct effect on VEGFR-2, but antagonizes the activation of VEGFR-2 via an interaction with NP-1 and/or the VEGFR-2/NP-1 complex.

Minimal Peptide Size

To identify the minimum number of P6V8 SEQ ID NO:4 residues required for activity, a number of peptide derivatives that deleted residues from either the amino- or carboxy-terminus were synthesized. The results (average values) are shown in Table 2 and are expressed as "relative affinities" (RA), defined as the average of the IC$_{50}$ of the peptide divided by the IC$_{50}$ for VEGF$_{165}$ in a matched experiment.

Each of the peptides was tested for its ability to compete for $^{125}$I-VEGF$_{165}$ binding in COS-1 cells expressing NP-1 or VEGFR-2, or co-expressing VEGFR-2 in combination with NP-1. Each relative affinity value was calculated by taking the IC$_{50}$ value for the peptide divided by the IC$_{50}$ value for cold VEGF$_{165}$ in a matched experiment. Therefore, the larger the number, the lower the affinity of that peptide for the respective receptor.

TABLE 2

Peptide Length Dependency

| Peptide Name | VEGFR-2 | | | NP-1 | | | VEGFR-2/NP-1 | | |
|---|---|---|---|---|---|---|---|---|---|
| | Relative affinity | SEM | N | Relative affinity | SEM | N | Relative affinity | SEM | N |
| P6V8 SEQ ID NO:4 | 191[I] | 0 | 1 | 701 | 633 | 3 | 630 | 291 | 3 |
| P6V8-3N SEQ ID NO:13 | 475,115[II] | 473,303 | 2 | 1,166 | 1,162 | 3 | 1,466 | 1,047 | 4 |
| P6V8-8N SEQ ID NO:14 | 7,396 | 0 | 1 | 753 | 0 | 1 | 135 | 0 | 1 |
| P6V8-9N SEQ ID NO:19 | NC | 0 | 1 | 13,700 | 0 | 1 | 8,375 | 0 | 1 |
| P6 SEQ ID NO:1 | 5,495 | 0 | 1 | 24,536 | 13,433 | 4 | 15,161 | 9,954 | 1 |
| P6V8-3NCS SEQ ID NO:20 | 72,454[III] | 56,781 | 8 | 1,094 | 307 | 8 | 2,556 | 1,021 | 6 |
| P6V8-3NCS-1C SEQ ID NO:17 | 14,387 | 0 | 1 | 924 | 0 | 1 | 1,099 | 0 | 1 |
| P6V8-3NC5-2C SEQ ID NO:18 | 10,280 | 0 | 1 | 11,066 | 0 | 1 | NotTested | 0 | 0 |

NC = No competition for $^{125}$I-VEGF$_{165}$
[I]No competition for $^{125}$I-VEGF$_{165}$ in 2 of 3 experiments
[II]No competition for $^{125}$I-VEGF$_{165}$ in 2 of 4 experiments
[III]No competition for $^{125}$I-VEGF$_{165}$ in 4 of 8 experiments
Values displayed are relative to VEGF$_{165}$. Relative affinity is defined as the average of the IC$_{50}$ of the peptide divided by the IC$_{50}$ for VEGF in a matched experiment, SEM = Standard error of the mean, and N = # of experiments for the complete data set. For reference the average IC$_{50}$ for VEGF$_{165}$ at each receptor is 2.78 × 10$^{-10}$ M (log IC$_{50}$ = −9.56 ± 0.17 (N = 10)) for VEGFR-2; 5.82 × 10$^{-10}$ M (log IC$_{50}$ = −9.24 ± 0.14 (N = 10)) for NP-1; and 6.78 × 10$^{-10}$ M (log IC$_{50}$ = −9.17 ± 0.12 (N = 9)) for cells co-expressing VEGFR-2 and NP-1.

Removing the first three amino acids from the amino-terminus yields the sequence KGR GKR RRE KQR P CDK PRR, referred to as SEQ ID NO:13. This sequence SEQ ID NO: 13 reduced the ability of the peptide to compete for $^{125}$I-VEGF$_{165}$ binding to VEGFR-2 (P6V8 SEQ ID NO:4 RA=191, P6V8-3N SEQ ID NO:13 RA=475,115) without a substantial effect on binding affinity in cells expressing NP-1 alone, or NP-1 in combination with VEGFR-2.

This similarity in binding affinity was confirmed (FIG. 9), where the competition curves for P6V8 SEQ ID NO:4 and P6V8-3N overlap in both HUVEC (FIG. 9A) and COS-1 cells co-expressing VEGFR-2 and NP-1 (FIG. 9B). The P6V8 parent peptide SEQ ID NO:4 and the 3 amino terminal deletion derivatives compete for binding of $^{125}$I-VEGF$_{165}$ with similar affinity in HUVEC and COS-1 cells co-expressing both receptors.

These data indicate that COS-1 cells co-expressing VEGFR-2 and NP-1 may mimic the receptor complement observed in HUVEC expressing the endogenous receptor complement.

Figure 10A:
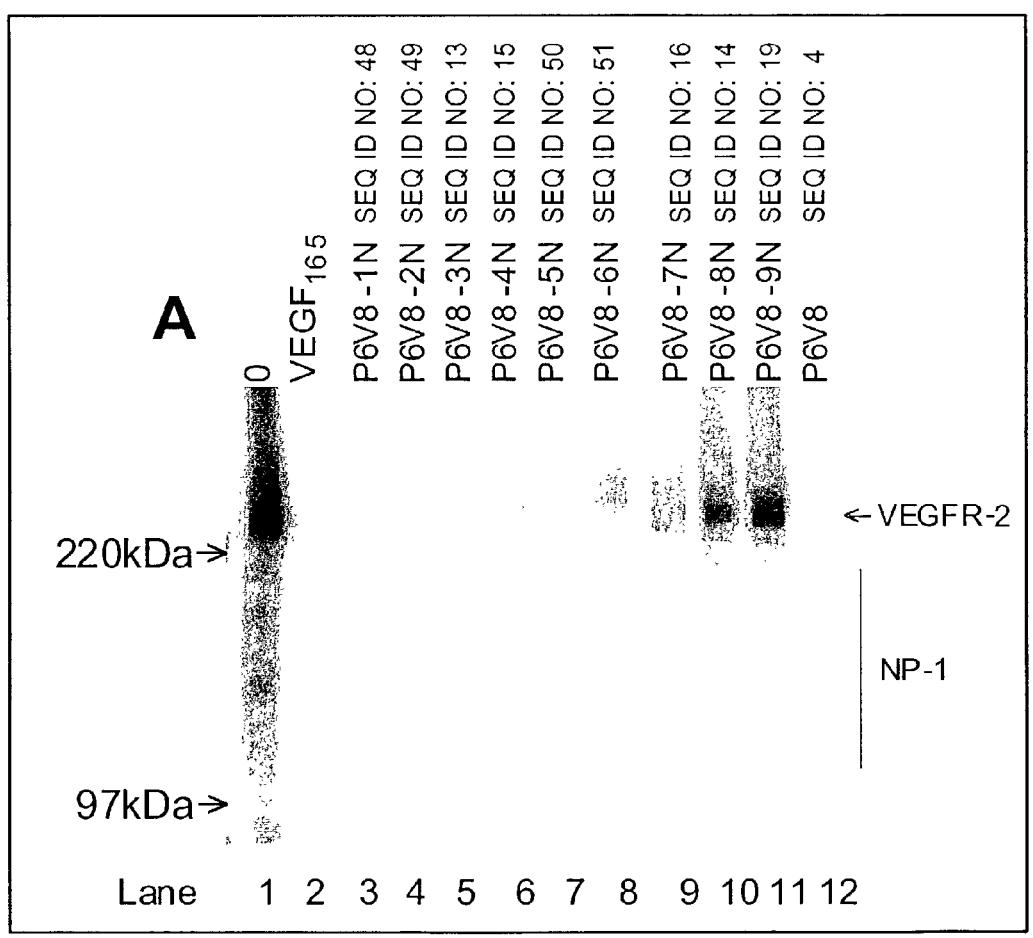
FIGS. 10A–B show results of binding of various peptides to the VEGFR-2/NP-1 complex.

Further amino terminal deletions were conducted. While P6V8-8N having the sequence RRR EKQ RPC DKP RR (PGV8-8N, referred to as peptide SEQ ID NO:14), demonstrated an increased affinity in cells co-expressing both VEGFR-2 and NP-1 (Table 2, RA=135), this did not appear to be the case in the endogenous cells, as shown in FIG. 10A. Endogenous HUVEC are affinity labeled using 500 pM (FIG. 10A), or 464 pM (FIG. 10B) $^{125}$I-VEGF$_{165}$ in the presence or absence of the indicated peptide at 100 µM final concentration at 4° C. for four hours. The cells are lysed, and the VEGFR-2/NP-1 complex is immunoprecipitated using VEGFR-2 receptor specific antibody, separated by SDS-PAGE, and developed using the Storm system (Molecular Dynamics).

Figure 10B:
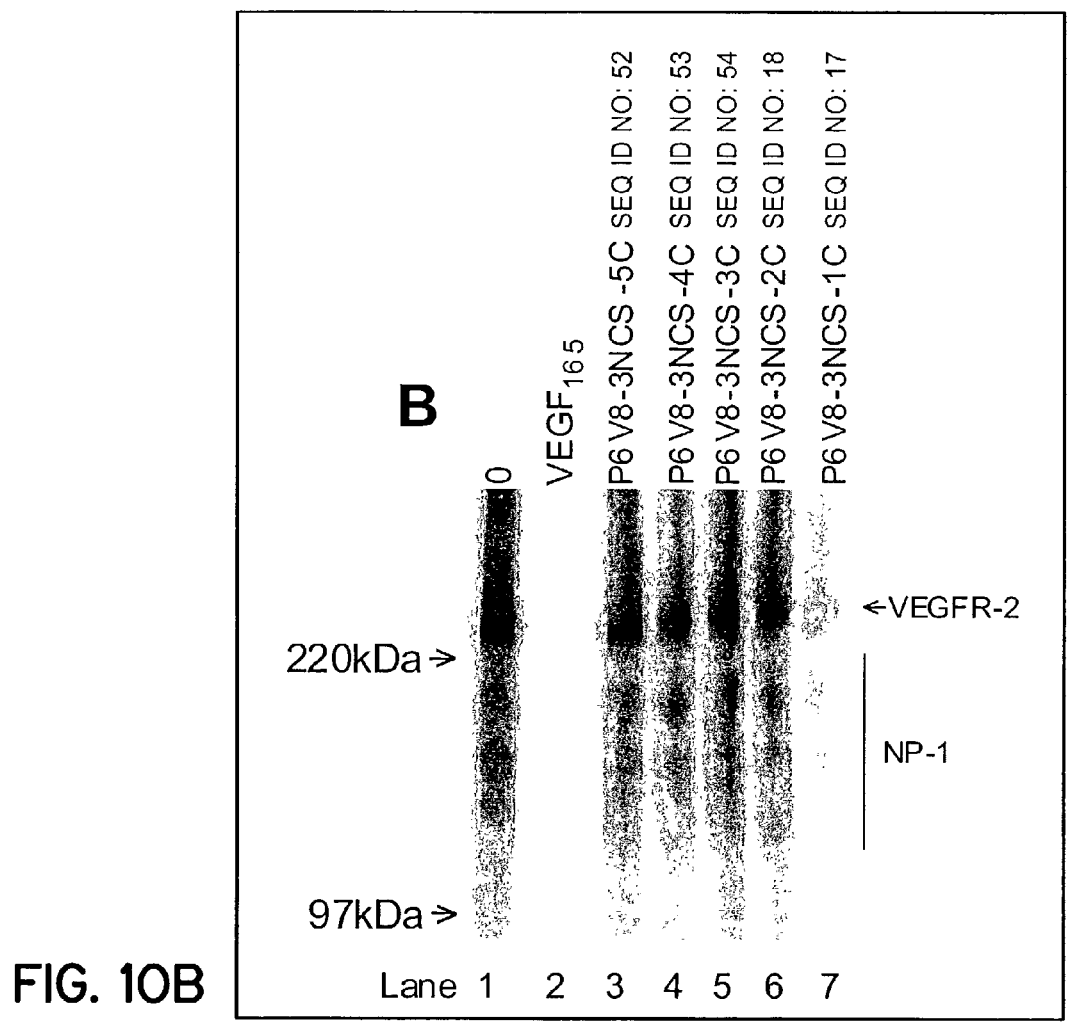

FIG. 10A demonstrates an increase in labeling of VEGFR-2 (lack of the ability of the peptide to compete for $^{125}$I-VEGF$_{165}$ binding to VEGFR-2) between the peptides referred to as P6V8-3N in SEQ ID NO:13 and P6V8-4N (having the sequence GRG KRR REK QRP CDKPRR SEQ ID NO:15) in VEGFR-2 immunoprecipitates. A further loss in binding is observed between the P6V8-7N sequence KRRREKQRPCDKPRR SEQ ID NO:16, and P6V8-8N SEQ ID NO:14 peptides. FIG. 10B demonstrates that the P6V8-3NCS-1C sequence KGR GKR RRE KQR P SDKPR SEQ ID NO: 17, partially competes, and that the P6V8-3NCS-2C peptide sequence KGR GKR RRE KQR P SDKP SEQ ID NO: 18, cannot compete for $^{125}$I-VEGF$_{165}$ binding in VEGFR-2 immunoprecipitates. Since the same molecule of $^{125}$I-VEGF$_{165}$ is shared between VEGFR-2 and NP-1 in the complex, and since the VEGFR-2 antibody co-immunoprecipitates the NP-1 receptor in complex with the VEGFR-2 receptor (lane 1, see also FIG. 4), the binding in the VEGFR-2 immunoprecipitation represents binding to both VEGFR-2 as well as the NP-1 detectable in the complex.

This increase in labeling represents the loss in the ability of the peptide to compete with $^{125}$I-VEGF$_{165}$ labeling of the complex, and therefore represents a loss in peptide affinity. Additionally, an even more dramatic loss in peptide binding is observed between P6V8-7N SEQ ID NO:16 (lane 9), and P6V8-8N SEQ ID NO:14 (lane 10) peptides. Because the ratios of receptor complement vary when COS-1 cells transiently overexpress VEGFR-2 and NP-1, a conservative approach using the data represented in FIG. 10 was used in assessment of the minimal peptide length, especially since the data for the P6V8-3N peptide SEQ ID NO:13 were identical in both the COS-1 and HUVEC systems (FIG. 9), and the P6V8-9N peptide RREK QRP CDK PRR, SEQ ID NO: 19 was clearly of lower affinity in both COS-1 cells (Table 2) and HUVEC (FIG. 10A).

Deletions from the carboxy-terminus results in loss of peptide binding, as demonstrated in FIG. 10B. Even with the deletion of the first carboxy terminal amino acid P6V8-3NCS-1C, SEQ ID NO:17, a reduction in peptide binding was evident (FIG. 10B, lane 7 versus 10A, lane 5). The further deletion of the next 2 to 5 carboxy terminal amino acids almost obliterated peptide binding (FIG. 10B, lanes 3 to 6) as the peptides were almost completely unable to compete for the $^{125}$I-VEGF$_{165}$ labeling of the VEGFR-2 band, and the now apparent NP-1 bands. To avoid any potential loss of peptide affinity, no residues were removed from the carboxy-terminus of the peptide.

Dimerization

The presence of a cysteine residue in the P6V8 peptide SEQ ID NO:4 suggested that the peptide might be dimerized, and that this dimerization was required for activity. To examine this potential requirement, additional peptides were synthesized in which the cysteine residue was mutated to the conserved but non-dimerizing amino acid serine.

TABLE 3

Effect of Dimerization on Binding to NP-1

| | VEGFR-2 | | | NP-1 | | | VEGFR-2/NP-1 | | |
|---|---|---|---|---|---|---|---|---|---|
| Peptide Name | Relative affinity | SEM | N | Relative affinity | SEM | N | Relative affinity | SEM | N |
| P6V8 SEQ ID NO:4 | 191 | 0 | 1 | 701 | 633 | 3 | 630 | 291 | 3 |
| P6V8CS SEQ ID NO:5 | 6,353 | 0 | 1 | 105 | 13 | 2 | 1,237 | 411 | 2 |
| P6V8-3N SEQ ID NO:13 | 475,115[I] | 473,303 | 2 | 1,166 | 1,162 | 3 | 1,466 | 1,047 | 4 |
| P6V8-3NCS SEQ ID NO:20 | 72,454[II] | 56,781 | 4 | 1,094 | 307 | 8 | 2,556 | 1,021 | 6 |

[I]No competition for $^{125}$I-VEGF$_{165}$ in 2 of 4 experiments
[II]No competition for $^{125}$I-VEGF$_{165}$ in 4 of 8 experiments
Values displayed are relative to VEGF$_{165}$. Relative affinity is defined as the average of the IC$_{50}$ of the peptide divided by the IC$_{50}$ for VEGF in a matched experiment, SEM = Standard error of the mean, and N = # of experiments for the complete data set. For reference the average IC$_{50}$ for VEGF$_{165}$ at each receptor is 2.78 × 10$^{-10}$ M (log IC$_{50}$ = −9.56 ± 0.17 (N = 10)) for VEGFR-2; 5.82 × 10$^{-10}$ M (log IC$_{50}$ = −9.24 ± 0.14 (N = 10)) for NP-1; and 6.78 × 10$^{-10}$ M (log IC$_{50}$ = −9.17 ± 0.12 (N = 9)) for cells co-expressing VEGFR-2 and NP-1.

The results show that dimerization is not required for binding to NP-1. As seen in Table 3, mutation of cysteine in the parent peptide P6V8 SEQ ID NO:4, resulting in the sequence shown in SEQ ID NO:5 and designated P6V8CS, actually reduced binding to VEGFR-2, with a slight improvement to no significant change in binding at NP-1, or VEGFR-2 in combination with NP-1, respectively (at NP-1: P6V8CS SEQ ID NO:5 RA=105 versus P6V8 SEQ ID NO:4 RA=701; at VEGFR-2/NP-1: P6V8CS SEQ ID NO:5 RA=1, 237 versus P6V8 SEQ ID NO:4 RA=630; at VEGFR-2: P6V8CS SEQ ID NO:5 RA=6,353 versus P6V8 SEQ ID NO:4 RA=191). Mutation of the cysteine residue in P6V8-3N SEQ ID NO:13 resulted in a slight but tolerable increase in the ability to compete for $^{125}$I-VEGF$_{165}$ binding at VEGFR-2 (P6V8-3N SEQ ID NO:13 RA=475,115 versus P6V8-3NCS sequence KGR GKR RRE KQR P SDKPRR, SEQ ID NO:20 RA=72,754), while still maintaining the ability to compete for $^{125}$I-VEGF$_{165}$ binding at isolated NP-1 (NP-1, P6V8-3NCS SEQ ID NO:20 RA=1,094 versus P6V8-3N SEQ ID NO:13 RA=1,166), or in cells co-expressing VEGFR-2 with NP-1 (P6V8-3N SEQ ID NO:13 RA=2,556 versus 1,466). These results indicated that dimerization was not required for activity at the isolated NP-1 receptor or the complex, and that mutating the cysteine in the P6V8-3N peptide SEQ ID NO:13 retained selectivity for the NP-1 receptor or to the complex, versus VEGFR-2 alone.

Cyclization

To determine if the peptide could be constrained by cyclization and still maintain activity, two separate cyclized version of the peptide were produced.

Figure 11:
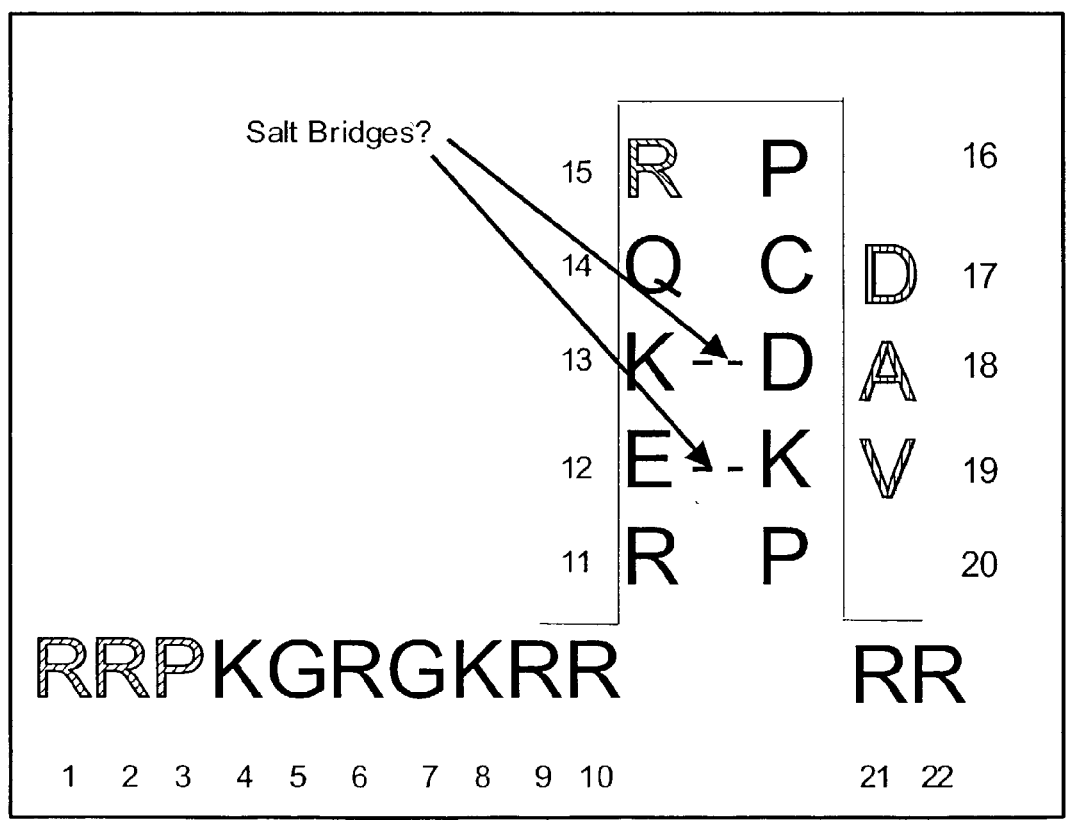
FIG. 11 shows the structure of the P6V8 peptide with potential salt bridges.

A circular dichroism analysis of P6V8 SEQ ID NO:4 concluded that the peptide contained beta sheet (18.3%) and turn structures (24.0%) (data not shown). The presence of beta sheet and turn structural elements suggested that proline at position 16 of the P6V8 SEQ ID NO:4 sequence might promote a turn such that potential salt bridges could form between amino acids 12 and 19, as well as between amino acids 13 and 18 (FIG. 11). In FIG. 11, the amino acids indicated with diagonal stripes have been determined to be dispensable without significant loss in peptide affinity. Also in FIG. 11, the amino acids indicated with vertical stripes and to the right of the proposed salt bridges represent the sequence differences between Exon 8 of VEGF$_{165}$ and Exon 7 of PIGF$_{152}$. Amino acids 4 to 22 represent the P6V8-3N peptide SEQ ID NO: 13.

The first cyclization was made in the P6V8-3N SEQ ID NO:13 sequence by replacing two of the residues involved in the potential salt bridge with cysteine residues. This peptide was designated P6V8-3NCSC13C18, which has the sequence KGR GKR RRE CQR PSC KPRR SEQ ID NO:9 with C13C18 denoting mutation of residues 13 and 18 to cysteine and with corresponding disulfide bridge formation. Compared to the P6V8-3NCS parent SEQ ID NO:20, the cyclization appeared to completely ablate the ability of the peptide to compete for $^{125}$I-VEGF$_{165}$ binding at the isolated VEGFR-2 receptor (RA=NC), while maintaining its ability to compete at the NP-1 receptor (RA=500), and the VEGFR-2/NP-1 complex (RA=132) (Table 4). Similarly, this cyclized peptide exhibited comparable binding in cells expressing NP-1 alone or in combination with VEGFR-2, to that observed with P6V8 SEQ ID NO:4 (Table 4).

TABLE 4

Effect of cyclization on the activity of the peptides

| Peptide Name | VEGFR-2 | | | NP-1 | | | VEGFR-2/NP-1 | | |
|---|---|---|---|---|---|---|---|---|---|
| | Relative affinity | SEM | N | Relative affinity | SEM | N | Relative affinity | SEM | N |
| P6V8 SEQ ID NO:4 | 191 | 0 | 1 | 701 | 633 | 3 | 630 | 291 | 3 |
| P6V8-3NCS SEQ ID NO:20 | 72,454[II] | 56,781 | 4 | 1,094 | 307 | 8 | 2,556 | 1,021 | 6 |
| P6V8-3NCSC13C18 SEQ ID NO:9 | NC | 0 | 1 | 500 | 0 | 1 | 132 | 0 | 1 |
| P6V8-3NCS1-7CC SEQ ID NO:12 | 3,334,264[I] | 0 | 1 | 1,071 | 339 | 5 | 4,457 | 1,047 | 4 |

NC = No competition
[I]No competition for $^{125}$I-VEGF$_{165}$ in 4 of 5 experiments
[II]No competition for $^{125}$I-VEGF$_{165}$ in 4 of 8 experiments
Values displayed are relative to VEGF$_{165}$. Relative affinity is defined as the average of the IC$_{50}$ of the peptide divided by the IC$_{50}$ for VEGF in a matched experiment, SEM = Standard error of the mean, and N = # of experiments for the complete data set. For reference the average IC$_{50}$ for VEGF$_{165}$ at each receptor is 2.78 × 10$^{-10}$ M (log IC$_{50}$ = −9.56 ± 0.17 (N = 10)) for VEGFR-2; 5.82 × 10$^{-10}$ M (log IC$_{50}$ = −9.24 ± 0.14 (N = 10)) for NP-1; and 6.78 × 10$^{-10}$ M (log IC$_{50}$ = −9.17 ± 0.12 (N = 9)) for cells co-expressing VEGFR-2 and NP-1.

In the second version of the cyclized peptide, cysteines were inserted at the −1 position and substituted for position 7 of the P6V8-3N peptide SEQ ID NO:13 (Position 10 of P6V8 SEQ ID NO:4, FIG. 11). This peptide, designated as P6V8-3NCS1-7CC SEQ ID NO:12, demonstrated similar properties as the P6V8-3NCSC13C18 SEQ ID NO:9 peptide discussed above (Table 4).

These results demonstrated the peptides could be cyclized without loss of binding to NP-1, or to the VEGFR-2/NP-1 complex. Additionally, these cyclizations pointed out the possibility that modifications to the peptide sequence could lead to receptor-specific peptides, in that virtually no direct binding to VEGFR-2 is observed when VEGFR-2 is expressed in isolation.

Critical Residue Identification

Alanine scanning is a standard technique employed by one of skill in the art to examine whether or not an amino acid residue is required in a protein:protein interaction. In this technique, natural residues in the wild type sequence are sequentially substituted with the relatively inert alanine residue. By removing specific residues and comparing the activity of the mutated peptide to the parent peptide, one can infer whether or not the mutated residue is critical for the protein:protein interaction being studied.

In an effort to identify which residues within the inventive peptide maintained the ability to compete for $^{125}$I-VEGF$_{165}$ binding at the VEGFR-2/NP-1 complex, the alanine scanning technique was used. Additionally, peptides that would compete for $^{125}$I-VEGF$_{165}$ binding to the isolated NP-1 receptor and the VEGFR-2/NP-1 receptor complex, without competing for $^{125}$I-VEGF$_{165}$ binding to isolated VEGFR-2, could be designed and the alanine scan could reveal amino acids required for binding to VEGFR-2, wherein substitution of those amino acids would result in a peptide that binds to NP-1 or the VEGFR-2/NP-1 complex without appreciable binding to VEGFR-2. The reagent generated would then be expected to function only as an antagonist of the NP-1 receptor or the VEGFR-2/NP-1 receptor complex.

The initial sets of these peptides synthesized were AS-1 through AS-5, and were created (starting with the parent P6V8 SEQ ID NO:4 peptide) by replacing residues with alanine in groups of three, with the designations for these peptides following a sequential order (AS-1 RRP AAA GKR RRE KQR PSD KPR R SEQ ID NO:21, AS-2 RRP KGR AM RRE KQR PSD KPR R SEQ ID NO:22, AS-3 RRP KGR GKR AAA KQR PSD KPR R SEQ ID NO:23). The first three amino acid residues were included in the peptides, but were not substituted because they had been previously demonstrated to be dispensable for binding activity at NP-1 or in cells co-expressing VEGFR-2 with NP-1 (Table 2 and FIG. 9). This initial scan demonstrated that the next six residues (AA 4–9, FIG. 11) were important for VEGFR-2 binding, as demonstrated by the relative affinity to the lead peptide (RALP) values for AS-1 SEQ ID NO:21 (RALP at R2=NC) and AS-2 SEQ ID NO:22 (RALP at R2=10) listed in Table 5. The RALP value was calculated by taking the $IC_{50}$ value for the peptide divided by the $IC_{50}$ for P6V8CS SEQ ID NO:5 in a matched experiment, and was a measurement of fold loss in affinity. Residues 4 through 6 of P6V8 SEQ ID NO:4 (AS-1 SEQ ID NO:21) were significant for the ability to compete for $^{125}I$-$VEGF_{165}$ binding at NP-1 (AS-1 SEQ ID NO:21 RALP at NP1=8), but not for activity at the VEGFR-2 and NP-1 complex (RALP at VEGFR-2/NP-1=1). Residues 7 through 9 of P6V8 SEQ ID NO:4 (AS-2 SEQ ID NO:22) were more significant for binding to NP-1 (RALP at NP-1=28), and to the VEGFR-2/NP-1 complex (RALP at VEGFR-2/NP-1=9).

Several peptides were created that contained single or grouped alanine substitutions. This group of peptides did not include the first three residues and were created from P6V8-3NCS SEQ ID NO:20 (for example, amino acids 4 through 6 from AS-1 SEQ ID NO:21 above are the same as positions A1, A2 and A3 in this series of peptides). Consistent with the data collected on the parent peptide P6V8-3NCS SEQ ID NO:20, none of these peptides competed for $^{125}I$-$VEGF_{165}$ binding at VEGFR-2 with any significant affinity (Table 5).

Table 5 summarizes the results of the linear alanine scan on the activity of the peptides.

TABLE 5

Summary of Linear Alanine Scan Results on Peptide Activity

| Peptide Name | VEGFR-2 | | | NP-1 | | | VEGFR-2/NP-1 | | |
|---|---|---|---|---|---|---|---|---|---|
| | Relative Affinity to Lead Peptide | SEM | N | Relative Affinity to Lead Peptide | SEM | N | Relative Affinity to Lead Peptide | SEM | N |
| P6V8-3NCS SEQ ID NO:20 | 72,754 | 56,781 | 4 | 1,094 | 307 | 8 | 2,556 | 1,021 | 6 |
| P6V8-3NCSA1 SEQ ID NO:24 | NC | 0 | 1 | 0.99 | 0 | 1 | 14.30 | 0 | 1 |
| P6V8-3NCSA5 SEQ ID NO:25 | NC | 0 | 1 | 2.60 | 0 | 1 | 1.45 | 0 | 1 |
| P6V8-3NCSA1A5 SEQ ID NO:26 | NC | 0 | 1 | 0.48 | 0 | 1 | 0.71 | 0 | 1 |
| P6V8-3NCSA3 SEQ ID NO:27 | NC | 0 | 2 | 8.80 | 7 | 2 | 0.23 | 0.17 | 2 |
| P6V8-3NCSA6 SEQ ID NO:28 | NC | 0 | 2 | 2.16 | 0.84 | 2 | 5.10 | 3.50 | 2 |
| P6V8-3NCSA3A6 SEQ ID NO:29 | NC | 0 | 2 | 48.80 | 41.4 | 2 | 8.20 | 4.88 | 2 |
| P6V8-3NCSA1A6 SEQ ID NO:30 | NC | 0 | 1 | 2.30 | 0 | 1 | 0.93 | 0 | 1 |
| P6V8-3NCSA7, 8, 10, 12, 16, 18 SEQ ID NO:55 | NC | 0 | 1 | 72.44 | 0 | 1 | 27.540 | | 1 |
| P6V8-3NCSA16, 18, 19 SEQ ID NO:32 | 1.75 | 0 | 1 | 56.62 | 0 | 1 | NC | 0 | 1 |
| P6V8-3NCSA7, 8, 10 SEQ ID NO:33 | NC | 0 | 1 | 14.25 | 0 | 1 | 3.27 | 0 | 1 |
| P6V8-3NCSA7, 8, 12 SEQ ID NO:34 | NC | 0 | 1 | 1.91 | 0 | 1 | NC | 0 | 1 |
| P6V8-3NCSA1, 5, 7, 8, 10 SEQ ID NO:35 | NC | 0 | 1 | 67.76 | 0 | 1 | 5.22 | 0 | 1 |
| P6V8-3NCSA1, 5, 7, 8, 12 SEQ ID NO:36 | NC | 0 | 1 | 10.23 | 0 | 1 | 4.24 | 0 | 1 |
| P6V8CS SEQ ID NO:5 | 6,353 | 0 | 1 | 105 | 13 | 2 | 1,237 | 411 | 2 |
| AS-1 SEQ ID NO:21 | NC | 0 | 1 | 8 | 0 | 1 | 1 | 0 | 1 |
| AS-2 SEQ ID NO:22 | 10 | 0 | 1 | 28 | 0 | 1 | 9 | 0 | 1 |
| AS-3 SEQ ID NO:23 | 4 | 0 | 1 | 0.55 | 0 | 1 | NC | 0 | 1 |
| AS-4 SEQ ID NO:37 | NC | 0 | 1 | 0.45 | 0 | 1 | 4.2 | 0 | 1 |

TABLE 5-continued

Summary of Linear Alanine Scan Results on Peptide Activity

| Peptide Name | VEGFR-2 | | | NP-1 | | | VEGFR-2/NP-1 | | |
|---|---|---|---|---|---|---|---|---|---|
| | Relative Affinity to Lead Peptide | SEM | N | Relative Affinity to Lead Peptide | SEM | N | Relative Affinity to Lead Peptide | SEM | N |
| AS-4a SEQ ID NO:38 | 1.9 | 0 | 1 | 2.1 | 0 | 1 | 0.78 | 0 | 1 |
| AS-5 SEQ ID NO:39 | NC | 0 | 1 | 1.6 | 0 | 1 | 0.71 | 0 | 1 |

Values displayed are relative to the lead peptide P6V8-3NCS except for the AS series where the lead peptide is P6V8CS. Relative affinity to the lead peptide (RALP) is defined as the average of the $IC_{50}$ of the peptide divided by the $IC_{50}$ for P6V8-3NCS peptide in a matched experiment, SEM = Standard error of the mean, and N = # of experiments for the complete data set. For reference the average $IC_{50}$ for $VEGF_{165}$ at each receptor is $2.78 \times 10^{-10}$ M (log $IC_{50} = -9.56 \pm 0.17$ (N = 10)) for VEGFR-2; $5.82 \times 10^{-10}$ M (log $IC_{50} = -9.24 \pm 0.14$ (N = 10)) for NP-1; and $6.78 \times 10^{-10}$ M (log $IC_{50} = -9.17 \pm 0.12$ (N = 9)) for cells co-expressing VEGFR-2 and NP-1. NC = no competition. The P6V8-3NCS and P6V8CS values are relative to $VEGF_{165}$.

Table 5 demonstrates that the residue at position 1 of P6V8-3NCS SEQ ID NO:20 must be basic to maintain the ability to compete for $^{125}I$-$VEGF_{165}$ binding in cells co-expressing VEGFR-2 and NP-1. When this residue is mutated to alanine, P6V8-3NCSA1 (RALP at VEGFR-2/NP-1=14.33), there was a significant increase in the relative affinity (loss of activity) of the peptide for the VEGFR-2/NP-1 complex. Interestingly, there was no loss of binding affinity at NP-1 with this peptide (RALP at NP-1=0.99). The P6V8-3NCSA5 SEQ ID NO:25 data in Table 5 indicate that the nature of this residue is not critical because the mutation of the fifth residue to alanine does not significantly change the peptide's affinity relative to the lead peptide (RALP at NP-1=2.60; RALP at VEGFR-2/NP-1=1.45). Furthermore, a peptide mutated at both the first and fifth residues (P6V8-3NCSA1A5 SEQ ID NO:26) functions similarly, if not slightly better than, P6V8-3NCS SEQ ID NO:20 as indicated by the RALP values at NP-1 (RALP=0.48) and VEGFR-2/NP-1 (RALP=0.71). These data suggest that the loss of the basic residue at position 1 of P6V8-3NCS SEQ ID NO:18 can be tolerated only if there is also a loss of the basic residue at position 5.

Position 3 is basic (Table 5), and the mutation of the residue at position 3 to alanine (P6V8-3NCSA3 SEQ ID NO:27) affects binding of the peptide at NP-1 (RALP=8.8), but not in cells co-expressing the VEGFR-2 and NP-1 (RALP=0.23). Additionally, there was a small loss in activity at the VEGFR-2/NP-1 complex when position 6 was mutated to alanine (P6V8-3NCSA6 SEQ ID NO:28 RALP at VEGFR-2/NP-1=5.10). However, when both residues at positions 3 and 6 were mutated to alanine (P6V8-3NCSA3A6 SEQ ID NO:29), a significant loss of activity is noted at both NP-1 (RALP=48.8), and at the VEGFR-2/NP-1 complex (RALP=8.20). These data suggest that the basic residues at both position 3 and position 6 must be maintained, both alone and in concert, for maximal binding to NP-1, or to the VEGFR-2/NP-1 complex.

Additionally, Table 5 demonstrates the need to maintain basic residues at the carboxy terminus of the peptide. When positions 16,18, and 19 were mutated to alanine, (P6V8-3NCSA16,18,19 SEQ ID NO:32), the binding of the peptide to NP-1 (RALP=56.62), as well as to the VEGFR-2/NP-1 receptor complex (RALP=NC) is lost. This is consistent with the carboxy terminal deletion analysis displayed in FIG. 10B.

The basic residues in the middle of the peptide appear to be important for binding as well. AS-3 SEQ ID NO:23, which substitutes positions 7 and 8 of P6V8-3NCS SEQ ID NO:20 to alanine, results in a complete loss of binding to the VEGFR-2/NP-1 complex, without a substantial effect at NP-1 alone. Further mutation of the basic residue at position 10 (P6V8-3NCSA7,8,10 SEQ ID NO:33) negatively affects binding at NP-1 (RALP=14.25), but not as substantially as at the VEGFR-2/NP-1 complex (RALP=3.27). Additionally, mutation of the residue at position 12 (P6V8-3NCSA7,8,12 SEQ ID NO:34) negatively effects activity at the VEGFR-2/NP-1 complex (RALP=NC), but not substantially at NP-1 (1.91).

The effects of alanine substitution on the cyclized peptides were examined, as shown in Table 6.

TABLE 6

Summary of Cyclic Alanine Peptide Scan Results on the Binding of the Peptides

| Peptide Name | VEGFR-2 | | | NP-I | | | VEGFR-2INP-I | | |
|---|---|---|---|---|---|---|---|---|---|
| | Relative Affinity to Lead | SEM | N | Relative Affinity to Lead | SEM | N | Relative Affinity to Lead | SEM | N |
| P6V8-3NCS1-7CC SEQ ID NO:12 | 3,334,264 | 0 | 1 | 1,071 | 339 | 5 | 4,457 | 1,704 | 4 |
| P6V8-3NCS1-7CCA1 SEQ ID NO:40 | NC | 0 | 1 | 14.35 | 0 | 1 | 1.97 | 0 | 1 |
| P6V8-3NCS1-7CCA5 SEQ ID NO:41 | NC | 0 | 1 | 1.64 | 0 | 1 | 1.87 | 0 | 1 |
| P6V8-3NCS1-7CCA1A5 SEQ ID NO:42 | NC | 0 | 1 | 30.76 | 0 | 1 | 17.33 | 0 | 1 |

TABLE 6-continued

Summary of Cyclic Alanine Peptide Scan Results on the Binding of the Peptides

| Peptide Name | VEGFR-2 | | | NP-1 | | | VEGFR-2/NP-1 | | |
| --- | --- | --- | --- | --- | --- | --- | --- | --- | --- |
| | Relative Affinity to Lead | SEM | N | Relative Affinity to Lead | SEM | N | Relative Affinity to Lead | SEM | N |
| (cap)P6V8-3NCS1-7CC SEQ ID NO:43 | NC | 0 | 2 | 60.39 | 0 | 1 | 63.24 | 0 | 1 |

Values displayed are relative to the lead peptide P6V8-3NCW1-7CC, SEQ ID NO:12. Relative affinity to the lead peptide (RALP) is defined as the average of the $IC_{50}$ of the peptide divided by the $IC_{50}$ for P6V8-3NCS1-7CC, SEQ ID NO:10 in a matched experiment. The P6V8-3NCS1-7CC values are relative to $VEGF_{165}$, SEM = Standard error of the mean, and N = # of experiments for the complete data set. For reference the average $IC_{50}$ for $VEGF_{165}$ at each receptor is $2.78 \times 10^{-10}$ M (log $IC_{50}$ = −9.56 ± 0.17 (N = 10)) for VEGFR-2; $5.82 \times 10^{-10}$ M (log $IC_{50}$ = −9.24 ± 0.14 (N = 10)) for NP-1; and $6.78 \times 10^{-10}$ M (log $IC_{50}$ = −9.17 ± 0.12 (N = 9)) for cells co-expressing VEGFR-2 and NP-1. NC = no competition.

Cyclization of the amino-terminus or middle (C13 to C18) residues dramatically increased the selectivity of the peptide for NP-1, or for the VEGFR-2/NP-1 complex, versus VEGFR-2 alone (Table 4). In contrast to the linear peptide data (Table 5), when lysine at position 1 was mutated to alanine in the cyclized peptide (P6V8-3NCSA-17CCA1 SEQ ID NO:40), the relative affinity for the NP-1 receptor was decreased (RALP=14.35), with only a minimal effect on binding to the VEGFR-2/NP-1 complex (compare P6V8-3NCSA1 SEQ ID NO:24 in Table 5 to the value of the corresponding cyclized peptide (P6V8-3NCS1-7CCA1 SEQ ID NO:40) in Table 6. In contrast, substitution of lysine at position 5 (P6V8-3NCS1-7CCA5 SEQ ID NO:41) demonstrated a loss in the affinity of the peptide for the NP-1 receptor (Table 6, P6V8-3NCS1-7CCA5 SEQ ID NO:41, RALP=1.64) similar to that seen in the linear version (Table 5, P6V8-3NCSA5 SEQ ID NO:25, RALP=2.6). Notably, the dual substitution of both lysines in the cyclized version of the peptide (P6V8-3NCS1-7CCA1A5 SEQ ID NO:42) resulted in a substantial loss in the ability to compete for $^{125}$I-VEGF$_{165}$ binding at either the NP-1 receptor (RALP=30.76), or the VEGFR-2/NP-1 complex (RALP=17.33) where, as in the linear version, these combined substitutions had no effect (Table 5, P6V8-3NCSA1A5 SEQ ID NO:26, RALP=0.46).

Amino Terminal and Carboxyl Terminal Capping Effect

To make the peptides resistant to the action of aminopeptidases and carboxypeptidases, two peptides, P6V8-3NCS SEQ ID NO:20, and P6V8-3NCS1-7CC SEQ ID NO:12, were synthesized with capped ends, designated as (cap) P6V8-3NCS SEQ ID NO:44 and (cap)P6V8-3NCS1-7CC SEQ ID NO:43, respectively. These peptides lacked ability to compete for $^{125}$I-VEGF$_{165}$ binding in any receptor binding studies attempted (see Tables 6 and 10). The lack of binding affinity was not due to the degradation of the peptides during the course of the binding experiments, as their stability was confirmed by HPLC. This suggested that the termini of the peptides must be free for activity.

Site of Action

The fact that the peptides P6 SEQ ID NO:1 and P6V8 SEQ ID NO:4 antagonized only VEGF$_{165}$ activation of VEGFR-2, without affecting VEGF$_{121}$-mediated activation of this receptor (FIG. 8), suggested that the site of action was not directly at VEGFR-2. This is confirmed upon examination of the antagonistic activity of a peptide that lacked substantial access to VEGFR-2 when VEGFR-2 is expressed alone in COS-1 cells. The P6V8-3NCSC13C18 peptide SEQ ID NO:9 provides such an example, as it lacks binding to VEGFR-2 while maintaining binding to both NP-1 and to the VEGFR-2/NP-1 complex (Table 4).

With reference to FIG. 12, HUVEC were stimulated with ligand for five minutes at 37° C., lysed, and immunoprecipitated with an antibody specific to VEGFR-2. Following SDS-PAGE separation and transfer, the blots were probed using an antiphosphotyrosine antibody (4G10, UBI) and developed using standard enhanced chemiluminescence (ECL) techniques (upper panels). These same blots were then stripped and reprobed using an antibody specific for VEGFR-2 (lower panels). The films were then scanned and quantitated using Image Quant (Molecular Dynamics). The non-linear regression analysis (Prism, San Diego, Calif.) of the PY/R2 signal ratio yielded EC$_{50}$ results of $1.26 \times 10^{-10}$ M for VEGF$_{165}$, $7.76 \times 10^{-9}$ M for VEGF$_{165}$+antagonist, $2.75 \times 10^{-9}$ M for VEGF$_{121}$ alone, and $2.08 \times 10^{-9}$ M for VEGF$_{121}$+antagonist.

As shown in FIG. 12, this compound retained antagonistic activity against VEGF$_{165}$ without affecting VEGF$_{121}$, thereby providing additional support that the site of action for these peptides was NP-1 or the VEGFR-2/NP-1 complex.

In order to discriminate the site of action as being the VEGFR-2/NP-1 complex versus NP-1 alone, several compounds that had little or no binding affinity for VEGFR-2 were tested to determine if any exhibited selectivity for the isolated NP-1 receptor or the VEGFR-2/NP-1 receptor complex, as measured by binding affinity in COS-1 cells expressing either NP-1 alone or in conjunction with VEGFR-2 (Table 10). The peptides that demonstrated a lack of binding to VEGFR-2 were divided into two classes, NP-1-selective (Table 7), or VEGFR-2/NP-1 complex-selective (Table 8), and potential representative peptides from each class were identified. From Table 7, AS-4 SEQ ID NO:37 was selected because it had the highest affinity at NP-1, while still exhibiting about 100 fold selectivity for cells expressing NP-1 alone versus cells co-expressing VEGFR-2 and NP-1.

TABLE 7

Summary of NP-1 receptor-selective peptides

| Peptide | VEGFR-2 Relative affinity | SEM | N | NP-1 Relative affinity | SEM | N | VEGFR-2/NP-1 Relative affinity | SEM | N |
|---|---|---|---|---|---|---|---|---|---|
| P6V8 SEQ ID NO:4 | 191 | 0 | 1 | 701 | 633 | 3 | 630 | 291 | 3 |
| P6V8-3N SEQ ID NO:13 | 475,115 | 473,303 | 2 | 1,166 | 1,162 | 3 | 1,466 | 1,047 | 4 |
| P6V8CS SEQ ID NO:5 | 6,353 | 0 | 1 | 105 | 13 | 2 | 1,237 | 411 | 2 |
| P6V8-3NCSA6 SEQ ID NO:28 | 82,297 | 0 | 2 | 713 | 539 | 2 | 5,636 | 5,227 | 2 |
| P6V8-3NCS1-7CC SEQ ID NO:12 | 3,334,264 | 0 | 1 | 1,071 | 339 | 5 | 4,457 | 1,704 | 4 |
| P6V8-3NCSA1 SEQ ID NO:24 | 124,165 | 0 | 1 | 413 | 0 | 1 | 17,884 | 0 | 1 |
| AS-4 SEQ ID NO:37 | NC | 0 | 1 | 55 | 0 | 1 | 6,934 | 0 | 1 |
| AS-4A SEQ ID NO:38 | NC | 0 | 1 | 194 | 0 | 1 | 1,185 | 0 | 1 |
| AS-2 SEQ ID NO:22 | 62,661 | 0 | 1 | 3,365 | 0 | 1 | 14,288 | 0 | 1 |
| AS-3 SEQ ID NO:23 | 27,221 | 0 | 1 | 65 | 0 | 1 | ND | 0 | 1 |

Values displayed are relative to $VEGF_{165}$. Relative affinity is defined as the average of the $IC_{50}$ of the peptide divided by the $IC_{50}$ for VEGF in a matched experiment, SEM = Standard error of the mean, and N = # of experiments for the complete data set. For reference the average $IC_{50}$ for $VEGF_{165}$ at each receptor is $2.78 \times 10^{-10}$ M (log $IC_{50}$ = $-9.56 \pm 0.17$ (N = 10)) for VEGFR-2; $5.82 \times 10^{-10}$ M (log $IC_{50}$ = $-9.24 \pm 0.14$ (N = 10)) for NP-1; and $6.78 \times 10^{-10}$ M (log $IC_{50}$ = $-9.17 \pm 0.12$ (N = 9)) for cells co-expressing VEGFR-2 and NP-1. NC = No competition for $^{125}$I-$VEGF_{165}$.

TABLE 8

Summary of VEGFR-2/NP-1 receptor complex-selective peptides

| Peptide | VEGFR-2 Relative affinity | SEM | N | NP-1 Relative affinity | SEM | N | VEGFR-2/NP-1 Relative affinity | SEM | N |
|---|---|---|---|---|---|---|---|---|---|
| P6V8 SEQ ID NO:4 | 191 | 0 | 1 | 701 | 633 | 3 | 630 | 291 | 3 |
| P6V8-3NCS SEQ ID NO:20 | 72,754 | 56,781 | 4 | 1,094 | 307 | 8 | 2,556 | 1,021 | 6 |
| P6V8-3NCSA3 SEQ ID NO:27 | 485,288 | 0 | 1 | 1,380 | 737 | 2 | 258 | 242 | 2 |
| P6V8-3NCS1-7CCA1 SEQ ID NO:40 | NC | 0 | 1 | 33,574 | 0 | 1 | 5,521 | 0 | 1 |
| P6V8-3NCSC13C18 SEQ ID NO:9 | NC | 0 | 1 | 500 | 0 | 1 | 132 | 0 | 1 |

Values displayed are relative to $VEGF_{165}$. Relative affinity is defined as the average of the $IC_{50}$ of the peptide divided by the $IC_{50}$ for VEGF in a matched experiment, SEM = Standard error of the mean, and N = # of experiments for the complete data set. For reference the average $IC_{50}$ for $VEGF_{165}$ at each receptor is $2.78 \times 10^{-10}$ M (log $IC_{50}$ = $-9.56 \pm 0.17$ (N = 10)) for VEGFR-2; $5.82 \times 10^{-10}$ M (log $IC_{50}$ = $-9.24 \pm 0.14$ (N = 10)) for NP-1; and $6.78 \times 10^{-10}$ M (log $IC_{50}$ = $-9.17 \pm 0.12$ (N = 9)) for cells co-expressing VEGFR-2 and NP-1. NC = No competition for $^{125}$I-$VEGF_{165}$.

TABLE 9

Summary of receptor-selective peptides

| COS-1: Peptide Name | VEGFR-2 Relative affinity | SEM | N | NP-1 Relative affinity | SEM | N | VEGFR-2/NP-1 Relative affinity | SEM | N |
|---|---|---|---|---|---|---|---|---|---|
| P6V8-3N SEQ ID NO:13 | 475,115[1] | 473,303 | 2 | 1,116 | 1,162 | 3 | 1,466 | 1,047 | 4 |
| AS-4 | NC | 0 | 1 | 55 | 0 | 1 | 6,934 | 0 | |

TABLE 9-continued

Summary of receptor-selective peptides

SEQ ID NQ:37

| Stable Balb/c: | NP-1 | | | VEGFR-2/NP-1 | | |
|---|---|---|---|---|---|---|
| Peptide Name | Relative affinity | SEM | N | Relative affinity | SEM | N |
| P6V8-3N SEQ ID NO:13 | 1,607 | 0 | 1 | 6,928 | 0 | 1 |
| AS-4 SEQ ID NO:37 | 112 | 0 | 1 | 3,856 | 0 | 1 |

[1]No competition for $^{125}$I-VEGF$_{165}$ in 2 of 4 experiments
Values displayed are relative to VEGF$_{165}$. Relative affinity is defined as the average of the IC$_{50}$ of the peptide divided by the IC$_{50}$ for VEGF in a matched experiment, SEM = Standard error of the mean, and N = # of experiments for the complete data set. For reference the average IC$_{50}$ for VEGF$_{165}$ in COS-1 cells at each receptor is $2.78 \times 10^{-10}$ M (log IC$_{50}$ = $-9.56 \pm 0.17$ (N = 10)) for VEGFR-2; $5.82 \times 10^{-10}$ M (log IC$_{50}$ = $-9.24 \pm 0.14$ (N = 10)) for NP-1; and $6.78 \times 10^{-10}$ M (log IC$_{50}$ = $-9.17 \pm 0.12$ (N = 9)) for cells co-expressing VEGFR-2 and NP-1. For the Balb/C 3T3 A31 cells the IC$_{50}$ values for P6V8-3N, SEQ ID NO:13 were $2.54 \times 10^{-7}$ M and $5.39 \times 10^{-7}$ M for NP-1 and VEGFR-2/NP-1 cells respectively. Additionally, the IC$_{50}$ values for AS-4 were $1.78 \times 10^{-8}$ M and $3.00 \times 10^{-7}$ M for NP-1 and VEGFR-2/NP-1 cells respectively. The corresponding IC$_{50}$ values for VEGF$_{165}$ are $1.58 \times 10^{-10}$ M and $7.78 \times 10^{-11}$ (M for NP-1 and VEGFR-2/NP-1 cells respectively).

Because co-expression of NP-1 with VEGFR-2 could not be guaranteed in every cell in the transient expression system, the higher affinity of AS-4 SEQ ID NO:37 in cells expressing NP-1 alone, compared to cells expressing VEGFR-2 and NP-1, was also verified in the Balb/C3T3 A31 stable cell system overexpressing NP-1 alone or in concert with VEGFR-2 (Table 9).

Figure 13:
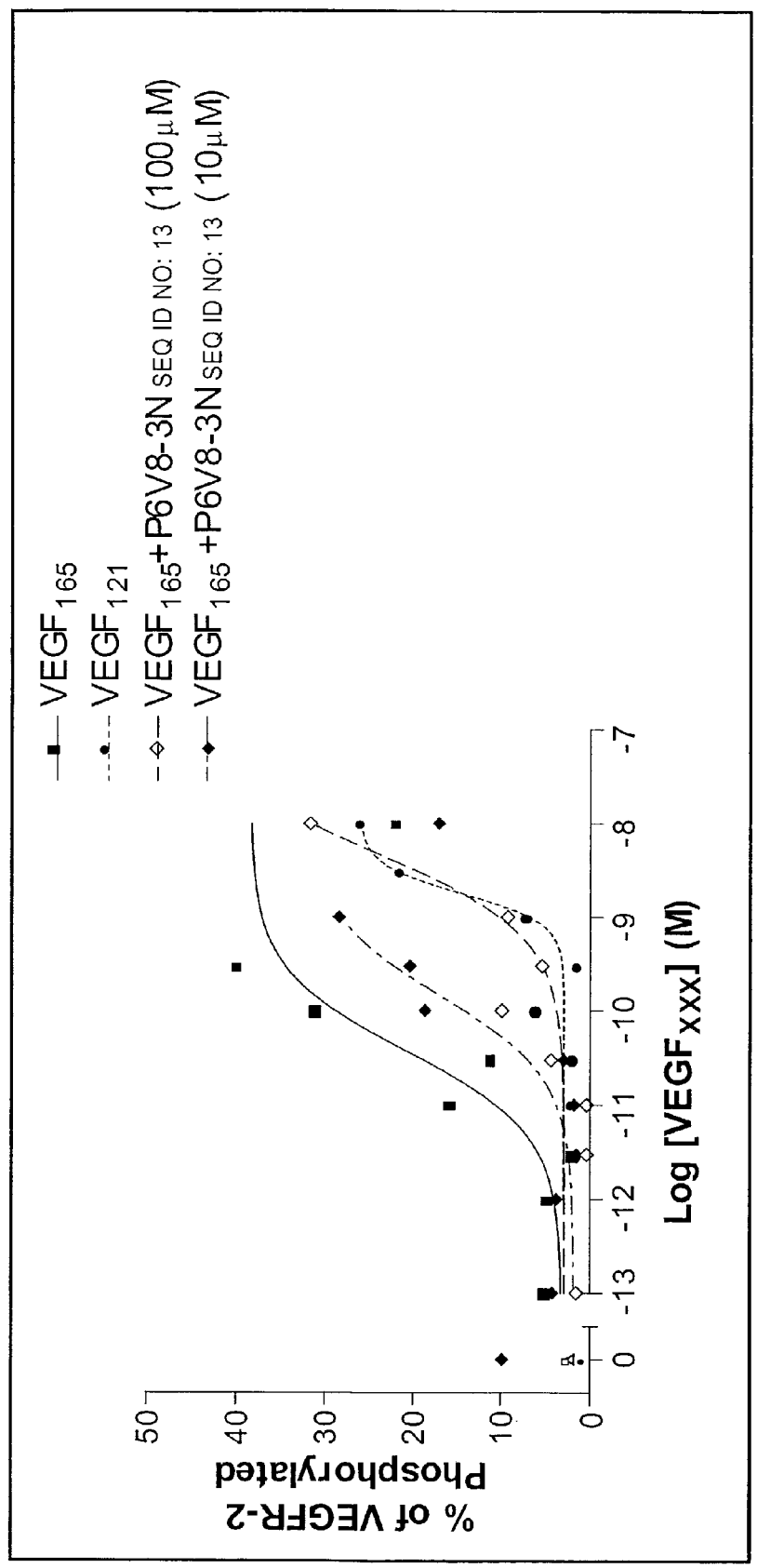
FIG. 13 is a graph of results demonstrating a dose-dependent shift in $VEGF_{165}$ potency by one of the inventive peptides.
Figure 14:
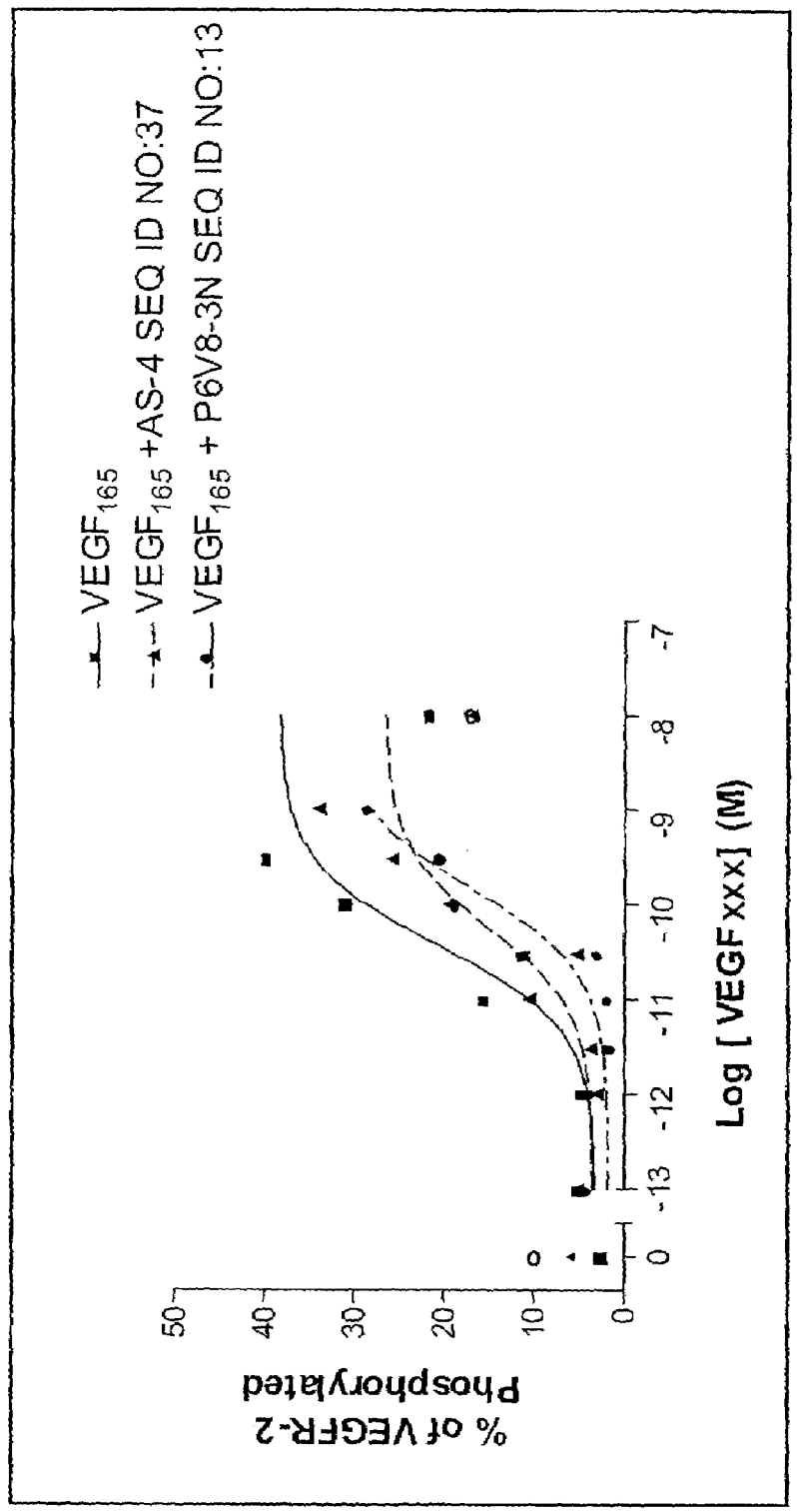
FIG. 14 is a graph of results comparing the magnitude of the shift in $VEGF_{165}$ potency for two of the inventive peptides.

Table 9 lists the peptides selected for the experiments depicted in FIGS. 13 and 14, and illustrates that the relative affinities and selectivity observed in the transient expression system are confirmed in the Balb/C 3T3 A31 stable expression system.

The potency of an antagonist is measured by the degree to which it shifts the agonist dose-response curve, with more potent antagonists providing measurable shifts in the agonist response at lower doses than that needed for weaker antagonists. The dose-dependence of the degree of shift is illustrated in FIG. 13 for the parent peptide P6V8-3N SEQ ID NO:13.

With reference to FIG. 13, HUVEC were stimulated with ligand for five minutes in the presence or absence of either 10 μM or 100 μM of P6V8-3N SEQ ID NO:13 at 37° C., lysed, and immunoprecipitated with an antibody specific to VEGFR-2. Following SDS-PAGE separation and transfer, the blots were probed using an antiphosphotyrosine antibody (4G10, UBI) and developed using standard ECL techniques. These same blots were stripped and reprobed using an antibody specific for VEGFR-2. The films were then scanned and quantitated using Image Quant (Molecular Dynamics). The non-linear regression analysis (Prism, San Diego, Calif.) of the PY/R2 signal ratio revealed the following results: VEGF$_{165}$ EC$_{50}$=37.3 pM; VEGF$_{121}$ EC$_{50}$=3.38 nM; VEGF$_{165}$+10 μM P6V8-3N SEQ ID NO:13 EC$_{50}$=142 pM; VEGF$_{165}$+100 μM P6V8-3N SEQ ID NO:13 EC$_{50}$=4.80 nM.

At 10 μM, P6V8-3N SEQ ID NO:13 produced a small but measurable shift in the EC$_{50}$ of VEGF$_{165}$ (VEGF$_{165}$ EC$_{50}$=37.3 pM; VEGF$_{165}$+10 μM P6V8-3N SEQ ID NO:13 EC$_{50}$=142 pM) from that of VEGF$_{165}$ alone. At 100 μM, however, the VEGF$_{165}$ dose response was shifted to a larger degree (VEGF$_{165}$+100 μM P6V8-3N SEQ ID NO:13 EC$_{50}$=4.8 nM). A peptide with higher receptor binding affinity than the parent P6V8-3N SEQ ID NO:13 would produce a greater shift in the VEGF$_{165}$ EC$_{50}$ at the 10 μM dose. Since AS-4 SEQ ID NO:37 has a substantially higher affinity at NP-1 than does P6V8-3N SEQ ID NO:13 (Table 9), AS-4 SEQ ID NO:37 would be predicted to shift the EC$_{50}$ of VEGF$_{165}$ further to the right than P6V8-3N SEQ ID NO:13 if the site of action was NP-1. However, if the site of action was the VEGFR-2/NP-1 complex, these two peptides would be expected to produce a similar shift in the EC$_{50}$ for VEGF$_{165}$ at the same dose of antagonist, since P6V8-3N SEQ ID NO:13 and AS-4 SEQ ID NO:37 exhibit comparative binding affinity in cells co-expressing VEGFR-2 and NP-1 (Table 9).

With reference to FIG. 14, HUVEC were stimulated with ligand for five minutes in the presence or absence of 10 μM AS-4 SEQ ID NO:37 or P6V8-3N SEQ ID NO:13 at 37° C., lysed, and immunoprecipitated with an antibody specific to VEGFR-2. Following SDS-PAGE separation and transfer, the blots were probed using an antiphosphotyrosine antibody (4G10, UBI) and developed using standard ECL techniques. These same blots were stripped and reprobed using an antibody specific for VEGFR-2. The films were then scanned and quantitated using Image Quant (Molecular Dynamics). The non-linear regression analysis (Prism, San Diego, Calif.) of the PY/R2 signal ratio reveals the following: VEGF$_{165}$ EC$_{50}$=37.3 pM; VEGF$_{165}$+AS-4 SEQ ID NO:37 EC$_{50}$=56.0 pM; VEGF$_{165}$+P6V8-3N SEQ ID NO:13 EC$_{50}$=142 pM.

The NP-1 selective peptide (AS-4 SEQ ID NO:37) did not shift the dose response curve for VEGF$_{165}$ (VEGF$_{165}$ EC$_{50}$=37 pM; VEGF$_{165}$+10 μM AS-4 SEQ ID NO:37 EC$_{50}$=56 pM) any further to the right than the parent peptide (VEGF$_{165}$+10 μM P6V8-3N SEQ ID NO:13 EC$_{50}$=142 pM).

The site of action for these peptides is the VEGFR-2/NP-1 complex, rather than NP-1 alone, as suggested by this comparison of the relative binding affinities and antagonistic effect.

TABLE 10

Relative IC$_{50}$ values for peptides tested

| Peptide | R2 Cells REL AFF | SEM | N | NP1 Cells REL AFF | SEM | N | R2 + NP1 Cells REL AFF | SEM | N |
|---|---|---|---|---|---|---|---|---|---|
| VEGF$_{165}$ | 2.78 × 10$^{-10}$ | | 10 | 5.82 × 10$^{-10}$ | | 10 | 6.78 × 10$^{-10}$ | | 9 |
| VEGF$_{121}$ | 4 | 3 | 2 | NC | N/A | 0 | NC | N/A | 0 |
| P6V8-3N SEQ ID NO:13 | 475115 | 473303 | 2 | 1166 | 1162 | 3 | 1466 | 1047 | 4 |
| P6V8-8N SEQ ID NO:14 | 7396 | 0 | 1 | 753 | 0 | 1 | 135 | 0 | 1 |
| P6V8-9N SEQ ID NO:19 | NC | 0 | 1 | 13708 | 0 | 1 | 8375 | 0 | 1 |
| P6V8CS SEQ ID NO:5 | 6353 | 0 | 1 | 105 | 13 | 2 | 1237 | 411 | 2 |
| P6V8 SEQ ID NO:4 | 191 | 0 | 1 | 701 | 633 | 3 | 630 | 291 | 3 |
| P6P7 SEQ ID NO:7 | 89125 | 0 | 1 | NT | | | 1205 | 0 | 1 |
| P6 SEQ ID NO:1 | 5495 | 0 | 1 | 24536 | 13433 | 4 | 15161 | 9954 | 1 |
| P6V8-3NRGCS SEQ ID NO:31 | 15848 | 0 | 1 | 251 | 0 | 1 | 315 | 0 | 1 |
| P6V8-3NCS-1C SEQ ID NO:17 | 14387 | 0 | 1 | 924 | 0 | 1 | 1099 | 0 | 1 |
| P6V8-3NCSC13C18 SEQ ID NO:9 | NC | 0 | 1 | 500 | 0 | 1 | 132 | 0 | 1 |
| P6V8-3NCS-2C SEQ ID NO:18 | 10280 | 0 | 1 | 11066 | 0 | 1 | NT | 0 | 1 |
| RAND1 SEQ ID NO:45 | NC | | | 2301 | 0 | 1 | 3515 | 0 | 1 |
| P6V8-3N SEQ ID NO:13 | 6322 | 1957 | 2 | 6594 | 2624 | 3 | 1435 | 147 | 3 |
| AS-1 SEQ ID NO:21 | NC | 0 | 1 | 944 | 0 | 1 | 2113 | 0 | 1 |
| AS-2 SEQ ID NO:22 | 62661 | 0 | 1 | 3365 | 0 | 1 | 14288 | 0 | 1 |
| AS-3 SEQ IDNO:23 | 27221 | 0 | 1 | 65 | 0 | 1 | NC | 0 | 1 |
| AS-4 SEQ ID NO:37 | NC | 0 | 1 | 55 | 0 | 1 | 6934 | 0 | 1 |
| AS-5 SEQ ID NO:39 | 12387 | 0 | 1 | 257 | 0 | 1 | 1297 | 0 | 1 |
| AS-4A SEQ ID NO:38 | NC | | | 194 | 0 | 1 | 1185 | 0 | 1 |
| P6V8-3NCS SEQ ID NO:20 | 72754 | 56781 | 4 | 1094 | 307 | 8 | 2556 | 1021 | 6 |
| V8 SEQ ID NO:2 | NC | 0 | 1 | NC | 0 | 1 | 12359 | 0 | 1 |
| V8CS SEQ ID NO:46 | NC | 0 | 1 | 2937650 | 0 | 1 | 50003 | 0 | 1 |
| P6V8-3NCSA3 SEQ ID NO:27 | 485288 | 0 | 1 | 1380 | 737 | 2 | 258 | 242 | 2 |
| P6V8-3NCSA6 SEQ ID NO:28 | 87297 | 0 | 1 | 713 | 539 | 2 | 5636 | 5227 | 2 |
| P6V8-3NCSA3A6 SEQ ID NO:29 | NC | 0 | 2 | 7728 | 4156 | 2 | 4543 | 1003 | 2 |
| P6V8-3NCSA7, 8, 10, 12 SEQ ID NO:47 | NC | 0 | 1 | 21428 | 0 | 1 | 6412 | 0 | 1 |
| P6V8-3NCS1-7CC SEQ ID NO:12 | 3334264 | 0 | 1 | 1071 | 339 | 5 | 44571704 | | 4 |
| P6V8-3NCSA5 SEQ ID NO:25 | 121338 | 0 | 1 | 1088 | 0 | 1 | 1819 | 0 | 1 |
| P6V8-3NCSA1A5 SEQ ID NO:26 | NC | 0 | 1 | 837 | 0 | 1 | 1782 | 0 | 1 |
| P6V8-3NCSA1A6 SEQ ID NO:30 | NC | 0 | 1 | 4187 | 0 | 1 | 2328 | 0 | 1 |
| P6V8-3NCSA1 SEQ ID NO:24 | 124165 | 0 | 1 | 413 | 0 | 1 | 17864 | 0 | 1 |
| P6V8-3NCSA16, 18, 19 SEQ ID NO:32 | 425598 | 0 | 1 | 103038 | 0 | 1 | NC | 0 | 1 |
| P6V8-3NCSA7, 8, 10, 12, 16, 18 SEQ ID NO:55 | NC | 0 | 1 | 103038 | 0 | 1 | 24660 | 0 | 1 |
| P6V8-3NCSA3A5 SEQ ID NO:48 | NC | 0 | 1 | 6338 | 0 | 1 | 21232 | 0 | 1 |
| (cap)P6V8-3NCS1-7CC SEQ ID NO:43 | NC | 0 | 2 | 141253 | 0 | 1 | 177010 | 0 | 1 |
| (cap)P6V8-3NCS SEQ ID NO:44 | NC | 0 | 2 | 52723 | 0 | 1 | 96161 | 0 | 1 |
| P6V8-3NCSA7, 8, 10 SEQ ID NO:33 | 110154 | 0 | 1 | 34674 | 0 | 1 | 27416 | 0 | 1 |
| P6V8-3NCSA7, 8, 12 SEQ ID NO:34 | 5997 | 0 | 1 | 30479 | 0 | 1 | 36644 | 0 | 1 |
| P6V8-3NCSA1, 5, 7, 8, 10 SEQ ID NO:35 | 212324 | 0 | 1 | 160325 | 0 | 1 | 43752 | 0 | 1 |
| P6V8-3NCS1-7CCA1 SEQ ID NO:40 | NC | 0 | 1 | 33574 | 0 | 1 | 5521 | 0 | 1 |
| P6V8-3NCS1-7CCA5 SEQ ID NO:41 | NC | 0 | 1 | 3837 | 0 | 1 | 5236 | 0 | 1 |
| P6V8-3NCS1-7CCA1A5 SEQ ID NO:42 | NC | 0 | 1 | 71945 | 0 | 1 | 48529 | 0 | 1 |
| P6V8-3NCSA1, 5, 7, 8, 12 SEQ ID NO:36 | NC | 0 | 1 | 25119 | 0 | 1 | 46026 | 0 | 1 |

Values displayed are relative to VEGF$_{165}$. (Except VEGF$_{165}$ which is listed as the antilog of the IC$_{50}$ for VEGF$_{165}$ at each receptor). Relative affinity is defined as the average of the IC$_{50}$ of the peptide divided by the IC$_{50}$ for VEGF in a matched experiment, SEM = Standard error of the mean, and N = # of experiments for the complete data set.

TABLE 11

Average EC$_{50}$ values attained with peptides in anti-phosphotyrosine assay at 100 μM

| Peptide | VEGF$_{165}$ Log EC$_{50}$ | SEM | EC$_{50}$ | N | VEGF$_{121}$ Log EC$_{50}$ | SEM | EC$_{50}$ | N |
|---|---|---|---|---|---|---|---|---|
| No Peptide added | −10.11 | 0.11 | 7.69 × 10$^{-11}$ | 14 | −8.61 | 0.09 | 2.45 × 10$^{-09}$ | 14 |

TABLE 11-continued

Average EC$_{50}$ values attained with peptides in anti-phosphotyrosine assay at 100 μM

| Peptide | VEGF$_{165}$ | | | | VEGF$_{121}$ | | | |
|---|---|---|---|---|---|---|---|---|
| | Log EC$_{50}$ | SEM | EC$_{50}$ | N | Log EC$_{50}$ | SEM | EC$_{50}$ | N |
| P6V8-3N SEQ ID NO:13 | −8.35 | 0 | $4.47 \times 10^{-09}$ | 1 | −8.93 | 0.34 | $1.17 \times 10^{-09}$ | 1 |
| P6V8 SEQ ID NO:4 | −7.23 | 0 | $5.94 \times 10^{-08}$ | 1 | −8.39 | 0 | $4.07 \times 10^{-09}$ | 1 |
| P6 SEQ ID NO:1 | −8.79 | 0.02 | $1.62 \times 10^{-09}$ | 2 | −8.62 | 0.19 | $2.40 \times 10^{-09}$ | 2 |
| P6V8-3NCSC13C18 SEQ ID NO:9 | −8.11 | 0 | $7.76 \times 10^{-09}$ | 1 | −8.68 | 0 | $2.09 \times 10^{-09}$ | 1 |
| P6V8-3N SEQ ID NO:13 | −8.25 | 0.08 | $5.69 \times 10^{-09}$ | 2 | −8.79 | 0 | $1.62 \times 10^{-09}$ | 1 |
| P6V8-3NCS SEQ ID NO:20 | −8.81 | 0.21 | $1.55 \times 10^{-09}$ | 4 | −8.34 | 0.48 | $4.57 \times 10^{-09}$ | 4 |
| P6V8-3NCSA7, 8, 10, 12 SEQ ID NO:47 | −8.99 | 0 | $1.02 \times 10^{-09}$ | 1 | −7.75 | 0 | $1.78 \times 10^{-08}$ | 1 |
| P6V8-3NCS1-7CC SEQ ID NO:12 | −8.80 | 0.27 | $1.58 \times 10^{-09}$ | 3 | −8.48 | 0.11 | $3.31 \times 10^{-09}$ | 3 |

Values displayed above are the antilog of the average log EC$_{50}$ of VEGF$_{165}$ obtained for VEGFR-2 activation in the anti-phosphotyrosine assay, obtained in the presence of 100 μM of the indicated peptide (see methods). The EC$_{50}$ values are reported for either VEGF$_{165}$ (left) or VEGF$_{121}$ (right) in the presence of the indicated peptides, compared to the EC$_{50}$ values for each agonist in the absence of added peptide (top row). SEM is the standard error of the mean, and N is the number of experiments averaged.

In vivo Studies

The peptide P6V8 SEQ ID NO:4 was provided as a frozen aqueous solution at 10 mM. A 0.2 μl aliquot of this solution yielded a 4 μg dose. Human recombinant VEGF$_{165}$ was purchased from R&D Systems (Minneapolis, Minn.), supplied in a lyophilized, carrier free form and reconstituted in the same water as the above peptide. A 0.2 μl aliquot of this solution yielded a 300 ng dose. The combination VEGF$_{165}$+P6V8 SEQ ID NO:4 treatment was formulated by adsorbing the dose of peptide and the dose of VEGF onto a single pellet of 12% hydron coated polyvinyl alcohol sponge substrate (total volume 0.4 μl).

Male albino mice (Crl: CD-I (ICR) BR, VAF) from Charles River (Portage, N.C.), 20–24 grams were used. This study tested the effects of the P6V8 SEQ ID NO:4 peptide in the mouse corneal pocket model. Treatment groups consisted of P6V8 SEQ ID NO:4 alone (n=4); VEGF$_{165}$ alone (n=8); and P6V8 SEQ ID NO:4+VEGF$_{165}$ (n=7). Compound adsorbed pellets were fabricated and implanted as described below. The treated eye was imaged on the day of implantation (day 0) and on days 4 and 7 following surgery. The growth response was subjectively graded on a scale from 0 to 6 by three independent graders blinded from the treatment grouping labels using the 3× printed image.

Polyvinyl alcohol (PVA) matrix material (Rippey, El Dorado Hills, Calif.) was cut into 1 cm×3 cm pieces and placed in a vibratome for sectioning on edge to produce 300 μm thick strips. The strips were individually sterilized by exposure to ethylene oxide. A strip was then cut under a dissecting microscope into approximately 300 μm cubes. The desired concentration of test compound or vehicle was adsorbed, sometimes utilizing a micro dessicant chamber. An HP auto sampler micro-syringe (Hamilton, P/N 7000.5) controlled the exact volume of the agent adsorbed onto the sponge. The sponge was then placed on a microscope slide prepared with a coating (20 μl spread over a 0.75 mm×1.5 mm area) of 12% hydron (Sigma, St. Louis, Mo.). The slide was protected in a clean petri dish and placed into a dessicator at 4° C. for a few hours or overnight. The dry, adsorbed sponges were mechanically flattened and overlaid with another aliquot of 12% hydron and again placed into a dessicator to cure the hydron coating. Fabrication of the adsorbed PVA sponge-hydron sandwich (referred to as a pellet) was done no more than 48 hours prior to implantation and the pellets were stored at 4° C. On the day of surgery and just prior to implantation, the pellet was trimmed so that the sponge remained encased by hydron (approximately 400 μm×400 μm×50 μm) and could be carefully removed from the slide.

Mice were anesthetized with 0.05 cc of Ketamine (140 mg/kg) and 0.03 cc Xylazine (17 mg/kg). A surgical plane of anesthesia was maintained by subsequent administration of half doses of the above compounds as needed. The whiskers on the animal's right side were trimmed down to ¼ of an inch. The right eye was bathed in an ophthalmic local anesthetic solution (Ophthaine, 0.5% tetracine hydrochloride) initially and throughout the procedure. The animal was placed on its side and the skin around the eye was gently retracted to expose the lateral and apical aspects of the cornea. The lateral limbic artery bifurcation was positioned horizontally. While stabilizing the eye against the ocular orbit, a vertical incision was made using a micro scalpel into the corneal tissue just lateral to the pupil. Care was taken to prevent accidental perforation of the anterior eye chamber. The incision depth was carefully deepened until a delicate and small lateral stab could be made (on axis with the lateral limbic artery bifurcation) with the micro scalpel into the middle of the corneal stroma. This lateral, intrastromal incision was enlarged by blunt dissection with very fine forceps until a pocket was formed from the vertical incision toward the limbus.

A hydron coated PVA sponge with adsorbed test compound (pellet) was prepared for implantation by carefully excising and removing it from the microscope slide. The pellet was introduced gently into the corneal pocket and advanced to within 1–2 mm of the limbus. The edges of the vertical corneal incision were approximated to encourage rapid healing. The imaging procedure (described below) was used to document the native limbic vascular architecture at the time of implantation. Post surgical recovery of the animal consisted of triple antibiotic ophthalmic ointment to prevent corneal drying, abrasion and infection.

The treated eye was imaged on the day of implantation and approximately every other day for a 7–12 day period under light anesthesia. Photographic prints and computerized digital images were obtained at various magnifications by direct illumination of the cornea. Briefly, mice were anesthetized with 0.03 cc of Ketamine and 0.02 cc Xylazine. The right eye was bathed in Ophthaine solution initially and throughout imaging. The animal was placed on its side and the skin around the right eye was gently retracted to expose the lateral and apical aspects of the cornea. The lateral limbic artery bifurcation was positioned horizontally and centered on the imaging screen. The illumination was adjusted so that the eyeball glowed from retinal reflected light and the limbic vessels were visualized. Digital and photographic imaging were obtained sequentially at 1×, 3× and 5× magnifications using Optimas v6.0 software and a color printer, respectively. Ophthalmic antibiotic ointment was applied to the right and left eyes after imaging to prevent corneal drying.

A subjective score was assigned to describe the overall neovascular response in the treated eyes as follows:

| | |
|---|---|
| NS = no visible growth | native limbic vasculature observed |
| #1 = minimal vascular growth | occasional and usually singular short vessel sprout(s) |
| #2 = modest vascular growth | 1–4 new vessels from a narrow limbic area directed toward the pellet |
| #3 = moderate vascular growth | 5–8 new vessels growing toward the pellet, originating from a small limbic area aligned on axis with the pellet |
| #4 = moderately strong vascular growth | more than 8 new vessels toward and almost reaching the pellet from a limbic region larger than 3× the pellet width |
| #5 = strong vascular growth | more than 20 new vessels from a large limbic region which reach the pellet |
| #6 = intense vascular growth | robust vascular growth toward and reaching the pellet, global limbic reaction |

The scores of the treated eyes in this study are as follows:

| Treatment group | Animal # | Score #1 | Score #2 | Score #3 |
|---|---|---|---|---|
| P6V8 SEQ ID NO:4 (4 µg) | 1 | 0 | 0 | 0 |
| | 2 | 0 | 0 | 0 |
| | 3 | 0 | 0 | 0 |
| | 4 | 0 | 0 | 0 |
| P6V8 SEQ ID NO: 4 + VEGF$_{165}$ | 5 | 2 | 3 | 1 |
| | 6 | 3 | 4 | 4 |
| | 7 | 2 | 0 | 2 |
| | 8 | 2 | 3 | 1 |
| | 9 | 3 | 3 | 3 |
| | 10 | 3 | 3 | 2 |
| | 11 | 2 | 1 | 1 |
| VEGF$_{165}$ (300 ng) | 12 | 2 | 2 | 2 |
| | 13 | 2 | 4 | 3 |
| | 14 | 3 | 2 | 2 |

-continued

| Treatment group | Animal # | Score #1 | Score #2 | Score #3 |
|---|---|---|---|---|
| | 15 | 4 | 4 | 4 |
| | 16 | 5 | 5 | 5 |
| | 17 | 3 | 2 | 2 |
| | 18 | 4 | 4 | 5 |
| | 19 | 3 | 4 | 3 |

The Pearson Correlation between any two graders was never lower than 0.85, indicating good agreement. Averaging all three grader scores over each eye image generated a treatment score for that eye. A one-sided Wilcoxin (Rank Sums) test was used to compare two groups at a time for differences. The null hypothesis was that the P6V8 SEQ ID NO:4 compound would attenuate the VEGF$_{165}$ vascular growth response. The VEGF$_{165}$ alone group served as the positive control since historical data demonstrated a moderately strong to strong angiogenic response at the 300 ng dose. The P6V8 SEQ ID NO:4 alone group served to verify that the peptide itself was not angiogenic or inflammatory in nature.

Figure 15:
FIG. 15 is a photograph of a mouse cornea treated with P6V8.
Figure 16:
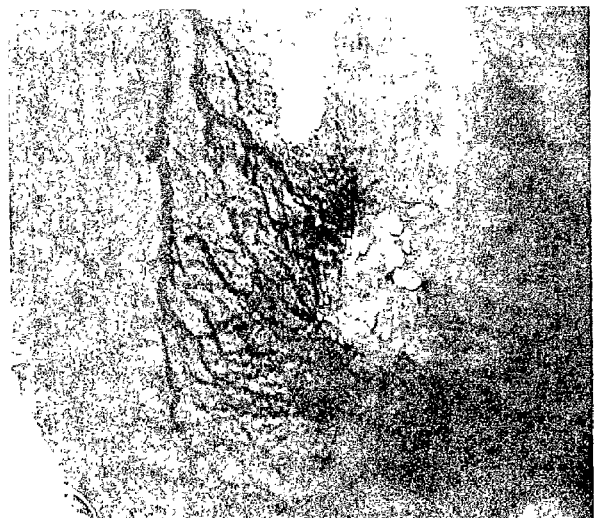
FIG. 16 is a photograph of a mouse cornea treated with $VEGF_{165}$.
Figure 17:
FIG. 17 is a photograph of a mouse cornea treated with $P6V8+VEGF_{165}$.

The VEGF$_{165}$ treated mice yielded significantly higher scores when compared to the combination P6V8 SEQ ID NO:4+VEGF$_{165}$ treated mice (p=0.0403) (significance at p<0.05). The P6V8 SEQ ID NO:4 alone treated mice yielded significantly lower scores when compared to the combination P6V8 SEQ ID NO:4+VEGF$_{165}$ treated mice (p=0.0043). The P6V8 SEQ ID NO:4 alone treated mice yielded significantly lower scores when compared to the VEGF$_{165}$ alone treated mice (p=0.0036). Notably, all graders scored eye images on Day 7 in the P6V8 SEQ ID NO:4 group 0, where 0 represents no change in limbic vasculature from Day 0. Representative images of the mouse eyes are found in FIGS. 15 to 17.

Thus, in the mouse corneal micro pocket model, the vascular growth response to 300 ng of VEGF$_{165}$ is attenuated in the presence of P6V8 SEQ ID NO:4. Although this compound has not been optimized, the in vivo results in a relatively small population of animals suggest that this peptide (at a dose of 4 µg) does have an inhibitory effect on the angiogenic properties of the VEGF growth factor. This effect is mediated through the actions of the P6V8 SEQ ID NO:4 peptide on the VEGFR-2/NP-1 complex.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

What is claimed is:

1. A peptide consisting of the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, said peptide capable of binding to neuropilin-1 (NP-1) or a vascular endothelial growth factor receptor-2 (VEGFR-2)/NP-1 complex.

2. An antagonist of $VEGF_{165}$ mediated VEGF-2 receptor activation consisting of the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, said peptide capable of binding to neuropilin-1 (NP-1) or a vascular endothelial growth factor receptor-2 (VEGFR-2)/NP-1 complex.

3. A composition consisting of the peptide of claim 1, and a pharmaceutically acceptable excipient.

* * * * *

SEQUENCE LISTING

<160> NUMBER OF SEQ ID NOS: 61

<210> SEQ ID NO 1
<211> LENGTH: 16
<212> TYPE: PRT
<213> ORGANISM: homo sapiens

<400> SEQUENCE: 1

Arg Arg Pro Lys Gly Arg Gly Lys Arg Arg Glu Lys Gln Arg Pro
1               5                   10                  15

<210> SEQ ID NO 2
<211> LENGTH: 8
<212> TYPE: PRT
<213> ORGANISM: homo sapiens

<400> SEQUENCE: 2

Arg Pro Cys Asp Lys Pro Arg Arg
1               5

<210> SEQ ID NO 3
<211> LENGTH: 8
<212> TYPE: PRT
<213> ORGANISM: homo sapiens

<400> SEQUENCE: 3

Arg Pro Asp Ala Val Pro Arg Arg
1               5

<210> SEQ ID NO 4
<211> LENGTH: 22
<212> TYPE: PRT
<213> ORGANISM: homo sapiens

<400> SEQUENCE: 4

Arg Arg Pro Lys Gly Arg Gly Lys Arg Arg Glu Lys Gln Arg Pro
1               5                   10                  15

Cys Asp Lys Pro Arg Arg
            20

<210> SEQ ID NO 5
<211> LENGTH: 22
<212> TYPE: PRT
<213> ORGANISM: homo sapiens

<400> SEQUENCE: 5

Arg Arg Pro Lys Gly Arg Gly Lys Arg Arg Glu Lys Gln Arg Pro
1               5                   10                  15

Ser Asp Lys Pro Arg Arg
            20

<210> SEQ ID NO 6
<211> LENGTH: 29
<212> TYPE: PRT
<213> ORGANISM: homo sapiens

<400> SEQUENCE: 6

Arg Arg Pro Lys Gly Arg Gly Lys Arg Arg Glu Lys Gln Arg Pro
1               5                   10                  15

Thr Asp Cys His Leu Cys Gly Asp Ala Val Pro Arg Arg
            20                  25

<210> SEQ ID NO 7
<211> LENGTH: 22
<212> TYPE: PRT
<213> ORGANISM: homo sapiens

<400> SEQUENCE: 7

Arg Arg Pro Lys Gly Arg Gly Lys Arg Arg Glu Lys Gln Arg Pro
1               5                   10                  15

```
Asp Ala Val Pro Arg Arg
            20

<210> SEQ ID NO 8
<211> LENGTH: 19
<212> TYPE: PRT
<213> ORGANISM: homo sapiens

<400> SEQUENCE: 8

Lys Gly Arg Gly Lys Arg Arg Cys Lys Gln Arg Pro Ser Asp Cys
 1               5                  10                  15

Pro Arg Arg

<210> SEQ ID NO 9
<211> LENGTH: 19
<212> TYPE: PRT
<213> ORGANISM: homo sapiens

<400> SEQUENCE: 9

Lys Gly Arg Gly Lys Arg Arg Glu Cys Gln Arg Pro Ser Cys Lys
 1               5                  10                  15

Pro Arg Arg

<210> SEQ ID NO 10
<211> LENGTH: 21
<212> TYPE: PRT
<213> ORGANISM: Artificial Sequence
<220> FEATURE:
<223> OTHER INFORMATION: Peptide
<220> FEATURE:
<221> NAME/KEY: misc. feature
<222> LOCATION: (1)...(21)
<223> OTHER INFORMATION: Xaa = any amino acid

<400> SEQUENCE: 10

Xaa Asx Ala Asx Ala Xaa Asx Asx Asx Xaa Asx Xaa Asx Pro Xaa Xaa
 1               5                  10                  15

Xaa Xaa Pro Asx Asx
            20

<210> SEQ ID NO 11
<211> LENGTH: 21
<212> TYPE: PRT
<213> ORGANISM: Artificial Sequence
<220> FEATURE:
<223> OTHER INFORMATION: Peptide
<220> FEATURE:
<221> NAME/KEY: misc. feature
<222> LOCATION: (1)...(21)
<223> OTHER INFORMATION: Xaa is any amino acid

<400> SEQUENCE: 11

Cys Asx Ala Asx Ala Xaa Asx Cys Asx Xaa Asx Xaa Asx Pro Xaa Xaa
 1               5                  10                  15

Xaa Xaa Pro Asx Asx
            20

<210> SEQ ID NO 12
<211> LENGTH: 20
<212> TYPE: PRT
<213> ORGANISM: homo sapiens

<400> SEQUENCE: 12

Cys Lys Gly Arg Gly Lys Arg Cys Arg Glu Lys Gln Arg Pro Ser Asp
 1               5                  10                  15
```

```
Lys Pro Arg Arg
        20

<210> SEQ ID NO 13
<211> LENGTH: 19
<212> TYPE: PRT
<213> ORGANISM: homo sapiens

<400> SEQUENCE: 13

Lys Gly Arg Gly Lys Arg Arg Glu Lys Gln Arg Pro Cys Asp Lys
1               5                   10                  15

Pro Arg Arg

<210> SEQ ID NO 14
<211> LENGTH: 14
<212> TYPE: PRT
<213> ORGANISM: homo sapiens

<400> SEQUENCE: 14

Arg Arg Arg Glu Lys Gln Arg Pro Cys Asp Lys Pro Arg Arg
1               5                   10

<210> SEQ ID NO 15
<211> LENGTH: 18
<212> TYPE: PRT
<213> ORGANISM: homo sapiens

<400> SEQUENCE: 15

Gly Arg Gly Lys Arg Arg Arg Glu Lys Gln Arg Pro Cys Asp Lys Pro
1               5                   10                  15

Arg Arg

<210> SEQ ID NO 16
<211> LENGTH: 15
<212> TYPE: PRT
<213> ORGANISM: homo sapiens

<400> SEQUENCE: 16

Lys Arg Arg Arg Glu Lys Gln Arg Pro Cys Asp Lys Pro Arg Arg
1               5                   10                  15

<210> SEQ ID NO 17
<211> LENGTH: 18
<212> TYPE: PRT
<213> ORGANISM: homo sapiens

<400> SEQUENCE: 17

Lys Gly Arg Gly Lys Arg Arg Arg Glu Lys Gln Arg Pro Ser Asp Lys
1               5                   10                  15

Pro Arg

<210> SEQ ID NO 18
<211> LENGTH: 17
<212> TYPE: PRT
<213> ORGANISM: homo sapiens

<400> SEQUENCE: 18

Lys Gly Arg Gly Lys Arg Arg Arg Glu Lys Gln Arg Pro Ser Asp Lys
1               5                   10                  15

Pro
```

```
<210> SEQ ID NO 19
<211> LENGTH: 13
<212> TYPE: PRT
<213> ORGANISM: homo sapiens

<400> SEQUENCE: 19

Arg Arg Glu Lys Gln Arg Pro Cys Asp Lys Pro Arg Arg
1               5                   10

<210> SEQ ID NO 20
<211> LENGTH: 19
<212> TYPE: PRT
<213> ORGANISM: homo sapiens

<400> SEQUENCE: 20

Lys Gly Arg Gly Lys Arg Arg Glu Lys Gln Arg Pro Ser Asp Lys
1               5                   10                  15

Pro Arg Arg

<210> SEQ ID NO 21
<211> LENGTH: 22
<212> TYPE: PRT
<213> ORGANISM: homo sapiens

<400> SEQUENCE: 21

Arg Arg Pro Ala Ala Gly Lys Arg Arg Glu Lys Gln Arg Pro
1               5                   10                  15

Ser Asp Lys Pro Arg Arg
            20

<210> SEQ ID NO 22
<211> LENGTH: 22
<212> TYPE: PRT
<213> ORGANISM: homo sapiens

<400> SEQUENCE: 22

Arg Arg Pro Lys Gly Arg Ala Ala Arg Glu Lys Gln Arg Pro
1               5                   10                  15

Ser Asp Lys Pro Arg Arg
            20

<210> SEQ ID NO 23
<211> LENGTH: 22
<212> TYPE: PRT
<213> ORGANISM: homo sapiens

<400> SEQUENCE: 23

Arg Arg Pro Lys Gly Arg Gly Lys Arg Ala Ala Lys Gln Arg Pro
1               5                   10                  15

Ser Asp Lys Pro Arg Arg
            20

<210> SEQ ID NO 24
<211> LENGTH: 19
<212> TYPE: PRT
<213> ORGANISM: homo sapiens

<400> SEQUENCE: 24

Ala Gly Arg Gly Lys Arg Arg Arg Glu Lys Gln Arg Pro Ser Asp Lys
1               5                   10                  15

Pro Arg Arg
```

```
<210> SEQ ID NO 25
<211> LENGTH: 19
<212> TYPE: PRT
<213> ORGANISM: homo sapiens

<400> SEQUENCE: 25

Lys Gly Arg Gly Ala Arg Arg Glu Lys Gln Arg Pro Ser Asp Lys
1               5                   10                  15

Pro Arg Arg

<210> SEQ ID NO 26
<211> LENGTH: 19
<212> TYPE: PRT
<213> ORGANISM: homo sapiens

<400> SEQUENCE: 26

Ala Gly Arg Gly Ala Arg Arg Glu Lys Gln Arg Pro Ser Asp Lys
1               5                   10                  15

Pro Arg Arg

<210> SEQ ID NO 27
<211> LENGTH: 19
<212> TYPE: PRT
<213> ORGANISM: homo sapiens

<400> SEQUENCE: 27

Lys Gly Ala Gly Lys Arg Arg Glu Lys Gln Arg Pro Ser Asp Lys
1               5                   10                  15

Pro Arg Arg

<210> SEQ ID NO 28
<211> LENGTH: 19
<212> TYPE: PRT
<213> ORGANISM: homo sapiens

<400> SEQUENCE: 28

Lys Gly Arg Gly Lys Ala Arg Arg Glu Lys Gln Arg Pro Ser Asp Lys
1               5                   10                  15

Pro Arg Arg

<210> SEQ ID NO 29
<211> LENGTH: 19
<212> TYPE: PRT
<213> ORGANISM: homo sapiens

<400> SEQUENCE: 29

Lys Gly Ala Gly Lys Ala Arg Arg Glu Lys Gln Arg Pro Ser Asp Lys
1               5                   10                  15

Pro Arg Arg

<210> SEQ ID NO 30
<211> LENGTH: 19
<212> TYPE: PRT
<213> ORGANISM: homo sapiens

<400> SEQUENCE: 30

Ala Gly Arg Gly Lys Ala Arg Arg Glu Lys Gln Arg Pro Ser Asp Lys
1               5                   10                  15

Pro Arg Arg

<210> SEQ ID NO 31
```

```
<211> LENGTH: 19
<212> TYPE: PRT
<213> ORGANISM: homo sapiens

<400> SEQUENCE: 31

Lys Gly Arg Gly Lys Arg Arg Arg Glu Lys Gln Gly Pro Ser Asp Lys
1               5                   10                  15

Pro Arg Arg

<210> SEQ ID NO 32
<211> LENGTH: 19
<212> TYPE: PRT
<213> ORGANISM: homo sapiens

<400> SEQUENCE: 32

Lys Gly Arg Gly Lys Arg Arg Arg Glu Lys Gln Arg Pro Ser Asp Ala
1               5                   10                  15

Pro Ala Ala

<210> SEQ ID NO 33
<211> LENGTH: 19
<212> TYPE: PRT
<213> ORGANISM: homo sapiens

<400> SEQUENCE: 33

Lys Gly Arg Gly Lys Arg Ala Ala Glu Ala Gln Arg Pro Ser Asp Lys
1               5                   10                  15

Pro Arg Arg

<210> SEQ ID NO 34
<211> LENGTH: 19
<212> TYPE: PRT
<213> ORGANISM: homo sapiens

<400> SEQUENCE: 34

Lys Gly Arg Gly Lys Arg Ala Ala Glu Lys Gln Ala Pro Ser Asp Lys
1               5                   10                  15

Pro Arg Arg

<210> SEQ ID NO 35
<211> LENGTH: 19
<212> TYPE: PRT
<213> ORGANISM: homo sapiens

<400> SEQUENCE: 35

Ala Gly Arg Gly Ala Arg Ala Ala Glu Ala Gln Arg Pro Ser Asp Lys
1               5                   10                  15

Pro Arg Arg

<210> SEQ ID NO 36
<211> LENGTH: 19
<212> TYPE: PRT
<213> ORGANISM: homo sapiens

<400> SEQUENCE: 36

Ala Gly Arg Gly Ala Arg Ala Ala Glu Lys Gln Ala Pro Ser Asp Lys
1               5                   10                  15

Pro Arg Arg

<210> SEQ ID NO 37
<211> LENGTH: 22
```

```
<212> TYPE: PRT
<213> ORGANISM: homo sapiens

<400> SEQUENCE: 37

Arg Arg Pro Lys Gly Arg Gly Lys Arg Arg Glu Ala Ala Ala Pro
1               5                   10                  15

Ser Asp Lys Pro Arg Arg
            20

<210> SEQ ID NO 38
<211> LENGTH: 22
<212> TYPE: PRT
<213> ORGANISM: homo sapiens

<400> SEQUENCE: 38

Arg Arg Pro Lys Gly Arg Gly Lys Arg Arg Glu Lys Gln Arg Ala
1               5                   10                  15

Ala Ala Lys Pro Arg Arg
            20

<210> SEQ ID NO 39
<211> LENGTH: 22
<212> TYPE: PRT
<213> ORGANISM: homo sapiens

<400> SEQUENCE: 39

Arg Arg Pro Lys Gly Arg Gly Lys Arg Arg Glu Lys Gln Arg Pro
1               5                   10                  15

Ser Asp Ala Ala Ala Arg
            20

<210> SEQ ID NO 40
<211> LENGTH: 20
<212> TYPE: PRT
<213> ORGANISM: homo sapiens
<220> FEATURE:
<221> NAME/KEY: misc. feature
<222> LOCATION: (1)..(20)
<223> OTHER INFORMATION: Xaa = any amino acid

<400> SEQUENCE: 40

Xaa Ala Gly Arg Gly Lys Arg Xaa Arg Glu Lys Gln Arg Pro Ser Asp
1               5                   10                  15

Lys Pro Arg Arg
            20

<210> SEQ ID NO 41
<211> LENGTH: 20
<212> TYPE: PRT
<213> ORGANISM: homo sapiens
<220> FEATURE:
<221> NAME/KEY: misc_feature
<222> LOCATION: (1)..(20)
<223> OTHER INFORMATION: Xaa is any amino acid.

<400> SEQUENCE: 41

Xaa Lys Gly Arg Gly Ala Arg Xaa Arg Glu Lys Gln Arg Pro Ser Asp
1               5                   10                  15

Lys Pro Arg Arg
            20

<210> SEQ ID NO 42
<211> LENGTH: 20
<212> TYPE: PRT
```

```
<213> ORGANISM: homo sapiens
<220> FEATURE:
<221> NAME/KEY: misc. feature
<222> LOCATION: (1)..(20)
<223> OTHER INFORMATION: Xaa= amino acid

<400> SEQUENCE: 42

Xaa Ala Gly Arg Gly Ala Arg Xaa Arg Glu Lys Gln Arg Pro Ser Asp
1               5                   10                  15

Lys Pro Arg Arg
            20

<210> SEQ ID NO 43
<211> LENGTH: 20
<212> TYPE: PRT
<213> ORGANISM: homo sapiens
<220> FEATURE:
<221> NAME/KEY: misc. feature
<222> LOCATION: (1)..(20)
<223> OTHER INFORMATION: Xaa= any amino acid

<400> SEQUENCE: 43

Xaa Lys Gly Arg Gly Lys Arg Xaa Arg Glu Lys Gln Arg Pro Ser Asp
1               5                   10                  15

Lys Pro Arg Arg
            20

<210> SEQ ID NO 44
<211> LENGTH: 19
<212> TYPE: PRT
<213> ORGANISM: homo sapiens

<400> SEQUENCE: 44

Lys Gly Arg Gly Lys Arg Arg Arg Glu Lys Gln Arg Pro Ser Asp Lys
1               5                   10                  15

Pro Arg Arg

<210> SEQ ID NO 45
<211> LENGTH: 22
<212> TYPE: PRT
<213> ORGANISM: homo sapiens

<400> SEQUENCE: 45

Pro Lys Arg Ser Arg Arg Lys Gly Gln Pro Arg Pro Arg Gly Arg Arg
1               5                   10                  15

Glu Lys Arg Asp Arg Lys
            20

<210> SEQ ID NO 46
<211> LENGTH: 8
<212> TYPE: PRT
<213> ORGANISM: homo sapiens

<400> SEQUENCE: 46

Arg Pro Ser Asp Lys Pro Arg Arg
1               5

<210> SEQ ID NO 47
<211> LENGTH: 19
<212> TYPE: PRT
<213> ORGANISM: homo sapiens

<400> SEQUENCE: 47

Lys Gly Arg Gly Lys Arg Ala Ala Glu Ala Gln Ala Pro Ser Asp Lys
```

```
                   1               5                  10                 15
Pro Arg Arg

<210> SEQ ID NO 48
<211> LENGTH: 19
<212> TYPE: PRT
<213> ORGANISM: homo sapiens

<400> SEQUENCE: 48

Lys Gly Ala Gly Ala Arg Arg Arg Glu Lys Gln Arg Pro Ser Asp Lys
1               5                  10                 15

Pro Arg Arg

<210> SEQ ID NO 49
<211> LENGTH: 20
<212> TYPE: PRT
<213> ORGANISM: homo sapiens

<400> SEQUENCE: 49

Pro Lys Gly Arg Gly Lys Arg Arg Glu Lys Gln Arg Pro Cys Asp
1               5                  10                 15

Lys Pro Arg Arg
            20

<210> SEQ ID NO 50
<211> LENGTH: 17
<212> TYPE: PRT
<213> ORGANISM: homo sapiens

<400> SEQUENCE: 50

Arg Gly Lys Arg Arg Arg Glu Lys Gln Arg Pro Cys Asp Lys Pro Arg
1               5                  10                 15

Arg

<210> SEQ ID NO 51
<211> LENGTH: 16
<212> TYPE: PRT
<213> ORGANISM: homo sapiens

<400> SEQUENCE: 51

Gly Lys Arg Arg Arg Glu Lys Gln Arg Pro Cys Asp Lys Pro Arg Arg
1               5                  10                 15

<210> SEQ ID NO 52
<211> LENGTH: 14
<212> TYPE: PRT
<213> ORGANISM: homo sapiens

<400> SEQUENCE: 52

Lys Gly Arg Gly Lys Arg Arg Arg Glu Lys Gln Arg Pro Ser
1               5                  10

<210> SEQ ID NO 53
<211> LENGTH: 15
<212> TYPE: PRT
<213> ORGANISM: homo sapiens

<400> SEQUENCE: 53

Lys Gly Arg Gly Lys Arg Arg Arg Glu Lys Gln Arg Pro Ser Asp
1               5                  10                 15

<210> SEQ ID NO 54
```

```
<211> LENGTH: 6
<212> TYPE: PRT
<213> ORGANISM: homo sapiens

<400> SEQUENCE: 54

Cys Asp Lys Pro Arg Arg
 1               5

<210> SEQ ID NO 55
<211> LENGTH: 6
<212> TYPE: PRT
<213> ORGANISM: homo sapiens

<400> SEQUENCE: 55

Ser Asp Lys Pro Arg Arg
 1               5

<210> SEQ ID NO 56
<211> LENGTH: 35
<212> TYPE: DNA
<213> ORGANISM: homo sapiens

<400> SEQUENCE: 56
tatatctaga atggagaggg ggctgccgct cctct                               35

<210> SEQ ID NO 57
<211> LENGTH: 27
<212> TYPE: DNA
<213> ORGANISM: Homo sapiens

<400> SEQUENCE: 57
agcgctctgc agaccagttg gtgctat                                        27

<210> SEQ ID NO 58
<211> LENGTH: 30
<212> TYPE: DNA
<213> ORGANISM: homo sapiens

<400> SEQUENCE: 58
ccaggaattc tcatgcctcc gaataagtac                                     30

<210> SEQ ID NO 59
<211> LENGTH: 30
<212> TYPE: DNA
<213> ORGANISM: homo sapiens

<400> SEQUENCE: 59
tggtctgcag agcgctcccg cctgaactac                                     30

<210> SEQ ID NO 60
<211> LENGTH: 18
<212> TYPE: PRT
<213> ORGANISM: Artificial
<220> FEATURE:
<223> OTHER INFORMATION: Peptide

<400> SEQUENCE: 60

Asp Leu Asp Lys Lys Asn Pro Glu Ile Lys Ile Asp Glu Thr Gly Ser
 1               5                   10                  15

Thr Cys

<210> SEQ ID NO 61
<211> LENGTH: 22
<212> TYPE: PRT
```

-continued

```
<213> ORGANISM: Artificial
<220> FEATURE:
<223> OTHER INFORMATION: Peptide

<400> SEQUENCE: 61

Ser Lys Arg Lys Ser Arg Pro Val Ser Val Lys Thr Phe Glu Asp Ile
1               5                   10                  15

Pro Leu Glu Glu Pro Cys
            20
```